(12) United States Patent
Grice et al.

(10) Patent No.: US 11,273,159 B2
(45) Date of Patent: Mar. 15, 2022

(54) PHARMACEUTICAL FORMULATIONS

(71) Applicant: H. Lundbeck A/S, Valby (DK)

(72) Inventors: Cheryl A. Grice, Encinitas, CA (US);
Nicole S. White, San Diego, CA (US);
Joel P. Zingerman, Carlsbad, CA (US);
Hibreniguss Terefe, Piscataway, NJ (US); Isaac Ghebre-Sellassie, Morris Plains, NJ (US)

(73) Assignee: H. LUNDBECK A/S, Valby (DK)

( * ) Notice: Subject to any disclaimer, the term of this patent is extended or adjusted under 35 U.S.C. 154(b) by 21 days.

(21) Appl. No.: 16/349,042

(22) PCT Filed: Nov. 15, 2017

(86) PCT No.: PCT/US2017/061871
§ 371 (c)(1),
(2) Date: May 10, 2019

(87) PCT Pub. No.: WO2018/093950
PCT Pub. Date: May 24, 2018

(65) Prior Publication Data
US 2020/0188393 A1 Jun. 18, 2020

Related U.S. Application Data

(60) Provisional application No. 62/545,857, filed on Aug. 15, 2017, provisional application No. 62/423,124, filed on Nov. 16, 2016.

(51) Int. Cl.
*A61K 31/497* (2006.01)
*A61K 47/58* (2017.01)
*A61K 9/00* (2006.01)
*A61K 47/02* (2006.01)
*A61K 47/26* (2006.01)

(52) U.S. Cl.
CPC .......... *A61K 31/497* (2013.01); *A61K 9/0056* (2013.01); *A61K 47/02* (2013.01); *A61K 47/26* (2013.01); *A61K 47/58* (2017.08)

(58) Field of Classification Search
CPC .... A61K 31/497; A61K 9/0056; A61K 47/38; C07D 403/10; C07D 295/205
See application file for complete search history.

(56) References Cited

U.S. PATENT DOCUMENTS

| | | | |
|---|---|---|---|
| 4,327,725 A | 5/1982 | Cortese et al. |
| 4,624,848 A | 11/1986 | Lee |
| 4,968,509 A | 11/1990 | Radebaugh et al. |
| 5,323,907 A | 6/1994 | Kalvelage |
| 5,456,923 A | 10/1995 | Nakamichi et al. |
| 5,461,140 A | 10/1995 | Heller et al. |
| 5,516,527 A | 5/1996 | Curatolo |
| 5,622,721 A | 4/1997 | Dansereau et al. |
| 5,686,105 A | 11/1997 | Kelm et al. |
| 5,700,410 A | 12/1997 | Nakamichi et al. |
| 5,977,175 A | 11/1999 | Lin |
| 6,465,014 B1 | 10/2002 | Moroni et al. |
| 6,932,983 B1 | 8/2005 | Straub et al. |
| 9,133,148 B2 | 9/2015 | Cisar et al. |
| 9,487,495 B2 | 11/2016 | Cisar et al. |
| 10,450,302 B2 | 10/2019 | Blankman et al. |
| 10,463,753 B2 | 11/2019 | Grice et al. |
| 2008/0214524 A1 | 9/2008 | Lee et al. |
| 2010/0015225 A1 | 1/2010 | Diederich et al. |
| 2014/0163068 A1 | 6/2014 | Verwijs et al. |
| 2014/0212487 A1 | 7/2014 | Mogalian et al. |
| 2014/0357693 A1 | 12/2014 | Shaul et al. |
| 2015/0018335 A1 | 1/2015 | Cisar et al. |
| 2015/0064252 A1 | 3/2015 | Gorman et al. |
| 2015/0148330 A1 | 5/2015 | Cisar et al. |
| 2015/0313843 A1 | 11/2015 | Shaw et al. |
| 2018/0099951 A1* | 4/2018 | Blankman ............... A61P 29/00 |
| 2020/0055841 A1 | 2/2020 | Blankman et al. |
| 2020/0190063 A1 | 6/2020 | Grice et al. |
| 2021/0230145 A1 | 7/2021 | Blankman et al. |

FOREIGN PATENT DOCUMENTS

| | | |
|---|---|---|
| CN | 101530399 A | 9/2009 |
| CN | 104379578 A | 2/2015 |
| JP | 2006505494 A | 2/2006 |
| JP | 2008531509 A | 8/2008 |
| RU | 2292206 C2 | 1/2007 |
| WO | WO-2009135915 A1 | 11/2009 |
| WO | WO-2010063802 A1 | 6/2010 |
| WO | WO-2013103973 A1 | 7/2013 |
| WO | WO-2013159095 A1 | 10/2013 |
| WO | WO-2015081703 A1 | 6/2015 |
| WO | WO-2015179559 A2 | 11/2015 |

(Continued)

OTHER PUBLICATIONS

Alhouayek et al. Increasing endogenous 2-arachidonoylglycerol levels counteracts colitis and related systemic inflammation. FASEB 25(8):2711-2721 (2011).
Ameloot et al. Endocannabinoid control of gastric sensorimotor function in man. Aliment Pharmacol Ther 31(10):1123-1131 (2010).
Anderson et al. Actions of the dual FAAH/MAGL inhibitor JZL195 in a murine inflammatory pain model. Neuropharmacology 81:224-230 (2013).
Berge et al. Pharmaceutical Salts. Journal of Pharmaceutical Sciences 66(1):1-19 (Jan. 1977).
Bernstein. Crystal Structure Prediction and Polymorphism. ACA Transactions 39:14-23 (2004).

(Continued)

*Primary Examiner* — Shobha Kantamneni
(74) *Attorney, Agent, or Firm* — Wilson Sonsini Goodrich & Rosati

(57) ABSTRACT

Provided herein are pharmaceutical formulations comprising a monoacylglycerol lipase (MAGL) inhibitor, or a pharmaceutically acceptable salt thereof, and at least one pharmaceutically acceptable excipient.

15 Claims, No Drawings

(56) References Cited

FOREIGN PATENT DOCUMENTS

| WO | WO-2016149401 A2 | 9/2016 |
|----|------------------|--------|
| WO | WO-2016183097 A1 | 11/2016 |
| WO | WO-2018093946 A1 | 5/2018 |
| WO | WO-2018093947 A1 | 5/2018 |
| WO | WO-2018093949 A1 | 5/2018 |
| WO | WO-2018093950 A1 | 5/2018 |
| WO | WO-2018093953 A1 | 5/2018 |

OTHER PUBLICATIONS

Blake et al. Preliminary assessment of the efficacy, tolerability and safety of a cannabis-based medicine (Sativex) in the treatment of pain caused by rheumatoid arthritis. Rheumatology (Oxford) 45(1):50-52 (2006).
Blankman et al. A comprehensive profile of brain enzymes that hydrolyze the endocannabinoid 2-arachidonoylglycerol. Chem. Biol. 14:1347-1356 (2007).
Braga et al. Making crystals from crystals: a green route to crystal engineering and polymorphism. Chemical Communications (29):3635-45 (2005).
Burckhardt et al. The fibromyalgia impact questionnaire: development and validation. J Rheumatol 18(5):728-733 (1991).
Chang et al. Highly Selective Inhibitors of Monoacylglycerol Lipase Bearing a Reactive Group that is Bioisosteric with Endocannabinoid Substrates. ChemBiol 19(5):579-588 (2012).
Chang et al. Proteome-wide reactivity profiling identifies diverse carbamate chemotypes tuned for serine hydrolase inhibition. ACS Chern Biol 8:1590-1599 (2013).
Chen et al. Monoacylglycerol lipase is a therapeutic target for Alzheimer's disease. Cell Rep. 2(5):1329-1339 (2012).
Collin et al. A double-blind, randomized, placebo-controlled, parallel-group study of Sativex, in subjects with symptoms of spasticity due to multiple sclerosis. Neurol Res 32(5):451-459 (2010).
Collin et al. Randomized controlled trial of cannabis-based medicine in spasticity caused by multiple sclerosis. Eur J Neurol 14(3):290-296 (2007).
Fiz et al. Cannabis use in patients with fibromyalgia: effect on symptoms relief and health-related quality of life. PLoS One 6(4):e18440 (2011).
Fleisher et al. Improved oral drug delivery: solubility limitations overcome by the use of prodrugs. Advanced Drug Delivery Reviews 19:115-130 (1996).
Foster et al. Deuterium isotope effects in the metabolism of drugs and xenobiotics: implications for drug design. Adv Drug Res 14:1-36 (1985).
Fowler. Monoacylglycerol lipase—a target fordrug development? Br Pharmacol. 166:1568-1585 (2012).
Gately et al. Deuterioglucose: alteration of biodistribution by an isotope effect. J Nucl Med 27:388-394 (1986).
Gordon et al. The metabolism of the abortifacient terpene, (R)-(+)-pulegone, to a proximate toxin, menthofuran. Drug Metab Dispos 15:589-594(1987).
Guindon et al. Alterations in endocannabinoid tone following chemotherapy-induced peripheral neuropathy: effects of endocannabinoid deactivation inhibitors targeting fatty-acid amide hydrolase and monoacylglycerol lipase in comparison to reference analgesics following cisplatin treatment. Pharmacol Res 67(1):94-109 (2013).
Hanlon et al. Circadian rhythm of circulating levels of the endocannabinoid 2-arachidonoylglycerol. J Clin Endocrinol Metab 100:220-226 (2015).
Hill. Medical Marijuana for Treatment of Chronic Pain and Other Medical and Psychiatric Problems: A Clinical Review. JAMA 313(24):2474-2483 (2015).
Howard et al. Cannabis use in sickle cell disease: a questionnaire study. Br J Haematol 131(1):123-128 (2005).
Hruba et al. Simultaneous Inhibition of Fatty Acid Amide Hydrolase and Monoacylglycerol Lipase Shares Discriminative Stimulus Effects with delta9-Tetarhydrocannabinol in Mice. The Journal of Pharmacology and Experimental Therapeutics 353:261-268 (2015).
Jiang et al. (+)-Borneol alleviates mechanical hyperalgesia in models of chronic inflammatory and neuropathic pain in mice. Eur J Pharmacol 757:53-58 (2015).
Jones et al. Pharmaceutical Cocrystals: An Emerging Approach to Physical Property Enhancement. MRS Bulletin 31:875-879 (2006).
Khasabova et al. Increasing 2-arachidonoyl glycerol signaling in the periphery attenuates mechanical hyperalgesia in a model of bone cancer pain. Pharmacol Res 64(1):60-67 (2011).
King et al. URB602 inhibits monoacylglycerol lipase and selectively blocks 2-arachidonoylglycerol degradation in intact brain slices. Chem Biol 14(12):1357-1365 (2007).
Kinsey et al. Blockade of Endocannabinoid-Degrading Enzymes Attenuates Neuropathic Pain. J Pharmacol Exp Ther 330(3):902-910 (2009).
Kohli et al. Pain-related behaviors and neurochemical alterations in mice expressing sickle hemoglobin: modulation by cannabinoids. Blood 116(3):456-465 (2010).
Korhonen et al. Piperazine and piperidine carboxamides and carbamates as inhibitors of fatty acid amide hydrolase (FAAH) and monoacylglycerol lipase (MAGL). Bioorg Med Chem 22(23):6694-6705 (2014).
Kushner et al. Pharmacological uses and perspectives of heavy water and deuterated compounds. Can J Physiol Pharmacol 77:79-88 (1999).
Labar et al. A review on the monoacylglycerol lipase: at the interface between fat and endocannabinoid signalling. Curr Med Chem 17(24):2588-2607 (2010).
Langford et al. A double-blind, randomized, placebo-controlled, parallel-group study of THC/CBD oromucosal spray in combination with the existing treatment regimen, in the relief of central neuropathic pain in patients with multiple sclerosis. J Neurol 260(4):984-997 (2013).
Liberman et al. Pharmaceutical Dosage Forms. 2nd Ed. 1:209-214 (1990).
Lijinsky et al. Dose-response studies in carcinogenesis by nitroso-N-methyl-N-(2-phenyl)ethylamine in rats and the effects of deuterium substitution. Food Chem Toxicol 20:393-399 (1982).
Lijinsky et al. Dose-response studies with nitrosoheptamethyleneimine and its alpha-deuterium-labeled derivative in F344 rats. J Nat Cancer Inst 69:1127-1133 (1982).
Long et al. Characterization of tunable piperidine and piperazine carbamates as inhibitors of endocannabinoid hydrolases. J Med chem 53(4):1830-1842 (2010).
Long et al. Selective blockade of 2-arachidonoylglycerol hydrolysis produces cannabinoid behavioral effects. Nat Chem Biol. 5(1):37-44 (2009).
Ly et al. Increased cerebral cannabinoid-1 receptor availability is a stable feature of functional dyspepsia: a [F]MK-9470 Pet study. Psychother Psychosom 84(3):149-158 (2015).
Malik et al. Dronabinol increases pain threshold in patients with functional chest pain: a pilot double-blind placebo-controlled trial. Dis Esophagus 30(2):1-8 (2017).
Mangold et al. Effects of deuterium labeling on azido amino acid mutagenicity in *Salmonella typhimurium*. Mutat Res 308:33-42 (1994).
Meanwell et al. Synopsis of some recent tactical application of bioisosteres in drug design. J Med Chem 54(8):2529-2591 (2011).
Mease et al. A randomized, double-blind, placebo-controlled, phase III trial of pregabalin in the treatment of patients with fibromyalgia. J Rheumatol 35(3):502-514 (2008).
Mukhamadieva et al. Search For New Drugs Synthesis and Biological Activity of O-Carbamoylated 1,1,1,3,3,3-Hexafluoroisopropanols as New Specific Inhibitors of Carboxylesterase. Pharmaceutical Chemistry Journal 46(8):461-464 (2012).
Muller-Vahl et al. Treatment of Tourette Syndrome with Delta-9-Tetrahydrocannbinol (delta9-THC): No Influence on Neuropsychological Performance. Neuropsychopharmacology 28:384-388 (2003).
Müller-Vahl et al. Treatment of Tourette's syndrome with Delta 9-tetrahydrocannabinol (THC): a randomized crossover trial. Pharmacopsychiatry 35(2):57-61 (2002).

(56) References Cited

OTHER PUBLICATIONS

Niphakis et al. O-Hydroxyacetamide Carbamates as a Highly Potent and Selective Class of Endocannabinoid Hydrolase Inhibitors. ACS Chem. Neurosci. 3(5):418-426 (2012/Web2011).
Nomura et al. Endocannabinoid hydrolysis generates brain prostaglandins that promote neuroinflammation. Science 334(6057):809-813 (2011).
Patani et al. Bioisosterism: A Rational Approach in Drug Design. Chem. Rev. 96:3147-3176 (1996).
PCT/US2016/031668 International Search Report and Written Opinion dated Aug. 11, 2016.
PCT/US2017/061867 Invitation to Pay Additional Fees dated Jan. 22, 2018.
PCT/US2017/061871 International Search Report and Written Opinion dated Feb. 7, 2018.
PCT/US2017/061875 International Search Report and Written Opinion dated Feb. 7, 2018.
Piro et al. A dysregulated endocannabinoid-eicosanoid network supports pathogenesis in a mouse model of Alzheimer's disease. Cell Rep. 1(6):617-623 (2012).
Porsteinsson et al. Effect of citalopram on agitation in Alzheimer disease: the CitAD randomized clinical trial. JAMA 311(7):682-691 (2014).
Price. The computational prediction of pharmaceutical crystal structures and polymorphism. Advanced Drug Delivery Reviews 56:301-319 (2004).
PubChem CID 17217128 http://pubchem.ncbi.nlm.nih.gov/summary/summary.cgi?cid=17217128 Retrieved Apr. 30, 2013 Create Date: Nov. 13, 2007 (3 pgs.).
PubChem CID 3469875. Compound Summary downloaded at https://pubchem.ncbi.nlm.nih.gov/compound/3469875 on Jun. 5, 2019,pp. 1-8 (2019).
PubChem CID 3469875. http://pubchem.ncbi.nlm.nih.gov/summary/summary.cgi?cid=3469875Retrieved Mar. 4, 2013 Create Date: Sep. 8, 2005 (11 pgs.).
PubChem CID 669902 http://pubchem.ncbi.nlm.nih.gov/summary/summary.cgi?cid=669902 Retrieved May 1, 2013 Create Date: Jul. 8, 2005 (4 pgs.).
PubChem CID 71657619 Create date: Aug. 19, 2013 (12 pgs).
Rautio et al. Prodrugs: design and clinical applications. Nat Rev Drug Discov 7(3):255-270 (2008).
Rhyne et al. Effects of Medical Marijuana on Migraine Headache Frequency in an Adult Population. Pharmacotherapy 36:505-510 (2016).
Richardson et al. Characterisation of the cannabinoid receptor system in synovial tissue and fluid in patients with osteoarthritis and rheumatoid arthritis. Arthritis Res Ther 10(2):R43 (2008).
Rog et al. Randomized, controlled trial of cannabis-based medicine in central pain in multiple sclerosis. Neurology 65(6):812-819 (2005).
Sarchielli et al. Endocannabinoids in chronic migraine: CSF findings suggest a system failure. Neuropsychopharmacology 32(6):1384-1390 (2007).
Science IP Report dated Dec. 11, 2014 (126 pgs.).
Silverman. The Organic Chemistry of Drug Design and Drug Action. Academic Press (pp. 15-22) (1992).
Singh et al. Encyclopedia of Pharmaceutical Technology 2nd Ed. pp. 751-753 (2002).
Skrabek et al. Nabilone for the treatment of pain in fibromyalgia. J Pain 9(2):164-173 (2008).
South. Synthesis and Reactions of Halogenated Thiazole Isocyanates. Journal of Heterocyclic Chemistry 28:1003-1011 (1991).
Studnev et al. Synthesis, Antibacterial And Immunotropic Activity of Poly(fluoroalkyl-N-arylcarbamates. Pharmaceutical Chemistry Journal 36(12):654-657 (2002).
Thornber. Isosterism and molecular modification in drug design. Chem Soc Rev 8:563-580 (1979).
Turcotte et al. Nabilone as an adjunctive to gabapentin for multiple sclerosis-induced neuropathic pain: a randomized controlled trial. Pain Med 16(1):149-159 (2015).
U.S. Appl. No. 15/573,272 Office Action dated Dec. 14, 2018.
Urry et al. Free-radical chain addition reactions of aldehydes with perfluoro ketones and chloro perfluoro ketones. J Org Chem 32(2):347-352 (1967).
Volicer et al. Effects of dronabinol on anorexia and disturbed behavior in patients with Alzheimer's disease. Int J Geriatr Psychiatry 12(9):913-919 (1997).
Wade. Deuterium isotope effects on noncovalent interactions between molecules. Chem Biol Interact 117:191-217 (1999).
Walther et al. Randomized, controlled crossover trial of dronabinol, 2.5 mg, for agitation in 2 patients with dementia. J Clin Psychopharmacol 31(2):256-258 (2011).
Ware et al. The effects of nabilone on sleep in fibromyalgia: results of a randomized controlled trial. Anesth Analg 110(2):604-610 (2010).
Whiting et al. Cannabinoids for Medical Use: A Systematic Review and Meta-analysis. JAMA 313(24):2456-2473 (2015).
Zajicek et al. Cannabinoids for treatment of spasticity and other symptoms related to multiple sclerosis (CAMS study): multicentre randomised placebo-controlled trial. Lancet 362(9395):1517-1526 (2003).
Zello et al. Plasma and urine enrichments following infusion of L-[1-13C]phenylalanine and L-[ring-2H5]phenylalanine in humans: evidence for an isotope effect in renal tubular reabsorption. Metabolism 43:487-491 (1994).
Aitipamula et al. Polymorphs, Salts, and Cocrystals: What's in a Name? Cryst. Growth Des. 12:2147-2152 (2012).
Pellkofer et al. The major brain endocannabinoid 2-AG controls neuropathic pain and mechanical hyperalgesia in patiens with neuromyelitis optical. PLoS One 8(8):e71500 (2013).
U.S. Appl. No. 16/349,142 Office Action dated Oct. 16, 2020.
Brittain. Polymorphism in Pharmaceutical Solids. 192:1-241 (2009).
Caira. Crystalline Polymorphism of Organic Compounds. Topics in Current Chemistry. 198:163-208 (Jan. 1998).
Guindon et al. Peripheral Antinociceptive Effects of Inhibitors of Monoacylglycerol Lipase in a Rat Model of Inflammatory Pain. Br J Pharmacol 163(7):1464-1478 (2011).
Handbook of pharmaceutical excipients. 5th edition, edited by Raymond C Rowe, Paul J Sheskey and Sian C Owen, p. 132-133, 211-212, 430-432 (Dec. 31, 2006).
Long et al. Dual blockade of FAAH and MAGL identifies behavioral processes regulated by endocannabinoid crosstalk in vivo. PNAS USA 106(48):20270-20275 (2009).
Morissette et al. High-throughput crystallization: polymorphs, salts, co-crystals and solvates of pharmaceutical solids. Advanced Drug Delivery Reviews 56:275-300 (2004).
U.S. Appl. No. 16/349,142 Ex Parte Quayle Action dated Apr. 23, 2021.
U.S. Appl. No. 16/563,733 Office Action dated Jun. 11, 2020.
Guillory. Chapter 5: Generation of Polymorphs, Hydrates, Solvates, and Amorphous Solids. Polymorphism in Pharmaceutical Solids pp. 183-226 (Brittain, H.G., ed., 1999).
Haynes et al. Occurrence of pharmaceutically acceptable anions and cations in the Cambridge Structural Database. J Pharm Sci 94(10):2111-2120 (2005).
Hirayama, Noriaki (ed.) Yuuki kagoubutsu kessho sakusei hando bukku- genri to nouhau—(Handbook of production of crystals of organic compounds—principles and knowhow), Maruzen Publishing Co. Ltd, 2008, Jul. 25, p. 57-84.
Shah et al. Chapter 2: Approaches for Improving Bioavailability of Poorly Soluble Drugs. Pharmaceutical Dosage Forms: Tablets. 3rd edition, vol. 2, chapter 2 (Augsburger et al. editors), p. 62-66 (Dec. 31, 2008).
Stahl. Preparation of water-soluble compounds through salt formation. The Practice of Medicinal Chemistry, 2nd edition, p. 601-615 (Dec. 31, 2003).
Uknown. The polymorphism of medicines and crystallisation of medicines, pp. 273, 278, 305-17 (2002).

* cited by examiner

PHARMACEUTICAL FORMULATIONS

CROSS-REFERENCE

This application is a U.S. National Stage entry of PCT application PCT/US2017/61871 filed Nov. 15, 2017, which claims the benefit of U.S. Provisional Application No. 62/423,124, filed on Nov. 16, 2016, and U.S. Provisional Application No. 62/545,857, filed on Aug. 15, 2017, which are herein incorporated by reference in their entirety.

BACKGROUND OF THE INVENTION

Monoacylglycerol lipase (MAGL) is an enzyme responsible for hydrolyzing endocannabinoids such as 2-AG (2-arachidonoylglycerol), an arachidonate based lipid, in the nervous system. 1,1,1,3,3,3-Hexafluoropropan-2-yl 4-(2-(pyrrolidin-1-yl)-4-(trifluoromethyl)benzyl)piperazine-1-carboxylate is a MAGL inhibitor.

SUMMARY OF THE INVENTION

Provided herein are pharmaceutical formulations in solid dosage form comprising 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt thereof. In one aspect, described herein is a pharmaceutical formulation in a solid dosage form comprising:
  (a) about 1 mg to about 60 mg of 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt thereof,
  (b) about 5 mg to about 425 mg of a polymeric carrier;
  (c) about 0.2 mg to about 10 mg of a surfactant; and
  (d) 0.2 mg to about 10 mg of a glidant.

In some embodiments, the pharmaceutical formulation comprises about 10 mg to about 150 mg of the polymeric carrier. In some embodiments, the pharmaceutical formulation comprises about 14 mg to about 85 mg of the polymeric carrier. In some embodiments, the polymeric carrier is selected from polyvinyl pyrrolidone K30 (PVP K30), polyvinyl pyrrolidone K17 (PVP K17), polyvinyl pyrrolidone K12 (PVP K12), polyvinyl pyrrolidone vinyl acetate (PVPVA 64), hydroxypropylmethyl cellulose (HPMC), hydroxypropylmethylcellulose acetylsuccinate (HPMC AS), and methylmethacrylate polymers (Eudragit polymers). In some embodiments, the polymeric carrier is polyvinyl pyrrolidone K30 (PVP K30). In some embodiments, the polymeric carrier is polyvinyl pyrrolidone vinyl acetate (PVPVA 64). In some embodiments, the pharmaceutical formulation comprises about 0.2 mg to about 4 mg of a surfactant. In some embodiments, the pharmaceutical formulation comprises about 0.4 mg to about 2 mg of a surfactant. In some embodiments, the surfactant is selected from polysorbates, polaxomers, bile salts, glyceryl monostearate, sodium lauryl sulfate, sorbitan monooleate, polyoxyethylene sorbitan monooleate, copolymers of ethylene oxide and propylene oxide, and d-α-tocopheryl polyethylene glycol succinate (Vitamin E TPGS). In some embodiments, the surfactant is Polysorbate 80 (Tween 80). In some embodiments, the pharmaceutical formulation comprises about 0.2 mg to about 4 mg of a glidant. In some embodiments, the pharmaceutical formulation comprises about 0.4 mg to about 2 mg of a glidant. In some embodiments, the glidant is silicon dioxide or talc. In some embodiments, the glidant is silicon dioxide. In some embodiments, the pharmaceutical formulation further comprises a buffer selected from potassium dihydrogen phosphate, sodium bicarbonate, magnesium carbonate, sodium citrate, sodium dihydrogen phosphate, dipotassium monohydrogen phosphate, and disodium monohydrogen phosphate. In some embodiments, the pharmaceutical formulation comprises about 0.1 mg to about 5 mg of potassium dihydrogen phosphate. In some embodiments, the pharmaceutical formulation comprises about 0.2 mg to about 2 mg of potassium dihydrogen phosphate. In some embodiments, the pharmaceutical formulation further comprises about 1 mg to about 65 mg of a plasticizer. In some embodiments, the pharmaceutical formulation further comprises about 1 mg to about 30 mg of a plasticizer. In some embodiments, the pharmaceutical formulation further comprises about 2 mg to about 15 mg of a plasticizer. In some embodiments, the plasticizer is selected from PEG 400, triethyl citrate, triacetin, acetyl tributyl citrate, acetyl triethyl citrate, stearic acid, glycerin, polyethylene glycols, polyethylene glycol monomethyl ether, propylene glycol, sorbitol sorbitan solution, castor oil, diacetylated monoglycerides, dibutyl sebacates, and diethyl phthalate. In some embodiments, the plasticizer is PEG 400. In some embodiments, the pharmaceutical formulation further comprises about 15 mg to about 850 mg of a filler. In some embodiments, the pharmaceutical formulation further comprises about 20 mg to about 400 mg of a filler. In some embodiments, the pharmaceutical formulation further comprises about 30 mg to about 200 mg of a filler. In some embodiments, the filler is selected from lactose, mannitol, dicalcium phosphate, microcrystalline cellulose, silicified microcrystalline cellulose, starch, and pregelatinized starch (Starch 1500). In some embodiments, the filler is lactose, mannitol, or microcrystalline cellulose. In some embodiments, the filler is microcrystalline cellulose. In some embodiments, the pharmaceutical formulation further comprises about 3 mg to about 150 mg of a disintegrant. In some embodiments, the pharmaceutical formulation further comprises about 5 mg to about 50 mg of a disintegrant. In some embodiments, the pharmaceutical formulation further comprises about 6 mg to about 30 mg of a disintegrant. In some embodiments, the disintegrant is selected from povidone, crospovidone, hypromellose, croscarmellose sodium, hydroxypropyl cellulose, and polyvinyl alcohol. In some embodiments, the disintegrant is crospovidone. In some embodiments, the disintegrant is croscarmellose sodium. In some embodiments, the pharmaceutical formulation further comprises about 0.1 mg to about 10 mg of a lubricant. In some embodiments, the pharmaceutical formulation further comprises about 0.2 mg to about 4 mg of a lubricant. In some embodiments, the pharmaceutical formulation further comprises about 0.3 mg to about 1.5 mg of a lubricant. In some embodiments, the lubricant is selected from magnesium stearate, stearic acid, and sodium stearyl fumarate. In some embodiments, the lubricant is sodium stearyl fumarate. In some embodiments, the lubricant is magnesium stearate.

In some embodiments, described herein is a pharmaceutical formulation in a solid dosage form comprising:
  (a) about 1 mg to about 60 mg of 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt thereof;
  (b) about 20 mg to about 400 mg of a filler;
  (c) about 3 mg to about 150 mg of a disintegrant; and
  (d) about 0.1 mg to about 10 mg of a lubricant.

In some embodiments, the pharmaceutical formulation further comprises about 30 mg to about 200 mg of a filler. In some embodiments, the pharmaceutical formulation further comprises about 50 mg to about 175 mg of a filler. In some embodiments, the filler is selected from lactose, mannitol, dicalcium phosphate, microcrystalline cellulose, silicified microcrystalline cellulose, starch, and pregelatinized starch (Starch 1500). In some embodiments, the filler is lactose, mannitol, or microcrystalline cellulose. In some embodiments, the filler is microcrystalline cellulose. In some embodiments, the pharmaceutical formulation further comprises about 5 mg to about 50 mg of a disintegrant. In some embodiments, the pharmaceutical formulation further comprises about 5 mg to about 25 mg of a disintegrant. In some embodiments, the pharmaceutical formulation further comprises about 6 mg to about 15 mg of a disintegrant. In some embodiments, the disintegrant is selected from povidone, crospovidone, hypromellose, croscarmellose sodium, hydroxypropyl cellulose, and polyvinyl alcohol. In some embodiments, the disintegrant is crospovidone. In some embodiments, the disintegrant is croscarmellose sodium. In some embodiments, the pharmaceutical formulation further comprises about 0.2 mg to about 4 mg of a lubricant. In some embodiments, the pharmaceutical formulation further comprises about 0.5 mg to about 2.5 mg of a lubricant. In some embodiments, the lubricant is selected from magnesium stearate, stearic acid, and sodium stearyl fumarate. In some embodiments, the lubricant is sodium stearyl fumarate. In some embodiments, the lubricant is magnesium stearate.

In some embodiments, the pharmaceutical formulation comprises about 1 mg to about 30 mg of the 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt thereof. In some embodiments, the pharmaceutical formulation comprises about 2 mg to about 15 mg of the 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt thereof. In some embodiments, the 1,1,1,3,3,3-hexafluoropropan-2-yl 4-(2-(pyrrolidin-1-yl)-4-(trifluoromethyl)benzyl)piperazine-1-carboxylate is a free base. In some embodiments, the 1,1,1,3,3,3-hexafluoropropan-2-yl 4-(2-(pyrrolidin-1-yl)-4-(trifluoromethyl)benzyl)piperazine-1-carboxylate is a hydrochloride salt. In some embodiments, the 1,1,1,3,3,3-hexafluoropropan-2-yl 4-(2-(pyrrolidin-1-yl)-4-(trifluoromethyl)benzyl)piperazine-1-carboxylate is a fumarate salt.

Further provided herein is a pharmaceutical formulation in a solid dosage form comprising:
(a) about 2 mg to about 12 mg of 1,1,1,3,3,3-hexafluoropropan-2-yl 4-(2-(pyrrolidin-1-yl)-4-(trifluoromethyl)benzyl)piperazine-1-carboxylate hydrochloride salt;
(b) about 14 mg to about 72.5 mg of polyvinyl pyrrolidone K30 (PVP K30);
(c) about 2 mg to about 13 mg of PEG 400;
(d) about 0.4 mg to about 2 mg of Polysorbate 80 (Tween 80);
(e) about 0.4 mg to about 2 mg of silicon dioxide;
(f) about 0.2 mg to about 1 mg of potassium dihydrogen phosphate;
(g) about 33 mg to about 170 mg of microcrystalline cellulose;
(h) about 6 mg to about 30 mg of crospovidone; and
(i) about 0.3 mg to about 1.5 mg of sodium stearyl fumarate.

Further provided herein is a pharmaceutical formulation in a solid dosage form comprising:
(a) about 2 mg to about 12 mg of 1,1,1,3,3,3-hexafluoropropan-2-yl 4-(2-(pyrrolidin-1-yl)-4-(trifluoromethyl)benzyl)piperazine-1-carboxylate hydrochloride salt;
(b) about 17 mg to about 85 mg of polyvinyl pyrrolidone vinyl acetate (PVPVA 64);
(c) about 0.4 mg to about 2 mg of Polysorbate 80 (Tween 80);
(d) about 0.4 mg to about 2 mg of silicon dioxide;
(e) about 0.2 mg to about 1 mg of potassium dihydrogen phosphate;
(f) about 33 mg to about 170 mg of microcrystalline cellulose;
(g) about 6 mg to about 30 mg of crospovidone; and
(h) about 0.3 mg to about 1.5 mg of sodium stearyl fumarate.

Further provided herein is a pharmaceutical formulation in a solid dosage form comprising:
(a) about 2 mg to about 12 mg of 1,1,1,3,3,3-hexafluoropropan-2-yl 4-(2-(pyrrolidin-1-yl)-4-(trifluoromethyl)benzyl)piperazine-1-carboxylate hydrochloride salt;
(b) about 14 mg to about 72.5 mg of polyvinyl pyrrolidone K30 (PVP K30);
(c) about 1 mg to about 13 mg of PEG 400;
(d) about 0.4 mg to about 2 mg of Polysorbate 80 (Tween 80);
(e) about 0.4 mg to about 2 mg of silicon dioxide;
(f) about 0.2 mg to about 1 mg of potassium dihydrogen phosphate;
(g) about 33 mg to about 170 mg of microcrystalline cellulose;
(h) about 6 mg to about 30 mg of croscarmellose sodium; and
(i) about 0.3 mg to about 1.5 mg of sodium stearyl fumarate; and
(j) about 2 mg to about 10 mg of Opadry AMB II Beige.

Further provided herein is a pharmaceutical formulation in a solid dosage form comprising:
(a) about 10 mg of 1,1,1,3,3,3-hexafluoropropan-2-yl 4-(2-(pyrrolidin-1-yl)-4-(trifluoromethyl)benzyl)piperazine-1-carboxylate hydrochloride salt;
(b) about 72.1 mg of polyvinyl pyrrolidone K30 (PVP K30);
(c) about 12.9 mg of PEG 400;
(d) about 2 mg of Polysorbate 80 (Tween 80);
(e) about 2 mg of silicon dioxide;
(f) about 1 mg of potassium dihydrogen phosphate;
(g) about 168.5 mg of microcrystalline cellulose;
(h) about 30 mg of crospovidone; and
(i) about 1.5 mg of sodium stearyl fumarate.

Further provided herein is a pharmaceutical formulation in a solid dosage form comprising:
(a) about 10.7 mg of 1,1,1,3,3,3-hexafluoropropan-2-yl 4-(2-(pyrrolidin-1-yl)-4-(trifluoromethyl)benzyl)piperazine-1-carboxylate hydrochloride salt;
(b) about 72.1 mg of polyvinyl pyrrolidone K30 (PVP K30);
(c) about 12.9 mg of PEG 400;
(d) about 2 mg of Polysorbate 80 (Tween 80);
(e) about 2 mg of silicon dioxide;
(f) about 1 mg of potassium dihydrogen phosphate;
(g) about 168.5 mg of microcrystalline cellulose;
(h) about 30 mg of crospovidone; and
(i) about 1.5 mg of sodium stearyl fumarate.

Further provided herein is a pharmaceutical formulation in a solid dosage form comprising:
(a) about 10 mg of 1,1,1,3,3,3-hexafluoropropan-2-yl 4-(2-(pyrrolidin-1-yl)-4-(trifluoromethyl)benzyl)piperazine-1-carboxylate hydrochloride salt;

(b) about 85 mg of polyvinyl pyrrolidone vinyl acetate (PVPVA 64);
(c) about 2 mg of Polysorbate 80 (Tween 80);
(d) about 2 mg of silicon dioxide;
(e) about 1 mg of potassium dihydrogen phosphate;
(f) about 168.5 mg of microcrystalline cellulose;
(g) about 30 mg of crospovidone; and
(h) about 1.5 mg of sodium stearyl fumarate.

Further provided herein is a pharmaceutical formulation in a solid dosage form comprising:
(a) about 2.1 mg of 1,1,1,3,3,3-hexafluoropropan-2-yl 4-(2-(pyrrolidin-1-yl)-4-(trifluoromethyl)benzyl)piperazine-1-carboxylate hydrochloride salt;
(b) about 156 mg of microcrystalline cellulose;
(c) about 10 mg of croscarmellose sodium; and
(d) about 1.7 mg of magnesium stearate.

Further provided herein is a pharmaceutical formulation in a solid dosage form comprising:
(a) about 10.7 mg of 1,1,1,3,3,3-hexafluoropropan-2-yl 4-(2-(pyrrolidin-1-yl)-4-(trifluoromethyl)benzyl)piperazine-1-carboxylate hydrochloride salt;
(b) about 147 mg of microcrystalline cellulose;
(c) about 10.2 mg of croscarmellose sodium; and
(d) about 1.7 mg of magnesium stearate.

Further provided herein is a pharmaceutical formulation in a solid dosage form comprising:
(a) about 53.6 mg of 1,1,1,3,3,3-hexafluoropropan-2-yl 4-(2-(pyrrolidin-1-yl)-4-(trifluoromethyl)benzyl)piperazine-1-carboxylate hydrochloride salt;
(b) about 104 mg of microcrystalline cellulose;
(c) about 10 mg of croscarmellose sodium; and
(d) about 1.7 mg of magnesium stearate.

Further provided herein is a pharmaceutical formulation in a solid dosage form comprising:
(a) about 2.1 mg of 1,1,1,3,3,3-hexafluoropropan-2-yl 4-(2-(pyrrolidin-1-yl)-4-(trifluoromethyl)benzyl)piperazine-1-carboxylate hydrochloride salt;
(b) about 15.1 mg of polyvinyl pyrrolidone K30 (PVP K30);
(c) about 1.6 mg of PEG 400;
(d) about 0.4 mg of Polysorbate 80 (Tween 80);
(e) about 0.4 mg of silicon dioxide;
(f) about 0.4 mg of potassium dihydrogen phosphate;
(g) about 121.7 mg of microcrystalline cellulose;
(h) about 7.5 mg of croscarmellose sodium;
(i) about 0.8 mg of sodium stearyl fumarate; and
(j) about 6.0 mg of Opadry AMB II Beige.

In some embodiments, the solid dosage form is selected from a powder, a tablet, a bite-disintegration tablet, a chewable tablet, a caplet, a capsule, a gelcap, an effervescent powder, a rapid-disintegration tablet, an abuse-deterrent tablet, a modified release tablet, a modified release caplet, a modified release capsule, and an aqueous suspension produced from a powder. In some embodiments, the solid dosage form is a tablet. In some embodiments, the pharmaceutical formulation further comprises about 2 mg to about 10 mg of a film coating. In some embodiments, the pharmaceutical formulation further comprises about 4 mg to about 8 mg of a film coating. In some embodiments, the pharmaceutical formulation further comprises about 2 mg of a film coating. In some embodiments, the pharmaceutical formulation further comprises about 3 mg of a film coating. In some embodiments, the pharmaceutical formulation further comprises about 4 mg of a film coating. In some embodiments, the pharmaceutical formulation further comprises about 5 mg of a film coating. In some embodiments, the pharmaceutical formulation further comprises about 6 mg of a film coating. In some embodiments, the pharmaceutical formulation further comprises about 7 mg of a film coating. In some embodiments, the pharmaceutical formulation further comprises about 8 mg of a film coating. In some embodiments, the pharmaceutical formulation further comprises about 9 mg of a film coating. In some embodiments, the pharmaceutical formulation further comprises about 10 mg of a film coating. In some embodiments, the film coating is Opadry AMB II Beige. In some embodiments, the solid dosage form is a caplet. In some embodiments, the solid dosage form is a capsule. In some embodiments, the 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt thereof, is crystalline. In some embodiments, the 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt thereof, is amorphous. In some embodiments, the pharmaceutical formulation is manufactured by a hot melt extrusion process. In some embodiments, the pharmaceutical formulation is manufactured by a sprayed-dried dispersion (SDD) process. In some embodiments, the pharmaceutical formulation comprises a self-emulsifying drug delivery system, a self-microemulsifying drug delivery system, or a self-nanoemulsifying drug delivery system.

In another aspect, provided herein is a method of treating pain in a patient in need thereof, comprising administering to the patient in need thereof a therapeutically effective amount of a pharmaceutical formulation described herein. In some embodiments the pain is neuropathic pain. In some embodiments, the pain is inflammatory pain.

In another aspect, provided herein is a method of treating epilepsy/seizure disorder, multiple sclerosis, neuromyelitis optica (NMO), Tourette syndrome, Alzheimer disease, or abdominal pain associated with irritable bowel syndrome in a patient in need thereof, comprising administering to the patient in need thereof a therapeutically effective amount of a pharmaceutical formulation described herein.

DETAILED DESCRIPTION OF THE INVENTION

Certain Terminology

The singular forms "a," "an," and "the" include plural referents unless the context clearly dictates otherwise. Thus, for example, reference to "a drug" includes reference to one or more of such drugs, and reference to "an excipient" includes reference to one or more of such excipients. When ranges are used herein, all combinations and sub-combinations of ranges and specific embodiments therein are intended to be included. The term "about" when referring to a number or a numerical range means that the number or numerical range referred to is an approximation within experimental variability (or within statistical experimental error), and thus the number or numerical range varies between 1% and 15% of the stated number or numerical range.

The terms "formulation" and "composition," as used herein, are used interchangeably and refer to a mixture of two or more compounds, elements, or molecules. In some aspects the terms "formulation" and "composition" may be used to refer to a mixture of one or more active agents with a carrier or other excipients.

The terms "active agent," "active pharmaceutical agent," "drug," "active ingredient," and variants thereof are used interchangeably to refer to an agent or substance that has measurable specified or selected physiologic activity when administered to a subject in a significant or effective amount.

The compound described herein, 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt thereof, is a MAGL inhibitor compound. 1,1,1,3,3,3-hexafluoropropan-2-yl 4-(2-(pyrrolidin-1-yl)-4-(trifluoromethyl)benzyl)piperazine-1-carboxylate or a pharmaceutically acceptable salt thereof, refers to a compound with the following structure:

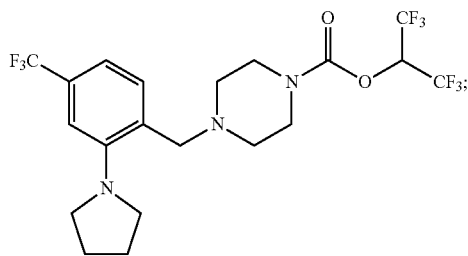 [SMILES: O=C(OC(C(F)(F)F)C(F)(F)F)N1CCN(Cc2ccc(C(F)(F)F)cc2N2CCCC2)CC1]

or a pharmaceutically acceptable salt thereof. In some embodiments, the 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt thereof, is crystalline. In some embodiments, the 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt thereof, is amorphous.

The term "pharmaceutically acceptable salt" in reference to 1,1,1,3,3,3-hexafluoropropan-2-yl 4-(2-(pyrrolidin-1-yl)-4-(trifluoromethyl)benzyl)piperazine-1-carboxylate refers to a salt of 1,1,1,3,3,3-hexafluoropropan-2-yl 4-(2-(pyrrolidin-1-yl)-4-(trifluoromethyl)benzyl)piperazine-1-carboxylate, which does not cause significant irritation to a mammal to which it is administered and does not substantially abrogate the biological activity and properties of the compound. A wide variety of pharmaceutically acceptable salts are formed from 1,1,1,3,3,3-hexafluoropropan-2-yl 4-(2-(pyrrolidin-1-yl)-4-(trifluoromethyl)benzyl)piperazine-1-carboxylate and include:

acid addition salts formed by reacting 1,1,1,3,3,3-hexafluoropropan-2-yl 4-(2-(pyrrolidin-1-yl)-4-(trifluoromethyl)benzyl)piperazine-1-carboxylate with an organic acid, which includes aliphatic mono- and dicarboxylic acids, phenyl-substituted alkanoic acids, hydroxyl alkanoic acids, alkanedioic acids, aromatic acids, aliphatic and aromatic sulfonic acids, amino acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, benzenesulfonic acid, p-toluenesulfonic acid, salicylic acid, and the like;

acid addition salts formed by reacting 1,1,1,3,3,3-hexafluoropropan-2-yl 4-(2-(pyrrolidin-1-yl)-4-(trifluoromethyl)benzyl)piperazine-1-carboxylate with an inorganic acid, which includes hydrochloric acid, hydrobromic acid, sulfuric acid, nitric acid, phosphoric acid, hydroiodic acid, hydrofluoric acid, phosphorous acid, and the like.

In some embodiments of the pharmaceutical formulations described herein, the 1,1,1,3,3,3-hexafluoropropan-2-yl 4-(2-(pyrrolidin-1-yl)-4-(trifluoromethyl)benzyl)piperazine-1-carboxylate is in the free base form. In some embodiments of the pharmaceutical formulations described herein, the 1,1,1,3,3,3-hexafluoropropan-2-yl 4-(2-(pyrrolidin-1-yl)-4-(trifluoromethyl)benzyl)piperazine-1-carboxylate is a salt. In some embodiments of the pharmaceutical formulations described herein, the 1,1,1,3,3,3-hexafluoropropan-2-yl 4-(2-(pyrrolidin-1-yl)-4-(trifluoromethyl)benzyl)piperazine-1-carboxylate is a hydrochloride salt. In some embodiments of the pharmaceutical formulations described herein, the 1,1,1,3,3,3-hexafluoropropan-2-yl 4-(2-(pyrrolidin-1-yl)-4-(trifluoromethyl)benzyl)piperazine-1-carboxylate is a fumarate salt.

It should be understood that a reference to a pharmaceutically acceptable salt includes the solvent addition forms (solvates). Solvates contain either stoichiometric or non-stoichiometric amounts of a solvent, and are formed during the process of product formation or isolation with pharmaceutically acceptable solvents such as water, ethanol, methanol, methyl tert-butyl ether (MTBE), diisopropyl ether (DIPE), ethyl acetate, isopropyl acetate, isopropyl alcohol, methyl isobutyl ketone (MIBK), methyl ethyl ketone (MEK), acetone, nitromethane, tetrahydrofuran (THF), dichloromethane (DCM), dioxane, heptanes, toluene, anisole, acetonitrile, and the like. In one aspect, solvates are formed using, but not limited to, Class 3 solvent(s). Categories of solvents are defined in, for example, the International Conference on Harmonization of Technical Requirements for Registration of Pharmaceuticals for Human Use (ICH), "Impurities: Guidelines for Residual Solvents, Q3C (R3), (November 2005). Hydrates are formed when the solvent is water, or alcoholates are formed when the solvent is alcohol. In some embodiments, solvates of 1,1,1,3,3,3-hexafluoropropan-2-yl 4-(2-(pyrrolidin-1-yl)-4-(trifluoromethyl)benzyl)piperazine-1-carboxylate, or pharmaceutically acceptable salts thereof, are conveniently prepared or formed during the processes described herein. In some embodiments, solvates of 1,1,1,3,3,3-hexafluoropropan-2-yl 4-(2-(pyrrolidin-1-yl)-4-(trifluoromethyl)benzyl)piperazine-1-carboxylate are anhydrous. In some embodiments, 1,1,1,3,3,3-hexafluoropropan-2-yl 4-(2-(pyrrolidin-1-yl)-4-(trifluoromethyl)benzyl)piperazine-1-carboxylate, or pharmaceutically acceptable salts thereof, exist in unsolvated form. In some embodiments, 1,1,1,3,3,3-hexafluoropropan-2-yl 4-(2-(pyrrolidin-1-yl)-4-(trifluoromethyl)benzyl)piperazine-1-carboxylate, or pharmaceutically acceptable salts thereof, exist in unsolvated form and are anhydrous.

In yet other embodiments, 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt thereof, is prepared in various forms, including but not limited to, amorphous phase, crystalline forms, milled forms and nano-particulate forms. In some embodiments, 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt thereof, is amorphous. In some embodiments, 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt thereof, is amorphous and anhydrous. In some embodiments, 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt thereof, is crystalline. In some embodiments, 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt thereof, is crystalline and anhydrous.

While not intending to be bound by any particular theory, certain solid forms are characterized by physical properties (e.g., stability, solubility and dissolution rate) appropriate for pharmaceutical and therapeutic dosage forms. Moreover, while not wishing to be bound by any particular theory, certain solid forms are characterized by physical properties (e.g., density, compressibility, hardness, morphology, cleavage, stickiness, solubility, water uptake, electrical properties, thermal behavior, solid-state reactivity, physical stability, and chemical stability) affecting particular processes (e.g., yield, filtration, washing, drying, milling, mixing, tableting, flowability, dissolution, formulation, and lyophilization) which make certain solid forms suitable for the manufacture of a solid dosage form. Such properties can be determined using particular analytical chemical techniques, including solid-state analytical techniques (e.g., X-ray diffraction, microscopy, spectroscopy and thermal analysis), as described herein and known in the art.

The terms "effective amount" or "therapeutically effective amount" as used herein, refer to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in a disease. An appropriate "effective" amount in any individual case may be determined using techniques, such as a dose escalation study.

Pharmaceutical Formulations

The 1,1,1,3,3,3-hexafluoropropan-2-yl 4-(2-(pyrrolidin-1-yl)-4-(trifluoromethyl)benzyl)piperazine-1-carboxylate pharmaceutical formulations described herein comprise 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt thereof, and at least one pharmaceutically acceptable excipient, in a solid dosage form. In some embodiments, the pharmaceutical formulations described herein comprise 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt thereof, and at least one pharmaceutically acceptable excipient, in a solid dosage form, wherein the solid dosage form is selected from a powder, a tablet, a bite-disintegration tablet, a chewable tablet, a caplet, a capsule, a gelcap, an effervescent powder, a rapid-disintegration tablet, an abuse-deterrent tablet, a modified release tablet, a modified release caplet, a modified release capsule, and an aqueous suspension produced from a powder. In some embodiments, the pharmaceutical formulations described herein comprise 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt thereof, and at least one pharmaceutically acceptable excipient, in a solid dosage form, wherein the solid dosage form is a tablet. In some embodiments, the pharmaceutical formulations described herein comprise 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt thereof, and at least one pharmaceutically acceptable excipient, in a solid dosage form, wherein the solid dosage form is a caplet. In some embodiments, the pharmaceutical formulations described herein comprise 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt thereof, and at least one pharmaceutically acceptable excipient, in a solid dosage form, wherein the solid dosage form is a capsule.

In some embodiments is a pharmaceutical formulation in a solid dosage form comprising:
(a) about 1 mg to about 60 mg of 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt thereof,
(b) about 5 mg to about 425 mg of a polymeric carrier;
(c) about 0.2 mg to about 10 mg of a surfactant; and
(d) about 0.2 mg to about 10 mg of a glidant.

In some embodiments described herein, the polymeric carrier is selected from polyvinyl pyrrolidone K30 (PVP K30), polyvinyl pyrrolidone K17 (PVP K17), polyvinyl pyrrolidone K12 (PVP K12), polyvinyl pyrrolidone vinyl acetate (PVPVA 64), hydroxypropylmethylcellulose (HPMC), hydroxypropylmethylcellulose acetylsuccinate (HPMC AS), and methylmethacrylate polymers (Eudragit polymers). In some embodiments, the polymeric carrier is polyvinyl pyrrolidone K30 (PVP K30). In some embodiments described herein, the polymeric carrier is polyvinyl pyrrolidone K17 (PVP K17). In some embodiments described herein, the polymeric carrier is polyvinyl pyrrolidone vinyl acetate (PVPVA 64). In some embodiments described herein, the polymeric carrier is hydroxypropylmethylcellulose (HPMC). In some embodiments described herein, the polymeric carrier is hydroxypropylmethylcellulose acetylsuccinate (HPMC AS). In some embodiments described herein, the polymeric carrier is methylmethacrylate polymers (Eudragit polymers). In some embodiments, the pharmaceutical formulation comprises about 5 mg to about 425 mg of the polymeric carrier. In some embodiments, the pharmaceutical formulation comprises about 5 mg to about 350 mg of the polymeric carrier. In some embodiments, the pharmaceutical formulation comprises about 5 mg to about 300 mg of the polymeric carrier. In some embodiments, the pharmaceutical formulation comprises about 5 mg to about 250 mg of the polymeric carrier. In some embodiments, the pharmaceutical formulation comprises about 5 mg to about 200 mg of the polymeric carrier. In some embodiments, the pharmaceutical formulation comprises about 5 mg to about 175 mg of the polymeric carrier. In some embodiments, the pharmaceutical formulation comprises about 5 mg to about 150 mg of the polymeric carrier. In some embodiments, the pharmaceutical formulation comprises about 10 mg to about 150 mg of the polymeric carrier. In some embodiments, the pharmaceutical formulation comprises about 10 mg to about 125 mg of the polymeric carrier. In some embodiments, the pharmaceutical formulation comprises about 10 mg to about 100 mg of the polymeric carrier. In some embodiments, the pharmaceutical formulation comprises about 10 mg to about 95 mg of the polymeric carrier. In some embodiments, the pharmaceutical formulation comprises about 10 mg to about 90 mg of the polymeric carrier. In some embodiments, the pharmaceutical formulation comprises about 12 mg to about 90 mg of the polymeric carrier. In some embodiments, the pharmaceutical formulation comprises about 10 mg to about 85 mg of the polymeric carrier. In some embodiments, the pharmaceutical formulation comprises about 12 mg to about 85 mg of the polymeric carrier. In some embodiments, the pharmaceutical formulation comprises about 12 mg to about 80 mg of the polymeric carrier. In some embodiments, the pharmaceutical formulation comprises about 14 mg to about 80 mg of the polymeric carrier. In some embodiments, the pharmaceutical formulation comprises about 12 mg to about 75 mg of the polymeric carrier. In some embodiments, the pharmaceutical formulation comprises about 14 mg to about 75 mg of the polymeric carrier. In some embodiments, the pharmaceutical formulation comprises about 5 mg of the polymeric carrier. In some embodiments, the pharmaceutical formulation comprises about 10 mg of the polymeric carrier. In some embodiments, the pharmaceutical formulation comprises about 11 mg of the polymeric carrier. In some embodiments, the pharmaceutical formulation comprises about 12 mg of the polymeric carrier. In some embodiments, the pharmaceutical formulation comprises about 13 mg of the polymeric carrier. In some embodiments, the pharmaceutical formulation comprises about 14 mg of the polymeric carrier. In some embodiments, the pharmaceutical formulation comprises about 15 mg of the polymeric carrier. In some embodiments, the pharmaceutical formulation comprises about 16 mg of the polymeric carrier. In some embodiments, the pharmaceutical formulation comprises about 17 mg of the polymeric carrier. In some embodiments, the pharmaceutical formulation comprises about 18 mg of the polymeric carrier. In some embodiments, the pharmaceutical formulation comprises about 19 mg of the polymeric carrier. In some embodiments, the pharmaceutical formulation comprises about 20 mg of the polymeric carrier. In some embodiments, the pharmaceutical formulation comprises about 25 mg of the polymeric carrier. In some embodiments, the pharmaceutical formulation comprises about 30 mg of the polymeric carrier. In some embodiments, the pharmaceutical formulation comprises about 35 mg of the polymeric carrier. In some embodiments, the pharmaceutical formulation comprises about 40 mg of the polymeric carrier. In some embodiments, the pharmaceutical formulation comprises about 45 mg of the polymeric carrier. In some embodiments, the pharmaceutical formulation comprises about 50 mg of the polymeric carrier. In some embodiments, the pharmaceutical formulation comprises about 55 mg of the polymeric carrier. In some embodiments, the pharmaceutical formulation comprises about 60 mg of the polymeric carrier. In some embodiments, the pharmaceutical formulation comprises about 65 mg of the polymeric carrier. In some embodiments, the pharmaceutical formulation comprises about 70 mg of the polymeric carrier. In some embodiments, the pharmaceutical formulation comprises about 75 mg of the polymeric carrier. In some embodiments, the pharmaceutical formulation comprises about 80 mg of the polymeric carrier. In some embodiments, the pharmaceutical formulation comprises about 85 mg of the polymeric carrier. In some embodiments, the pharmaceutical formulation comprises about 90 mg of the polymeric carrier. In some embodiments, the pharmaceutical formulation comprises about 95 mg of the polymeric carrier. In some embodiments, the pharmaceutical formulation comprises about 100 mg of the polymeric carrier. In some embodiments, the pharmaceutical formulation comprises about 10 mg to about 90 mg of the polymeric carrier, wherein the polymeric carrier is polyvinyl pyrrolidone K30 (PVP K30). In some embodiments, the pharmaceutical formulation comprises about 10 mg to about 90 mg of the polymeric carrier, wherein the polymeric carrier is polyvinyl pyrrolidone K17 (PVP K17). In some embodiments, the pharmaceutical formulation comprises about 10 mg to about 90 mg of the polymeric carrier, wherein the polymeric carrier is polyvinyl pyrrolidone K12 (PVP K12). In some embodiments, the pharmaceutical formulation comprises about 10 mg to about 90 mg of the polymeric carrier, wherein the polymeric carrier is polyvinyl pyrrolidone vinyl acetate (PVPVA 64). In some embodiments, the pharmaceutical formulation comprises about 10 mg to about 90 mg of the polymeric carrier, wherein the polymeric carrier is hydroxypropylmethylcellulose (HPMC). In some embodiments, the pharmaceutical formulation comprises about 10 mg to about 90 mg of the polymeric carrier, wherein the polymeric carrier is hydroxypropylmethylcellulose acetylsuccinate (HPMC AS). In some embodiments, the pharmaceutical formulation comprises about 10 mg to about 90 mg of the polymeric carrier, wherein the polymeric carrier is methylmethacrylate polymers (Eudragit polymers).

In some embodiments, the surfactant is selected from polysorbates, polaxomers, bile salts, glyceryl monostearate, sodium lauryl sulfate, sorbitan monooleate, polyoxyethylene sorbitan monooleate, copolymers of ethylene oxide and propylene oxide, and d-α-tocopheryl polyethylene glycol succinate (Vitamin E TPGS). In some embodiments, the surfactant is a polysorbate. In some embodiments, the surfactant is a Polysorbate 80 (Tween 80). In some embodiments, the surfactant is a polaxomer. In some embodiments, the surfactant is a bile salt. In some embodiments, the surfactant is glyceryl monostearate. In some embodiments, the surfactant is sodium lauryl sulfate. In some embodiments, the surfactant is sorbitan monooleate. In some embodiments, the surfactant is polyoxyethylene sorbitan monooleate. In some embodiments, the surfactant is a copolymer of ethylene oxide. In some embodiments, the surfactant is a copolymer of propylene oxide. In some embodiments, the surfactant is d-α-tocopheryl polyethylene glycol succinate (Vitamin E TPGS). In some embodiments, the pharmaceutical formulation comprises about 0.2 mg to about 10 mg of the surfactant. In some embodiments, the pharmaceutical formulation comprises about 0.2 mg to about 8 mg of the surfactant. In some embodiments, the pharmaceutical formulation comprises about 0.2 mg to about 7 mg of the surfactant. In some embodiments, the pharmaceutical formulation comprises about 0.2 mg to about 6 mg of the surfactant. In some embodiments, the pharmaceutical formulation comprises about 0.2 mg to about 5 mg of the surfactant. In some embodiments, the pharmaceutical formulation comprises about 0.2 mg to about 4 mg of the surfactant. In some embodiments, the pharmaceutical formulation comprises about 0.2 mg to about 3.5 mg of the surfactant. In some embodiments, the pharmaceutical formulation comprises about 0.2 mg to about 3 mg of the surfactant. In some embodiments, the pharmaceutical formulation comprises about 0.2 mg to about 2.5 mg of the surfactant. In some embodiments, the pharmaceutical formulation comprises about 0.2 mg to about 2 mg of the surfactant. In some embodiments, the pharmaceutical formulation comprises about 0.2 mg to about 1.5 mg of the surfactant. In some embodiments, the pharmaceutical formulation comprises about 0.2 mg to about 1 mg of the surfactant. In some embodiments, the pharmaceutical formulation comprises about 0.3 mg to about 5 mg of the surfactant. In some embodiments, the pharmaceutical formulation comprises about 0.3 mg to about 4 mg of the surfactant. In some embodiments, the pharmaceutical formulation comprises about 0.3 mg to about 3.5 mg of the surfactant. In some embodiments, the pharmaceutical formulation comprises about 0.3 mg to about 3 mg of the surfactant. In some embodiments, the pharmaceutical formulation comprises about 0.3 mg to about 2.5 mg of the surfactant. In some embodiments, the pharmaceutical formulation comprises about 0.3 mg to about 2 mg of the surfactant. In some embodiments, the pharmaceutical formulation comprises about 0.3 mg to about 1.5 mg of the surfactant. In some embodiments, the pharmaceutical formulation comprises about 0.3 mg to about 1 mg of the surfactant. In some embodiments, the pharmaceutical formulation comprises about 0.4 mg to about 5 mg of the surfactant. In some embodiments, the pharmaceutical formulation comprises about 0.4 mg to about 4 mg of the surfactant. In some embodiments, the pharmaceutical formulation comprises about 0.4 mg to about 3.5 mg of the surfactant. In some embodiments, the pharmaceutical formulation comprises about 0.4 mg to about 3 mg of the surfactant. In some embodiments, the pharmaceutical formulation comprises about 0.4 mg to about 2.5 mg of the surfactant. In some embodiments, the pharmaceutical formulation comprises about 0.4 mg to about 2 mg of the surfactant. In some embodiments, the pharmaceutical formulation comprises about 0.4 mg to about 1.5 mg of the surfactant. In some embodiments, the pharmaceutical formulation comprises about 0.4 mg to about 1 mg of the surfactant. In some embodiments, the pharmaceutical formulation comprises about 0.2 mg of the surfactant. In some embodiments, the pharmaceutical formulation comprises about 0.25 mg of the surfactant. In some embodiments, the pharmaceutical formulation comprises about 0.3 mg of the surfactant. In some embodiments, the pharmaceutical formulation comprises about 0.35 mg of the surfactant. In some embodiments, the pharmaceutical formulation comprises about 0.4 mg of the surfactant. In some embodiments, the pharmaceutical formulation comprises about 0.45 mg of the surfactant. In some embodiments, the pharmaceutical formulation comprises about 0.5 mg of the surfactant. In some embodiments, the pharmaceutical formulation comprises about 0.6 mg of the surfactant. In some embodiments, the pharmaceutical formulation comprises about 0.7 mg of the surfactant. In some embodiments, the pharmaceutical formulation comprises about 0.8 mg of the surfactant. In some embodiments, the pharmaceutical formulation comprises about 0.9 mg of the surfactant. In some embodiments, the pharmaceutical formulation comprises about 1 mg of the surfactant. In some embodiments, the pharmaceutical formulation comprises about 1.1 mg of the surfactant. In some embodiments, the pharmaceutical formulation comprises about 1.2 mg of the surfactant. In some embodiments, the pharmaceutical formulation comprises about 1.3 mg of the surfactant. In some embodiments, the pharmaceutical formulation comprises about 1.4 mg of the surfactant. In some embodiments, the pharmaceutical formulation comprises about 1.5 mg of the surfactant. In some embodiments, the pharmaceutical formulation comprises about 1.6 mg of the surfactant. In some embodiments, the pharmaceutical formulation comprises about 1.7 mg of the surfactant. In some embodiments, the pharmaceutical formulation comprises about 1.8 mg of the surfactant. In some embodiments, the pharmaceutical formulation comprises about 1.9 mg of the surfactant. In some embodiments, the pharmaceutical formulation comprises about 2 mg of the surfactant. In some embodiments, the pharmaceutical formulation comprises about 2.25 mg of the surfactant. In some embodiments, the pharmaceutical formulation comprises about 2.5 mg of the surfactant. In some embodiments, the pharmaceutical formulation comprises about 2.75 mg of the surfactant. In some embodiments, the pharmaceutical formulation comprises about 3 mg of the surfactant. In some embodiments, the pharmaceutical formulation comprises about 3.5 mg of the surfactant. In some embodiments, the pharmaceutical formulation comprises about 4 mg of the surfactant. In some embodiments, the pharmaceutical formulation comprises about 4.5 mg of the surfactant. In some embodiments, the pharmaceutical formulation comprises about 5 mg of the surfactant. In some embodiments, the pharmaceutical formulation comprises about 6 mg of the surfactant. In some embodiments, the pharmaceutical formulation comprises about 7 mg of the surfactant. In some embodiments, the pharmaceutical formulation comprises about 8 mg of the surfactant. In some embodiments, the pharmaceutical formulation comprises about 9 mg of the surfactant. In some embodiments, the pharmaceutical formulation comprises about 10 mg of the surfactant. In some embodiments, the pharmaceutical formulation comprises about 0.2 mg to about 10 mg of the surfactant, wherein the surfactant is Polysorbate 80 (Tween 80). In some embodiments, the pharmaceutical formulation comprises about 0.2 mg to about 5 mg of the surfactant, wherein the surfactant is Polysorbate 80 (Tween 80). In some embodiments, the pharmaceutical formulation comprises about 0.2 mg to about 4 mg of the surfactant, wherein the surfactant is Polysorbate 80 (Tween 80). In some embodiments, the pharmaceutical formulation comprises about 0.2 mg to about 3 mg of the surfactant, wherein the surfactant is Polysorbate 80 (Tween 80). In some embodiments, the pharmaceutical formulation comprises about 0.2 mg to about 2.5 mg of the surfactant, wherein the surfactant is Polysorbate 80 (Tween 80). In some embodiments, the pharmaceutical formulation comprises about 0.2 mg to about 2 mg of the surfactant, wherein the surfactant is Polysorbate 80 (Tween 80). In some embodiments, the pharmaceutical formulation comprises about 0.4 mg to about 4 mg of the surfactant, wherein the surfactant is Polysorbate 80 (Tween 80). In some embodiments, the pharmaceutical formulation comprises about 0.4 mg to about 3 mg of the surfactant, wherein the surfactant is Polysorbate 80 (Tween 80). In some embodiments, the pharmaceutical formulation comprises about 0.4 mg to about 2.5 mg of the surfactant, wherein the surfactant is Polysorbate 80 (Tween 80). In some embodiments, the pharmaceutical formulation comprises about 0.4 mg to about 2 mg of the surfactant, wherein the surfactant is Polysorbate 80 (Tween 80).

In some embodiments, the glidant is silicon dioxide or talc. In some embodiments, the glidant is talc. In some embodiments, the glidant is silicon dioxide. In some embodiments, the pharmaceutical formulation comprises about 0.2 mg to about 10 mg of the glidant. In some embodiments, the pharmaceutical formulation comprises about 0.2 mg to about 8 mg of the glidant. In some embodiments, the pharmaceutical formulation comprises about 0.2 mg to about 7 mg of the glidant. In some embodiments, the pharmaceutical formulation comprises about 0.2 mg to about 6 mg of the glidant. In some embodiments, the pharmaceutical formulation comprises about 0.2 mg to about 5 mg of the glidant. In some embodiments, the pharmaceutical formulation comprises about 0.2 mg to about 4 mg of the glidant. In some embodiments, the pharmaceutical formulation comprises about 0.2 mg to about 3.5 mg of the glidant. In some embodiments, the pharmaceutical formulation comprises about 0.2 mg to about 3 mg of the glidant. In some embodiments, the pharmaceutical formulation comprises about 0.2 mg to about 2.5 mg of the glidant. In some embodiments, the pharmaceutical formulation comprises about 0.2 mg to about 2 mg of the glidant. In some embodiments, the pharmaceutical formulation comprises about 0.2 mg to about 1.5 mg of the glidant. In some embodiments, the pharmaceutical formulation comprises about 0.2 mg to about 1 mg of the glidant. In some embodiments, the pharmaceutical formulation comprises about 0.3 mg to about 5 mg of the glidant. In some embodiments, the pharmaceutical formulation comprises about 0.3 mg to about 4 mg of the glidant. In some embodiments, the pharmaceutical formulation comprises about 0.3 mg to about 3.5 mg of the glidant. In some embodiments, the pharmaceutical formulation comprises about 0.3 mg to about 3 mg of the glidant. In some embodiments, the pharmaceutical formulation comprises about 0.3 mg to about 2.5 mg of the glidant. In some embodiments, the pharmaceutical formulation comprises about 0.3 mg to about 2 mg of the glidant. In some embodiments, the pharmaceutical formulation comprises about 0.3 mg to about 1.5 mg of the glidant. In some embodiments, the pharmaceutical formulation comprises about 0.3 mg to about 1 mg of the glidant. In some embodiments, the pharmaceutical formulation comprises about 0.4 mg to about 5 mg of the glidant. In some embodiments, the pharmaceutical formulation comprises about 0.4 mg to about 4 mg of the glidant. In some embodiments, the pharmaceutical formulation comprises about 0.4 mg to about 3.5 mg of the glidant. In some embodiments, the pharmaceutical formulation comprises about 0.4 mg to about 3 mg of the glidant. In some embodiments, the pharmaceutical formulation comprises about 0.4 mg to about 2.5 mg of the glidant. In some embodiments, the pharmaceutical formulation comprises about 0.4 mg to about 2 mg of the glidant. In some embodiments, the pharmaceutical formulation comprises about 0.4 mg to about 1.5 mg of the glidant. In some embodiments, the pharmaceutical formulation comprises about 0.4 mg to about 1 mg of the glidant. In some embodiments, the pharmaceutical formulation comprises about 0.2 mg of the glidant. In some embodiments, the pharmaceutical formulation comprises about 0.25 mg of the glidant. In some embodiments, the pharmaceutical formulation comprises about 0.3 mg of the glidant. In some embodiments, the pharmaceutical formulation comprises about 0.35 mg of the glidant. In some embodiments, the pharmaceutical formulation comprises about 0.4 mg of the glidant. In some embodiments, the pharmaceutical formulation comprises about 0.45 mg of the glidant. In some embodiments, the pharmaceutical formulation comprises about 0.5 mg of the glidant. In some embodiments, the pharmaceutical formulation comprises about 0.6 mg of the glidant. In some embodiments, the pharmaceutical formulation comprises about 0.7 mg of the glidant. In some embodiments, the pharmaceutical formulation comprises about 0.8 mg of the glidant. In some embodiments, the pharmaceutical formulation comprises about 0.9 mg of the glidant. In some embodiments, the pharmaceutical formulation comprises about 1 mg of the glidant. In some embodiments, the pharmaceutical formulation comprises about 1.1 mg of the glidant. In some embodiments, the pharmaceutical formulation comprises about 1.2 mg of the glidant. In some embodiments, the pharmaceutical formulation comprises about 1.3 mg of the glidant. In some embodiments, the pharmaceutical formulation comprises about 1.4 mg of the glidant. In some embodiments, the pharmaceutical formulation comprises about 1.5 mg of the glidant. In some embodiments, the pharmaceutical formulation comprises about 1.6 mg of the glidant. In some embodiments, the pharmaceutical formulation comprises about 1.7 mg of the glidant. In some embodiments, the pharmaceutical formulation comprises about 1.8 mg of the glidant. In some embodiments, the pharmaceutical formulation comprises about 1.9 mg of the glidant. In some embodiments, the pharmaceutical formulation comprises about 2 mg of the glidant. In some embodiments, the pharmaceutical formulation comprises about 2.25 mg of the glidant. In some embodiments, the pharmaceutical formulation comprises about 2.5 mg of the glidant. In some embodiments, the pharmaceutical formulation comprises about 2.75 mg of the glidant. In some embodiments, the pharmaceutical formulation comprises about 3 mg of the glidant. In some embodiments, the pharmaceutical formulation comprises about 3.5 mg of the glidant. In some embodiments, the pharmaceutical formulation comprises about 4 mg of the glidant. In some embodiments, the pharmaceutical formulation comprises about 4.5 mg of the glidant. In some embodiments, the pharmaceutical formulation comprises about 5 mg of the glidant. In some embodiments, the pharmaceutical formulation comprises about 6 mg of the glidant. In some embodiments, the pharmaceutical formulation comprises about 7 mg of the glidant. In some embodiments, the pharmaceutical formulation comprises about 8 mg of the glidant. In some embodiments, the pharmaceutical formulation comprises about 9 mg of the glidant. In some embodiments, the pharmaceutical formulation comprises about 10 mg of the glidant. In some embodiments, the pharmaceutical formulation comprises about 0.2 mg to about 10 mg of the glidant, wherein the glidant is silicon dioxide. In some embodiments, the pharmaceutical formulation comprises about 0.2 mg to about 5 mg of the glidant, wherein the glidant is silicon dioxide. In some embodiments, the pharmaceutical formulation comprises about 0.2 mg to about 4 mg of the glidant, wherein the glidant is silicon dioxide. In some embodiments, the pharmaceutical formulation comprises about 0.2 mg to about 3 mg of the glidant, wherein the glidant is silicon dioxide. In some embodiments, the pharmaceutical formulation comprises about 0.2 mg to about 2.5 mg of the glidant, wherein the glidant is silicon dioxide. In some embodiments, the pharmaceutical formulation comprises about 0.2 mg to about 2 mg of the glidant, wherein the glidant is silicon dioxide. In some embodiments, the pharmaceutical formulation comprises about 0.4 mg to about 4 mg of the glidant, wherein the glidant is silicon dioxide. In some embodiments, the pharmaceutical formulation comprises about 0.4 mg to about 3 mg of the glidant, wherein the glidant is silicon dioxide. In some embodiments, the pharmaceutical formulation comprises about 0.4 mg to about 2.5 mg of the glidant, wherein the glidant is silicon dioxide. In some embodiments, the pharmaceutical formulation comprises about 0.4 mg to about 2 mg of the glidant, wherein the glidant is silicon dioxide. In some embodiments, the pharmaceutical formulation comprises about 0.2 mg to about 10 mg of the glidant, wherein the glidant is talc. In some embodiments, the pharmaceutical formulation comprises about 0.2 mg to about 5 mg of the glidant, wherein the glidant is talc. In some embodiments, the pharmaceutical formulation comprises about 0.2 mg to about 4 mg of the glidant, wherein the glidant is talc. In some embodiments, the pharmaceutical formulation comprises about 0.2 mg to about 3 mg of the glidant, wherein the glidant is talc. In some embodiments, the pharmaceutical formulation comprises about 0.2 mg to about 2.5 mg of the glidant, wherein the glidant is talc. In some embodiments, the pharmaceutical formulation comprises about 0.2 mg to about 2 mg of the glidant, wherein the glidant is talc. In some embodiments, the pharmaceutical formulation comprises about 0.4 mg to about 4 mg of the glidant, wherein the glidant is talc. In some embodiments, the pharmaceutical formulation comprises about 0.4 mg to about 3 mg of the glidant, wherein the glidant is talc. In some embodiments, the pharmaceutical formulation comprises about 0.4 mg to about 2.5 mg of the glidant, wherein the glidant is talc. In some embodiments, the pharmaceutical formulation comprises about 0.4 mg to about 2 mg of the glidant, wherein the glidant is talc.

In some embodiments, the pharmaceutical formulation further comprises a buffer. In some embodiments, the pharmaceutical formulation further comprises a buffer selected from acetates, carbonates, phosphates, citrates, and glutamates. In some embodiments, the pharmaceutical formulation further comprises an acetate buffer. In some embodiments, the pharmaceutical formulation further comprises a carbonate buffer. In some embodiments, the pharmaceutical formulation further comprises a phosphate buffer. In some embodiments, the pharmaceutical formulation further comprises a citrate buffer. In some embodiments, the pharmaceutical formulation further comprises a glutamate buffer. In some embodiments, the pharmaceutical formulation further comprises a buffer selected from potassium dihydrogen phosphate, sodium bicarbonate, magnesium carbonate, sodium citrate, sodium dihydrogen phosphate, dipotassium monohydrogen phosphate, and disodium monohydrogen phosphate. In some embodiments, the pharmaceutical formulation further comprises a buffer selected from potassium dihydrogen phosphate, sodium bicarbonate, magnesium carbonate, and sodium citrate. In some embodiments, the pharmaceutical formulation further comprises a buffer selected from potassium dihydrogen phosphate, sodium bicarbonate, magnesium carbonate, sodium citrate, sodium dihydrogen phosphate, dipotassium monohydrogen phosphate, and disodium monohydrogen phosphate. In some embodiments, the pharmaceutical formulation further comprises sodium dihydrogen phosphate, dipotassium monohydrogen phosphate, and disodium monohydrogen phosphate. In some embodiments, the pharmaceutical formulation further comprises dipotassium monohydrogen phosphate. In some embodiments, the pharmaceutical formulation further comprises disodium monohydrogen phosphate.

In some embodiments, the pharmaceutical formulation further comprises potassium dihydrogen phosphate. In some embodiments, the pharmaceutical formulation further comprises about 0.1 mg to about 5 mg of potassium dihydrogen phosphate. In some embodiments, the pharmaceutical formulation further comprises about 0.1 mg to about 4.5 mg of potassium dihydrogen phosphate. In some embodiments, the pharmaceutical formulation further comprises about 0.1 mg to about 4 mg of potassium dihydrogen phosphate. In some embodiments, the pharmaceutical formulation further comprises about 0.1 mg to about 3.5 mg of potassium dihydrogen phosphate. In some embodiments, the pharmaceutical formulation further comprises about 0.1 mg to about 3 mg of potassium dihydrogen phosphate. In some embodiments, the pharmaceutical formulation further comprises about 0.1 mg to about 2.5 mg of potassium dihydrogen phosphate. In some embodiments, the pharmaceutical formulation further comprises about 0.1 mg to about 2 mg of potassium dihydrogen phosphate. In some embodiments, the pharmaceutical formulation further comprises about 0.1 mg to about 1.5 mg of potassium dihydrogen phosphate. In some embodiments, the pharmaceutical formulation further comprises about 0.1 mg to about 1 mg of potassium dihydrogen phosphate. In some embodiments, the pharmaceutical formulation further comprises about 0.1 mg to about 0.5 mg of potassium dihydrogen phosphate. In some embodiments, the pharmaceutical formulation further comprises about 0.2 mg to about 4 mg of potassium dihydrogen phosphate. In some embodiments, the pharmaceutical formulation further comprises about 0.2 mg to about 3.5 mg of potassium dihydrogen phosphate. In some embodiments, the pharmaceutical formulation further comprises about 0.2 mg to about 3 mg of potassium dihydrogen phosphate. In some embodiments, the pharmaceutical formulation further comprises about 0.2 mg to about 2.5 mg of potassium dihydrogen phosphate. In some embodiments, the pharmaceutical formulation further comprises about 0.2 mg to about 2 mg of potassium dihydrogen phosphate. In some embodiments, the pharmaceutical formulation further comprises about 0.2 mg to about 1.5 mg of potassium dihydrogen phosphate. In some embodiments, the pharmaceutical formulation further comprises about 0.2 mg to about 1 mg of potassium dihydrogen phosphate. In some embodiments, the pharmaceutical formulation further comprises about 0.2 mg to about 0.5 mg of potassium dihydrogen phosphate. In some embodiments, the pharmaceutical formulation further comprises about 0.1 mg of potassium dihydrogen phosphate. In some embodiments, the pharmaceutical formulation further comprises about 0.15 mg of potassium dihydrogen phosphate. In some embodiments, the pharmaceutical formulation further comprises about 0.2 mg of potassium dihydrogen phosphate. In some embodiments, the pharmaceutical formulation further comprises about 0.25 mg of potassium dihydrogen phosphate. In some embodiments, the pharmaceutical formulation further comprises about 0.3 mg of potassium dihydrogen phosphate. In some embodiments, the pharmaceutical formulation further comprises about 0.35 mg of potassium dihydrogen phosphate. In some embodiments, the pharmaceutical formulation further comprises about 0.4 mg of potassium dihydrogen phosphate. In some embodiments, the pharmaceutical formulation further comprises about 0.45 mg of potassium dihydrogen phosphate. In some embodiments, the pharmaceutical formulation further comprises about 0.5 mg of potassium dihydrogen phosphate. In some embodiments, the pharmaceutical formulation further comprises about 0.55 mg of potassium dihydrogen phosphate. In some embodiments, the pharmaceutical formulation further comprises about 0.6 mg of potassium dihydrogen phosphate. In some embodiments, the pharmaceutical formulation further comprises about 0.65 mg of potassium dihydrogen phosphate. In some embodiments, the pharmaceutical formulation further comprises about 0.7 mg of potassium dihydrogen phosphate. In some embodiments, the pharmaceutical formulation further comprises about 0.75 mg of potassium dihydrogen phosphate. In some embodiments, the pharmaceutical formulation further comprises about 0.8 mg of potassium dihydrogen phosphate. In some embodiments, the pharmaceutical formulation further comprises about 0.85 mg of potassium dihydrogen phosphate. In some embodiments, the pharmaceutical formulation further comprises about 0.9 mg of potassium dihydrogen phosphate. In some embodiments, the pharmaceutical formulation further comprises about 0.95 mg of potassium dihydrogen phosphate. In some embodiments, the pharmaceutical formulation further comprises about 1 mg of potassium dihydrogen phosphate. In some embodiments, the pharmaceutical formulation further comprises about 1.25 mg of potassium dihydrogen phosphate. In some embodiments, the pharmaceutical formulation further comprises about 1.5 mg of potassium dihydrogen phosphate. In some embodiments, the pharmaceutical formulation further comprises about 1.75 mg of potassium dihydrogen phosphate. In some embodiments, the pharmaceutical formulation further comprises about 2 mg of potassium dihydrogen phosphate. In some embodiments, the pharmaceutical formulation further comprises about 2.5 mg of potassium dihydrogen phosphate. In some embodiments, the pharmaceutical formulation further comprises about 3 mg of potassium dihydrogen phosphate. In some embodiments, the pharmaceutical formulation further comprises about 3.5 mg of potassium dihydrogen phosphate. In some embodiments, the pharmaceutical formulation further comprises about 4 mg of potassium dihydrogen phosphate. In some embodiments, the pharmaceutical formulation further comprises about 4.5 mg of potassium dihydrogen phosphate. In some embodiments, the pharmaceutical formulation further comprises about 5 mg of potassium dihydrogen phosphate.

In some embodiments, the pharmaceutical formulation further comprises sodium bicarbonate. In some embodiments, the pharmaceutical formulation further comprises about 0.1 mg to about 5 mg of sodium bicarbonate. In some embodiments, the pharmaceutical formulation further comprises about 0.1 mg to about 4.5 mg of sodium bicarbonate. In some embodiments, the pharmaceutical formulation further comprises about 0.1 mg to about 4 mg of sodium bicarbonate. In some embodiments, the pharmaceutical formulation further comprises about 0.1 mg to about 3.5 mg of sodium bicarbonate. In some embodiments, the pharmaceutical formulation further comprises about 0.1 mg to about 3 mg of sodium bicarbonate. In some embodiments, the pharmaceutical formulation further comprises about 0.1 mg to about 2.5 mg of sodium bicarbonate. In some embodiments, the pharmaceutical formulation further comprises about 0.1 mg to about 2 mg of sodium bicarbonate. In some embodiments, the pharmaceutical formulation further comprises about 0.1 mg to about 1.5 mg of sodium bicarbonate. In some embodiments, the pharmaceutical formulation further comprises about 0.1 mg to about 1 mg of sodium bicarbonate. In some embodiments, the pharmaceutical formulation further comprises about 0.1 mg to about 0.5 mg of sodium bicarbonate. In some embodiments, the pharmaceutical formulation further comprises about 0.2 mg to about 4 mg of sodium bicarbonate. In some embodiments, the pharmaceutical formulation further comprises about 0.2 mg to about 3.5 mg of sodium bicarbonate. In some embodiments, the pharmaceutical formulation further comprises about 0.2 mg to about 3 mg of sodium bicarbonate. In some embodiments, the pharmaceutical formulation further comprises about 0.2 mg to about 2.5 mg of sodium bicarbonate. In some embodiments, the pharmaceutical formulation further comprises about 0.2 mg to about 2 mg of sodium bicarbonate. In some embodiments, the pharmaceutical formulation further comprises about 0.2 mg to about 1.5 mg of sodium bicarbonate. In some embodiments, the pharmaceutical formulation further comprises about 0.2 mg to about 1 mg of sodium bicarbonate. In some embodiments, the pharmaceutical formulation further comprises about 0.2 mg to about 0.5 mg of sodium bicarbonate. In some embodiments, the pharmaceutical formulation further comprises about 0.1 mg of sodium bicarbonate. In some embodiments, the pharmaceutical formulation further comprises about 0.15 mg of sodium bicarbonate. In some embodiments, the pharmaceutical formulation further comprises about 0.2 mg of sodium bicarbonate. In some embodiments, the pharmaceutical formulation further comprises about 0.25 mg of sodium bicarbonate. In some embodiments, the pharmaceutical formulation further comprises about 0.3 mg of sodium bicarbonate. In some embodiments, the pharmaceutical formulation further comprises about 0.35 mg of sodium bicarbonate. In some embodiments, the pharmaceutical formulation further comprises about 0.4 mg of sodium bicarbonate. In some embodiments, the pharmaceutical formulation further comprises about 0.45 mg of sodium bicarbonate. In some embodiments, the pharmaceutical formulation further comprises about 0.5 mg of sodium bicarbonate. In some embodiments, the pharmaceutical formulation further comprises about 0.55 mg of sodium bicarbonate. In some embodiments, the pharmaceutical formulation further comprises about 0.6 mg of sodium bicarbonate. In some embodiments, the pharmaceutical formulation further comprises about 0.65 mg of sodium bicarbonate. In some embodiments, the pharmaceutical formulation further comprises about 0.7 mg of sodium bicarbonate. In some embodiments, the pharmaceutical formulation further comprises about 0.75 mg of sodium bicarbonate. In some embodiments, the pharmaceutical formulation further comprises about 0.8 mg of sodium bicarbonate. In some embodiments, the pharmaceutical formulation further comprises about 0.85 mg of sodium bicarbonate. In some embodiments, the pharmaceutical formulation further comprises about 0.9 mg of sodium bicarbonate. In some embodiments, the pharmaceutical formulation further comprises about 0.95 mg of sodium bicarbonate. In some embodiments, the pharmaceutical formulation further comprises about 1 mg of sodium bicarbonate. In some embodiments, the pharmaceutical formulation further comprises about 1.25 mg of sodium bicarbonate. In some embodiments, the pharmaceutical formulation further comprises about 1.5 mg of sodium bicarbonate. In some embodiments, the pharmaceutical formulation further comprises about 1.75 mg of sodium bicarbonate. In some embodiments, the pharmaceutical formulation further comprises about 2 mg of sodium bicarbonate. In some embodiments, the pharmaceutical formulation further comprises about 2.5 mg of sodium bicarbonate. In some embodiments, the pharmaceutical formulation further comprises about 3 mg of sodium bicarbonate. In some embodiments, the pharmaceutical formulation further comprises about 3.5 mg of sodium bicarbonate. In some embodiments, the pharmaceutical formulation further comprises about 4 mg of sodium bicarbonate. In some embodiments, the pharmaceutical formulation further comprises about 4.5 mg of sodium bicarbonate. In some embodiments, the pharmaceutical formulation further comprises about 5 mg of sodium bicarbonate.

In some embodiments, the pharmaceutical formulation further comprises magnesium carbonate. In some embodiments, the pharmaceutical formulation further comprises about 0.1 mg to about 5 mg of magnesium carbonate. In some embodiments, the pharmaceutical formulation further comprises about 0.1 mg to about 4.5 mg of magnesium carbonate. In some embodiments, the pharmaceutical formulation further comprises about 0.1 mg to about 4 mg of magnesium carbonate. In some embodiments, the pharmaceutical formulation further comprises about 0.1 mg to about 3.5 mg of magnesium carbonate. In some embodiments, the pharmaceutical formulation further comprises about 0.1 mg to about 3 mg of magnesium carbonate. In some embodiments, the pharmaceutical formulation further comprises about 0.1 mg to about 2.5 mg of magnesium carbonate. In some embodiments, the pharmaceutical formulation further comprises about 0.1 mg to about 2 mg of magnesium carbonate. In some embodiments, the pharmaceutical formulation further comprises about 0.1 mg to about 1.5 mg of magnesium carbonate. In some embodiments, the pharmaceutical formulation further comprises about 0.1 mg to about 1 mg of magnesium carbonate. In some embodiments, the pharmaceutical formulation further comprises about 0.1 mg to about 0.5 mg of magnesium carbonate. In some embodiments, the pharmaceutical formulation further comprises about 0.2 mg to about 4 mg of magnesium carbonate. In some embodiments, the pharmaceutical formulation further comprises about 0.2 mg to about 3.5 mg of magnesium carbonate. In some embodiments, the pharmaceutical formulation further comprises about 0.2 mg to about 3 mg of magnesium carbonate. In some embodiments, the pharmaceutical formulation further comprises about 0.2 mg to about 2.5 mg of magnesium carbonate. In some embodiments, the pharmaceutical formulation further comprises about 0.2 mg to about 2 mg of magnesium carbonate. In some embodiments, the pharmaceutical formulation further comprises about 0.2 mg to about 1.5 mg of magnesium carbonate. In some embodiments, the pharmaceutical formulation further comprises about 0.2 mg to about 1 mg of magnesium carbonate. In some embodiments, the pharmaceutical formulation further comprises about 0.2 mg to about 0.5 mg of magnesium carbonate. In some embodiments, the pharmaceutical formulation further comprises about 0.1 mg of magnesium carbonate. In some embodiments, the pharmaceutical formulation further comprises about 0.15 mg of magnesium carbonate. In some embodiments, the pharmaceutical formulation further comprises about 0.2 mg of magnesium carbonate. In some embodiments, the pharmaceutical formulation further comprises about 0.25 mg of magnesium carbonate. In some embodiments, the pharmaceutical formulation further comprises about 0.3 mg of magnesium carbonate. In some embodiments, the pharmaceutical formulation further comprises about 0.35 mg of magnesium carbonate. In some embodiments, the pharmaceutical formulation further comprises about 0.4 mg of magnesium carbonate. In some embodiments, the pharmaceutical formulation further comprises about 0.45 mg of magnesium carbonate. In some embodiments, the pharmaceutical formulation further comprises about 0.5 mg of magnesium carbonate. In some embodiments, the pharmaceutical formulation further comprises about 0.55 mg of magnesium carbonate. In some embodiments, the pharmaceutical formulation further comprises about 0.6 mg of magnesium carbonate. In some embodiments, the pharmaceutical formulation further comprises about 0.65 mg of magnesium carbonate. In some embodiments, the pharmaceutical formulation further comprises about 0.7 mg of magnesium carbonate. In some embodiments, the pharmaceutical formulation further comprises about 0.75 mg of magnesium carbonate. In some embodiments, the pharmaceutical formulation further comprises about 0.8 mg of magnesium carbonate. In some embodiments, the pharmaceutical formulation further comprises about 0.85 mg of magnesium carbonate. In some embodiments, the pharmaceutical formulation further comprises about 0.9 mg of magnesium carbonate. In some embodiments, the pharmaceutical formulation further comprises about 0.95 mg of magnesium carbonate. In some embodiments, the pharmaceutical formulation further comprises about 1 mg of magnesium carbonate. In some embodiments, the pharmaceutical formulation further comprises about 1.25 mg of magnesium carbonate. In some embodiments, the pharmaceutical formulation further comprises about 1.5 mg of magnesium carbonate. In some embodiments, the pharmaceutical formulation further comprises about 1.75 mg of magnesium carbonate. In some embodiments, the pharmaceutical formulation further comprises about 2 mg of magnesium carbonate. In some embodiments, the pharmaceutical formulation further comprises about 2.5 mg of magnesium carbonate. In some embodiments, the pharmaceutical formulation further comprises about 3 mg of magnesium carbonate. In some embodiments, the pharmaceutical formulation further comprises about 3.5 mg of magnesium carbonate. In some embodiments, the pharmaceutical formulation further comprises about 4 mg of magnesium carbonate. In some embodiments, the pharmaceutical formulation further comprises about 4.5 mg of magnesium carbonate. In some embodiments, the pharmaceutical formulation further comprises about 5 mg of magnesium carbonate.

In some embodiments, the pharmaceutical formulation further comprises sodium citrate. In some embodiments, the pharmaceutical formulation further comprises about 0.1 mg to about 5 mg of sodium citrate. In some embodiments, the pharmaceutical formulation further comprises about 0.1 mg to about 4.5 mg of sodium citrate. In some embodiments, the pharmaceutical formulation further comprises about 0.1 mg to about 4 mg of sodium citrate. In some embodiments, the pharmaceutical formulation further comprises about 0.1 mg to about 3.5 mg of sodium citrate. In some embodiments, the pharmaceutical formulation further comprises about 0.1 mg to about 3 mg of sodium citrate. In some embodiments, the pharmaceutical formulation further comprises about 0.1 mg to about 2.5 mg of sodium citrate. In some embodiments, the pharmaceutical formulation further comprises about 0.1 mg to about 2 mg of sodium citrate. In some embodiments, the pharmaceutical formulation further comprises about 0.1 mg to about 1.5 mg of sodium citrate. In some embodiments, the pharmaceutical formulation further comprises about 0.1 mg to about 1 mg of sodium citrate. In some embodiments, the pharmaceutical formulation further comprises about 0.1 mg to about 0.5 mg of sodium citrate. In some embodiments, the pharmaceutical formulation further comprises about 0.2 mg to about 4 mg of sodium citrate. In some embodiments, the pharmaceutical formulation further comprises about 0.2 mg to about 3.5 mg of sodium citrate. In some embodiments, the pharmaceutical formulation further comprises about 0.2 mg to about 3 mg of sodium citrate. In some embodiments, the pharmaceutical formulation further comprises about 0.2 mg to about 2.5 mg of sodium citrate. In some embodiments, the pharmaceutical formulation further comprises about 0.2 mg to about 2 mg of sodium citrate. In some embodiments, the pharmaceutical formulation further comprises about 0.2 mg to about 1.5 mg of sodium citrate. In some embodiments, the pharmaceutical formulation further comprises about 0.2 mg to about 1 mg of sodium citrate. In some embodiments, the pharmaceutical formulation further comprises about 0.2 mg to about 0.5 mg of sodium citrate. In some embodiments, the pharmaceutical formulation further comprises about 0.1 mg of sodium citrate. In some embodiments, the pharmaceutical formulation further comprises about 0.15 mg of sodium citrate. In some embodiments, the pharmaceutical formulation further comprises about 0.2 mg of sodium citrate. In some embodiments, the pharmaceutical formulation further comprises about 0.25 mg of sodium citrate. In some embodiments, the pharmaceutical formulation further comprises about 0.3 mg of sodium citrate. In some embodiments, the pharmaceutical formulation further comprises about 0.35 mg of sodium citrate. In some embodiments, the pharmaceutical formulation further comprises about 0.4 mg of sodium citrate. In some embodiments, the pharmaceutical formulation further comprises about 0.45 mg of sodium citrate. In some embodiments, the pharmaceutical formulation further comprises about 0.5 mg of sodium citrate. In some embodiments, the pharmaceutical formulation further comprises about 0.55 mg of sodium citrate. In some embodiments, the pharmaceutical formulation further comprises about 0.6 mg of sodium citrate. In some embodiments, the pharmaceutical formulation further comprises about 0.65 mg of sodium citrate. In some embodiments, the pharmaceutical formulation further comprises about 0.7 mg of sodium citrate. In some embodiments, the pharmaceutical formulation further comprises about 0.75 mg of sodium citrate. In some embodiments, the pharmaceutical formulation further comprises about 0.8 mg of sodium citrate. In some embodiments, the pharmaceutical formulation further comprises about 0.85 mg of sodium citrate. In some embodiments, the pharmaceutical formulation further comprises about 0.9 mg of sodium citrate. In some embodiments, the pharmaceutical formulation further comprises about 0.95 mg of sodium citrate. In some embodiments, the pharmaceutical formulation further comprises about 1 mg of sodium citrate. In some embodiments, the pharmaceutical formulation further comprises about 1.25 mg of sodium citrate. In some embodiments, the pharmaceutical formulation further comprises about 1.5 mg of sodium citrate. In some embodiments, the pharmaceutical formulation further comprises about 1.75 mg of sodium citrate. In some embodiments, the pharmaceutical formulation further comprises about 2 mg of sodium citrate. In some embodiments, the pharmaceutical formulation further comprises about 2.5 mg of sodium citrate. In some embodiments, the pharmaceutical formulation further comprises about 3 mg of sodium citrate. In some embodiments, the pharmaceutical formulation further comprises about 3.5 mg of sodium citrate. In some embodiments, the pharmaceutical formulation further comprises about 4 mg of sodium citrate. In some embodiments, the pharmaceutical formulation further comprises about 4.5 mg of sodium citrate. In some embodiments, the pharmaceutical formulation further comprises about 5 mg of sodium citrate.

In some embodiments, the pharmaceutical formulation further comprises a plasticizer. In some embodiments, the plasticizer is selected from PEG 400, triethyl citrate, triacetin, acetyl tributyl citrate, acetyl triethyl citrate, stearic acid, glycerin, polyethylene glycols, polyethylene glycol monomethyl ether, propylene glycol, sorbitol sorbitan solution, castor oil, diacetylated monoglycerides, dibutyl sebacates, and diethyl phthalate. In some embodiments, the pharmaceutical formulation further comprises a plasticizer, wherein the plasticizer is PEG 400. In some embodiments, the pharmaceutical formulation further comprises a plasticizer, wherein the plasticizer is triethyl citrate. In some embodiments, the pharmaceutical formulation further comprises a plasticizer, wherein the plasticizer is triacetin. In some embodiments, the pharmaceutical formulation further comprises a plasticizer, wherein the plasticizer is acetyl tributyl citrate. In some embodiments, the pharmaceutical formulation further comprises a plasticizer, wherein the plasticizer is acetyl triethyl citrate. In some embodiments, the pharmaceutical formulation further comprises a plasticizer, wherein the plasticizer is stearic acid. In some embodiments, the pharmaceutical formulation further comprises a plasticizer, wherein the plasticizer is glycerin. In some embodiments, the pharmaceutical formulation further comprises a plasticizer, wherein the plasticizer is a polyethylene glycol. In some embodiments, the pharmaceutical formulation further comprises a plasticizer, wherein the plasticizer is polyethylene glycol monomethyl ether. In some embodiments, the pharmaceutical formulation further comprises a plasticizer, wherein the plasticizer is propylene glycol. In some embodiments, the pharmaceutical formulation further comprises a plasticizer, wherein the plasticizer is sorbitol sorbitan solution. In some embodiments, the pharmaceutical formulation further comprises a plasticizer, wherein the plasticizer is castor oil. In some embodiments, the pharmaceutical formulation further comprises a plasticizer, wherein the plasticizer is diacetylated monoglycerides. In some embodiments, the pharmaceutical formulation further comprises a plasticizer, wherein the plasticizer is dibutyl sebacates. In some embodiments, the pharmaceutical formulation further comprises a plasticizer, wherein the plasticizer is diethyl phthalate. In some embodiments, the pharmaceutical formulation further comprises about 1 mg to about 65 mg of a plasticizer. In some embodiments, the pharmaceutical formulation further comprises about 1 mg to about 60 mg of a plasticizer. In some embodiments, the pharmaceutical formulation further comprises about 1 mg to about 55 mg of a plasticizer. In some embodiments, the pharmaceutical formulation further comprises about 1 mg to about 50 mg of a plasticizer. In some embodiments, the pharmaceutical formulation further comprises about 1 mg to about 45 mg of a plasticizer. In some embodiments, the pharmaceutical formulation further comprises about 1 mg to about 40 mg of a plasticizer. In some embodiments, the pharmaceutical formulation further comprises about 1 mg to about 35 mg of a plasticizer. In some embodiments, the pharmaceutical formulation further comprises about 1 mg to about 30 mg of a plasticizer. In some embodiments, the pharmaceutical formulation further comprises about 1 mg to about 25 mg of a plasticizer. In some embodiments, the pharmaceutical formulation further comprises about 1 mg to about 20 mg of a plasticizer. In some embodiments, the pharmaceutical formulation further comprises about 1 mg to about 15 mg of a plasticizer. In some embodiments, the pharmaceutical formulation further comprises about 1 mg to about 10 mg of a plasticizer. In some embodiments, the pharmaceutical formulation further comprises about 2 mg to about 30 mg of a plasticizer. In some embodiments, the pharmaceutical formulation further comprises about 2 mg to about 25 mg of a plasticizer. In some embodiments, the pharmaceutical formulation further comprises about 2 mg to about 20 mg of a plasticizer. In some embodiments, the pharmaceutical formulation further comprises about 2 mg to about 15 mg of a plasticizer. In some embodiments, the pharmaceutical formulation further comprises about 2 mg to about 10 mg of a plasticizer. In some embodiments, the pharmaceutical formulation further comprises about 1 mg of a plasticizer. In some embodiments, the pharmaceutical formulation further comprises about 1.5 mg of a plasticizer. In some embodiments, the pharmaceutical formulation further comprises about 2 mg of a plasticizer. In some embodiments, the pharmaceutical formulation further comprises about 2.5 mg of a plasticizer. In some embodiments, the pharmaceutical formulation further comprises about 3 mg of a plasticizer. In some embodiments, the pharmaceutical formulation further comprises about 3.5 mg of a plasticizer. In some embodiments, the pharmaceutical formulation further comprises about 4 mg of a plasticizer. In some embodiments, the pharmaceutical formulation further comprises about 4.5 mg of a plasticizer. In some embodiments, the pharmaceutical formulation further comprises about 5 mg of a plasticizer. In some embodiments, the pharmaceutical formulation further comprises about 5.5 mg of a plasticizer. In some embodiments, the pharmaceutical formulation further comprises about 6 mg of a plasticizer. In some embodiments, the pharmaceutical formulation further comprises about 6.5 mg of a plasticizer. In some embodiments, the pharmaceutical formulation further comprises about 7 mg of a plasticizer. In some embodiments, the pharmaceutical formulation further comprises about 7.5 mg of a plasticizer. In some embodiments, the pharmaceutical formulation further comprises about 8 mg of a plasticizer. In some embodiments, the pharmaceutical formulation further comprises about 8.5 mg of a plasticizer. In some embodiments, the pharmaceutical formulation further comprises about 9 mg of a plasticizer. In some embodiments, the pharmaceutical formulation further comprises about 10 mg of a plasticizer. In some embodiments, the pharmaceutical formulation further comprises about 11 mg of a plasticizer. In some embodiments, the pharmaceutical formulation further comprises about 12 mg of a plasticizer. In some embodiments, the pharmaceutical formulation further comprises about 13 mg of a plasticizer. In some embodiments, the pharmaceutical formulation further comprises about 14 mg of a plasticizer. In some embodiments, the pharmaceutical formulation further comprises about 15 mg of a plasticizer. In some embodiments, the pharmaceutical formulation further comprises about 1 mg to about 65 mg of a plasticizer, wherein the plasticizer is PEG 400. In some embodiments, the pharmaceutical formulation further comprises about 1 mg to about 60 mg of a plasticizer, wherein the plasticizer is PEG 400. In some embodiments, the pharmaceutical formulation further comprises about 1 mg to about 55 mg of a plasticizer, wherein the plasticizer is PEG 400. In some embodiments, the pharmaceutical formulation further comprises about 1 mg to about 50 mg of a plasticizer, wherein the plasticizer is PEG 400. In some embodiments, the pharmaceutical formulation further comprises about 1 mg to about 45 mg of a plasticizer, wherein the plasticizer is PEG 400. In some embodiments, the pharmaceutical formulation further comprises about 1 mg to about 40 mg of a plasticizer, wherein the plasticizer is PEG 400. In some embodiments, the pharmaceutical formulation further comprises about 1 mg to about 35 mg of a plasticizer, wherein the plasticizer is PEG 400. In some embodiments, the pharmaceutical formulation further comprises about 1 mg to about 30 mg of a plasticizer, wherein the plasticizer is PEG 400. In some embodiments, the pharmaceutical formulation further comprises about 1 mg to about 25 mg of a plasticizer, wherein the plasticizer is PEG 400. In some embodiments, the pharmaceutical formulation further comprises about 1 mg to about 20 mg of a plasticizer, wherein the plasticizer is PEG 400. In some embodiments, the pharmaceutical formulation further comprises about 1 mg to about 15 mg of a plasticizer, wherein the plasticizer is PEG 400. In some embodiments, the pharmaceutical formulation further comprises about 1 mg to about 10 mg of a plasticizer, wherein the plasticizer is PEG 400. In some embodiments, the pharmaceutical formulation further comprises about 2 mg to about 30 mg of a plasticizer, wherein the plasticizer is PEG 400. In some embodiments, the pharmaceutical formulation further comprises about 2 mg to about 25 mg of a plasticizer, wherein the plasticizer is PEG 400. In some embodiments, the pharmaceutical formulation further comprises about 2 mg to about 20 mg of a plasticizer, wherein the plasticizer is PEG 400. In some embodiments, the pharmaceutical formulation further comprises about 2 mg to about 15 mg of a plasticizer, wherein the plasticizer is PEG 400. In some embodiments, the pharmaceutical formulation further comprises about 2 mg to about 10 mg of a plasticizer, wherein the plasticizer is PEG 400.

In some embodiments, the pharmaceutical formulation further comprises a filler. In some embodiments, the filler is selected from lactose, mannitol, dicalcium phosphate, microcrystalline cellulose, silicified microcrystalline cellulose, starch, and pregelatinized starch (Starch 1500). In some embodiments, the filler is lactose. In some embodiments, the filler is mannitol. In some embodiments, the filler is dicalcium phosphate. In some embodiments, the filler is microcrystalline cellulose. In some embodiments, the filler is silicified microcrystalline cellulose. In some embodiments, the filler is starch. In some embodiments, the filler is pregelatinized starch (Starch 1500). In some embodiments, the pharmaceutical formulation further comprises about 15 mg to about 850 mg of a filler. In some embodiments, the pharmaceutical formulation further comprises about 15 mg to about 800 mg of a filler. In some embodiments, the pharmaceutical formulation further comprises about 15 mg to about 750 mg of a filler. In some embodiments, the pharmaceutical formulation further comprises about 15 mg to about 700 mg of a filler. In some embodiments, the pharmaceutical formulation further comprises about 15 mg to about 650 mg of a filler. In some embodiments, the pharmaceutical formulation further comprises about 15 mg to about 600 mg of a filler. In some embodiments, the pharmaceutical formulation further comprises about 15 mg to about 550 mg of a filler. In some embodiments, the pharmaceutical formulation further comprises about 15 mg to about 500 mg of a filler. In some embodiments, the pharmaceutical formulation further comprises about 15 mg to about 450 mg of a filler. In some embodiments, the pharmaceutical formulation further comprises about 15 mg to about 400 mg of a filler. In some embodiments, the pharmaceutical formulation further comprises about 20 mg to about 400 mg of a filler. In some embodiments, the pharmaceutical formulation further comprises about 20 mg to about 350 mg of a filler. In some embodiments, the pharmaceutical formulation further comprises about 20 mg to about 300 mg of a filler. In some embodiments, the pharmaceutical formulation further comprises about 20 mg to about 275 mg of a filler. In some embodiments, the pharmaceutical formulation further comprises about 20 mg to about 250 mg of a filler. In some embodiments, the pharmaceutical formulation further comprises about 20 mg to about 225 mg of a filler. In some embodiments, the pharmaceutical formulation further comprises about 20 mg to about 200 mg of a filler. In some embodiments, the pharmaceutical formulation further comprises about 25 mg to about 300 mg of a filler. In some embodiments, the pharmaceutical formulation further comprises about 25 mg to about 275 mg of a filler. In some embodiments, the pharmaceutical formulation further comprises about 25 mg to about 250 mg of a filler. In some embodiments, the pharmaceutical formulation further comprises about 25 mg to about 225 mg of a filler. In some embodiments, the pharmaceutical formulation further comprises about 25 mg to about 200 mg of a filler. In some embodiments, the filler is selected from lactose, mannitol, dicalcium phosphate, microcrystalline cellulose, silicified microcrystalline cellulose, starch, and pregelatinized starch (Starch 1500). In some embodiments, the pharmaceutical formulation further comprises about 30 mg to about 300 mg of a filler. In some embodiments, the pharmaceutical formulation further comprises about 30 mg to about 275 mg of a filler. In some embodiments, the pharmaceutical formulation further comprises about 30 mg to about 250 mg of a filler. In some embodiments, the pharmaceutical formulation further comprises about 30 mg to about 225 mg of a filler. In some embodiments, the pharmaceutical formulation further comprises about 30 mg to about 200 mg of a filler. In some embodiments, the pharmaceutical formulation further comprises about 30 mg to about 175 mg of a filler. In some embodiments, the pharmaceutical formulation further comprises about 30 mg to about 150 mg of a filler. In some embodiments, the pharmaceutical formulation further comprises about 30 mg of a filler. In some embodiments, the pharmaceutical formulation further comprises about 35 mg of a filler. In some embodiments, the pharmaceutical formulation further comprises about 40 mg of a filler. In some embodiments, the pharmaceutical formulation further comprises about 45 mg of a filler. In some embodiments, the pharmaceutical formulation further comprises about 50 mg of a filler. In some embodiments, the pharmaceutical formulation further comprises about 55 mg of a filler. In some embodiments, the pharmaceutical formulation further comprises about 60 mg of a filler. In some embodiments, the pharmaceutical formulation further comprises about 65 mg of a filler. In some embodiments, the pharmaceutical formulation further comprises about 70 mg of a filler. In some embodiments, the pharmaceutical formulation further comprises about 75 mg of a filler. In some embodiments, the pharmaceutical formulation further comprises about 80 mg of a filler. In some embodiments, the pharmaceutical formulation further comprises about 85 mg of a filler. In some embodiments, the pharmaceutical formulation further comprises about 90 mg of a filler. In some embodiments, the pharmaceutical formulation further comprises about 95 mg of a filler. In some embodiments, the pharmaceutical formulation further comprises about 100 mg of a filler. In some embodiments, the pharmaceutical formulation further comprises about 105 mg of a filler. In some embodiments, the pharmaceutical formulation further comprises about 110 mg of a filler. In some embodiments, the pharmaceutical formulation further comprises about 115 mg of a filler. In some embodiments, the pharmaceutical formulation further comprises about 120 mg of a filler. In some embodiments, the pharmaceutical formulation further comprises about 125 mg of a filler. In some embodiments, the pharmaceutical formulation further comprises about 130 mg of a filler. In some embodiments, the pharmaceutical formulation further comprises about 135 mg of a filler. In some embodiments, the pharmaceutical formulation further comprises about 140 mg of a filler. In some embodiments, the pharmaceutical formulation further comprises about 145 mg of a filler. In some embodiments, the pharmaceutical formulation further comprises about 150 mg of a filler. In some embodiments, the pharmaceutical formulation further comprises about 155 mg of a filler. In some embodiments, the pharmaceutical formulation further comprises about 160 mg of a filler. In some embodiments, the pharmaceutical formulation further comprises about 165 mg of a filler. In some embodiments, the pharmaceutical formulation further comprises about 170 mg of a filler. In some embodiments, the pharmaceutical formulation further comprises about 175 mg of a filler. In some embodiments, the pharmaceutical formulation further comprises about 180 mg of a filler. In some embodiments, the pharmaceutical formulation further comprises about 185 mg of a filler. In some embodiments, the pharmaceutical formulation further comprises about 190 mg of a filler. In some embodiments, the pharmaceutical formulation further comprises about 195 mg of a filler. In some embodiments, the pharmaceutical formulation further comprises about 200 mg of a filler.

In some embodiments, the pharmaceutical formulation further comprises a disintegrant. In some embodiments, the disintegrant is selected from corn starch, potato starch, microcrystalline cellulose, methylcellulose, croscarmellose sodium, sodium starch glycolate, povidone, crospovidone, hypromellose, hydroxypropyl cellulose, polyvinyl alcohol, alginic acid, sodium alginate, agar, guar, locust bean, Karaya, pectin, tragacanth, bentonite, citrus pulp, and sodium lauryl sulfate. In some embodiments, the disintegrant is selected from povidone, crospovidone, hypromellose, croscarmellose sodium, hydroxypropyl cellulose, and polyvinyl alcohol. In some embodiments, the disintegrant is polyvinyl alcohol. In some embodiments, the disintegrant is hydroxypropyl cellulose. In some embodiments, the disintegrant is hypromellose. In some embodiments, the disintegrant is povidone. In some embodiments, the disintegrant is crospovidone. In some embodiments, the disintegrant is croscarmellose sodium. In some embodiments, the pharmaceutical formulation further comprises about 3 mg to about 150 mg of the disintegrant. In some embodiments, the pharmaceutical formulation further comprises about 3 mg to about 125 mg of the disintegrant. In some embodiments, the pharmaceutical formulation further comprises about 3 mg to about 100 mg of the disintegrant. In some embodiments, the pharmaceutical formulation further comprises about 3 mg to about 75 mg of the disintegrant. In some embodiments, the pharmaceutical formulation further comprises about 3 mg to about 60 mg of the disintegrant. In some embodiments, the pharmaceutical formulation further comprises about 3 mg to about 50 mg of the disintegrant. In some embodiments, the pharmaceutical formulation further comprises about 4 mg to about 60 mg of the disintegrant. In some embodiments, the pharmaceutical formulation further comprises about 4 mg to about 55 mg of the disintegrant. In some embodiments, the pharmaceutical formulation further comprises about 4 mg to about 50 mg of the disintegrant. In some embodiments, the pharmaceutical formulation further comprises about 5 mg to about 50 mg of the disintegrant. In some embodiments, the pharmaceutical formulation further comprises about 5 mg to about 45 mg of the disintegrant. In some embodiments, the pharmaceutical formulation further comprises about 5 mg to about 40 mg of the disintegrant. In some embodiments, the pharmaceutical formulation further comprises about 5 mg to about 35 mg of the disintegrant. In some embodiments, the pharmaceutical formulation further comprises about 5 mg to about 30 mg of the disintegrant. In some embodiments, the pharmaceutical formulation further comprises about 6 mg to about 30 mg of the disintegrant. In some embodiments, the pharmaceutical formulation further comprises about 5 mg of the disintegrant. In some embodiments, the pharmaceutical formulation further comprises about 6 mg of the disintegrant. In some embodiments, the pharmaceutical formulation further comprises about 7 mg of the disintegrant. In some embodiments, the pharmaceutical formulation further comprises about 8 mg of the disintegrant. In some embodiments, the pharmaceutical formulation further comprises about 9 mg of the disintegrant. In some embodiments, the pharmaceutical formulation further comprises about 10 mg of the disintegrant. In some embodiments, the pharmaceutical formulation further comprises about 12 mg of the disintegrant. In some embodiments, the pharmaceutical formulation further comprises about 15 mg of the disintegrant. In some embodiments, the pharmaceutical formulation further comprises about 20 mg of the disintegrant. In some embodiments, the pharmaceutical formulation further comprises about 25 mg of the disintegrant. In some embodiments, the pharmaceutical formulation further comprises about 30 mg of the disintegrant. In some embodiments, the pharmaceutical formulation further comprises about 35 mg of the disintegrant. In some embodiments, the pharmaceutical formulation further comprises about 40 mg of the disintegrant. In some embodiments, the pharmaceutical formulation further comprises about 3 mg to about 150 mg of the disintegrant, wherein the disintegrant is crospovidone. In some embodiments, the pharmaceutical formulation further comprises about 3 mg to about 100 mg of the disintegrant, wherein the disintegrant is crospovidone. In some embodiments, the pharmaceutical formulation further comprises about 3 mg to about 75 mg of the disintegrant, wherein the disintegrant is crospovidone. In some embodiments, the pharmaceutical formulation further comprises about 3 mg to about 60 mg of the disintegrant, wherein the disintegrant is crospovidone. In some embodiments, the pharmaceutical formulation further comprises about 5 mg to about 50 mg of the disintegrant, wherein the disintegrant is crospovidone. In some embodiments, the pharmaceutical formulation further comprises about 5 mg to about 40 mg of the disintegrant, wherein the disintegrant is crospovidone. In some embodiments, the pharmaceutical formulation further comprises about 5 mg to about 35 mg of the disintegrant, wherein the disintegrant is crospovidone. In some embodiments, the pharmaceutical formulation further comprises about 5 mg to about 30 mg of the disintegrant, wherein the disintegrant is crospovidone. In some embodiments, the pharmaceutical formulation further comprises about 5 mg to about 30 mg of the disintegrant, wherein the disintegrant is crospovidone. In some embodiments, the pharmaceutical formulation further comprises about 3 mg to about 100 mg of the disintegrant, wherein the disintegrant is croscarmellose sodium. In some embodiments, the pharmaceutical formulation further comprises about 3 mg to about 75 mg of the disintegrant, wherein the disintegrant is croscarmellose sodium. In some embodiments, the pharmaceutical formulation further comprises about 3 mg to about 60 mg of the disintegrant, wherein the disintegrant is croscarmellose sodium. In some embodiments, the pharmaceutical formulation further comprises about 5 mg to about 50 mg of the disintegrant, wherein the disintegrant is croscarmellose sodium. In some embodiments, the pharmaceutical formulation further comprises about 5 mg to about 40 mg of the disintegrant, wherein the disintegrant is croscarmellose sodium. In some embodiments, the pharmaceutical formulation further comprises about 5 mg to about 35 mg of the disintegrant, wherein the disintegrant is croscarmellose sodium. In some embodiments, the pharmaceutical formulation further comprises about 5 mg to about 30 mg of the disintegrant, wherein the disintegrant is croscarmellose sodium. In some embodiments, the pharmaceutical formulation further comprises about 5 mg to about 30 mg of the disintegrant, wherein the disintegrant is croscarmellose sodium.

In some embodiments, the pharmaceutical formulation further comprises a lubricant. In some embodiments, the lubricant is selected from magnesium stearate, stearic acid, and sodium stearyl fumarate. In some embodiments, the lubricant is stearic acid. In some embodiments, the lubricant is sodium stearyl fumarate. In some embodiments, the lubricant is magnesium stearate. In some embodiments, the pharmaceutical formulation further comprises about 0.1 mg to about 10 mg of the lubricant. In some embodiments, the pharmaceutical formulation further comprises about 0.1 mg to about 8 mg of the lubricant. In some embodiments, the pharmaceutical formulation further comprises about 0.1 mg to about 6 mg of the lubricant. In some embodiments, the pharmaceutical formulation further comprises about 0.1 mg to about 5 mg of the lubricant. In some embodiments, the pharmaceutical formulation further comprises about 0.1 mg to about 4 mg of the lubricant. In some embodiments, the pharmaceutical formulation further comprises about 0.2 mg to about 10 mg of the lubricant. In some embodiments, the pharmaceutical formulation further comprises about 0.2 mg to about 8 mg of the lubricant. In some embodiments, the pharmaceutical formulation further comprises about 0.2 mg to about 7 mg of the lubricant. In some embodiments, the pharmaceutical formulation further comprises about 0.2 mg to about 6 mg of the lubricant. In some embodiments, the pharmaceutical formulation further comprises about 0.2 mg to about 5 mg of the lubricant. In some embodiments, the pharmaceutical formulation further comprises about 0.2 mg to about 4 mg of the lubricant. In some embodiments, the pharmaceutical formulation further comprises about 0.2 mg to about 3.5 mg of the lubricant. In some embodiments, the pharmaceutical formulation further comprises about 0.2 mg to about 3 mg of the lubricant. In some embodiments, the pharmaceutical formulation further comprises about 0.2 mg to about 2.5 mg of the lubricant. In some embodiments, the pharmaceutical formulation further comprises about 0.2 mg to about 2 mg of the lubricant. In some embodiments, the pharmaceutical formulation further comprises about 0.2 mg to about 1.5 mg of the lubricant. In some embodiments, the pharmaceutical formulation further comprises about 0.3 mg to about 3 mg of the lubricant. In some embodiments, the pharmaceutical formulation further comprises about 0.3 mg to about 2.5 mg of the lubricant. In some embodiments, the pharmaceutical formulation further comprises about 0.3 mg to about 2 mg of the lubricant. In some embodiments, the pharmaceutical formulation further comprises about 0.3 mg to about 1.5 mg of the lubricant. In some embodiments, the pharmaceutical formulation further comprises about 0.3 mg to about 1 mg of the lubricant. In some embodiments, the pharmaceutical formulation further comprises about 0.1 mg of the lubricant. In some embodiments, the pharmaceutical formulation further comprises about 0.15 mg of the lubricant. In some embodiments, the pharmaceutical formulation further comprises about 0.2 mg of the lubricant. In some embodiments, the pharmaceutical formulation further comprises about 0.25 mg of the lubricant. In some embodiments, the pharmaceutical formulation further comprises about 0.3 mg of the lubricant. In some embodiments, the pharmaceutical formulation further comprises about 0.35 mg of the lubricant. In some embodiments, the pharmaceutical formulation further comprises about 0.4 mg of the lubricant. In some embodiments, the pharmaceutical formulation further comprises about 0.45 mg of the lubricant. In some embodiments, the pharmaceutical formulation further comprises about 0.5 mg of the lubricant. In some embodiments, the pharmaceutical formulation further comprises about 0.6 mg of the lubricant. In some embodiments, the pharmaceutical formulation further comprises about 0.7 mg of the lubricant. In some embodiments, the pharmaceutical formulation further comprises about 0.8 mg of the lubricant. In some embodiments, the pharmaceutical formulation further comprises about 0.9 mg of the lubricant. In some embodiments, the pharmaceutical formulation further comprises about 1 mg of the lubricant. In some embodiments, the pharmaceutical formulation further comprises about 1.1 mg of the lubricant. In some embodiments, the pharmaceutical formulation further comprises about 1.2 mg of the lubricant. In some embodiments, the pharmaceutical formulation further comprises about 1.3 mg of the lubricant. In some embodiments, the pharmaceutical formulation further comprises about 1.4 mg of the lubricant. In some embodiments, the pharmaceutical formulation further comprises about 1.5 mg of the lubricant. In some embodiments, the pharmaceutical formulation further comprises about 1.6 mg of the lubricant. In some embodiments, the pharmaceutical formulation further comprises about 1.7 mg of the lubricant. In some embodiments, the pharmaceutical formulation further comprises about 1.8 mg of the lubricant. In some embodiments, the pharmaceutical formulation further comprises about 1.9 mg of the lubricant. In some embodiments, the pharmaceutical formulation further comprises about 2 mg of the lubricant. In some embodiments, the pharmaceutical formulation further comprises about 2.5 mg of the lubricant. In some embodiments, the pharmaceutical formulation further comprises about 3 mg of the lubricant. In some embodiments, the pharmaceutical formulation further comprises about 4 mg of the lubricant. In some embodiments, the pharmaceutical formulation further comprises about 5 mg of the lubricant. In some embodiments, the pharmaceutical formulation further comprises about 6 mg of the lubricant. In some embodiments, the pharmaceutical formulation further comprises about 7 mg of the lubricant. In some embodiments, the pharmaceutical formulation further comprises about 8 mg of the lubricant. In some embodiments, the pharmaceutical formulation further comprises about 9 mg of the lubricant. In some embodiments, the pharmaceutical formulation further comprises about 10 mg of the lubricant. In some embodiments, the pharmaceutical formulation further comprises about 0.2 mg to about 10 mg of the lubricant, wherein the lubricant is sodium stearyl fumarate. In some embodiments, the pharmaceutical formulation further comprises about 0.2 mg to about 5 mg of the lubricant, wherein the lubricant is sodium stearyl fumarate. In some embodiments, the pharmaceutical formulation further comprises about 0.2 mg to about 4 mg of the lubricant, wherein the lubricant is sodium stearyl fumarate. In some embodiments, the pharmaceutical formulation further comprises about 0.2 mg to about 3 mg of the lubricant, wherein the lubricant is sodium stearyl fumarate. In some embodiments, the pharmaceutical formulation further comprises about 0.2 mg to about 2.5 mg of the lubricant, wherein the lubricant is sodium stearyl fumarate. In some embodiments, the pharmaceutical formulation further comprises about 0.2 mg to about 2 mg of the lubricant, wherein the lubricant is sodium stearyl fumarate. In some embodiments, the pharmaceutical formulation further comprises about 0.2 mg to about 1.5 mg of the lubricant, wherein the lubricant is sodium stearyl fumarate. In some embodiments, the pharmaceutical formulation further comprises about 0.2 mg to about 1 mg of the lubricant, wherein the lubricant is sodium stearyl fumarate. In some embodiments, the pharmaceutical formulation further comprises about 0.3 mg to about 4 mg of the lubricant, wherein the lubricant is sodium stearyl fumarate. In some embodiments, the pharmaceutical formulation further comprises about 0.3 mg to about 3 mg of the lubricant, wherein the lubricant is sodium stearyl fumarate. In some embodiments, the pharmaceutical formulation further comprises about 0.3 mg to about 2.5 mg of the lubricant, wherein the lubricant is sodium stearyl fumarate. In some embodiments, the pharmaceutical formulation further comprises about 0.3 mg to about 2 mg of the lubricant, wherein the lubricant is sodium stearyl fumarate. In some embodiments, the pharmaceutical formulation further comprises about 0.3 mg to about 1.5 mg of the lubricant, wherein the lubricant is sodium stearyl fumarate. In some embodiments, the pharmaceutical formulation further comprises about 0.3 mg to about 1 mg of the lubricant, wherein the lubricant is sodium stearyl fumarate. In some embodiments, the pharmaceutical formulation further comprises about 0.2 mg to about 10 mg of the lubricant, wherein the lubricant is magnesium stearate. In some embodiments, the pharmaceutical formulation further comprises about 0.2 mg to about 5 mg of the lubricant, wherein the lubricant is magnesium stearate. In some embodiments, the pharmaceutical formulation further comprises about 0.2 mg to about 4 mg of the lubricant, wherein the lubricant is magnesium stearate. In some embodiments, the pharmaceutical formulation further comprises about 0.2 mg to about 3 mg of the lubricant, wherein the lubricant is magnesium stearate. In some embodiments, the pharmaceutical formulation further comprises about 0.2 mg to about 2.5 mg of the lubricant, wherein the lubricant is magnesium stearate. In some embodiments, the pharmaceutical formulation further comprises about 0.2 mg to about 2 mg of the lubricant, wherein the lubricant is magnesium stearate. In some embodiments, the pharmaceutical formulation further comprises about 0.2 mg to about 1.5 mg of the lubricant, wherein the lubricant is magnesium stearate. In some embodiments, the pharmaceutical formulation further comprises about 0.2 mg to about 1 mg of the lubricant, wherein the lubricant is magnesium stearate. In some embodiments, the pharmaceutical formulation further comprises about 0.3 mg to about 4 mg of the lubricant, wherein the lubricant is magnesium stearate. In some embodiments, the pharmaceutical formulation further comprises about 0.3 mg to about 3 mg of the lubricant, wherein the lubricant is magnesium stearate. In some embodiments, the pharmaceutical formulation further comprises about 0.3 mg to about 2.5 mg of the lubricant, wherein the lubricant is magnesium stearate. In some embodiments, the pharmaceutical formulation further comprises about 0.3 mg to about 2 mg of the lubricant, wherein the lubricant is magnesium stearate. In some embodiments, the pharmaceutical formulation further comprises about 0.3 mg to about 1.5 mg of the lubricant, wherein the lubricant is magnesium stearate. In some embodiments, the pharmaceutical formulation further comprises about 0.3 mg to about 1 mg of the lubricant, wherein the lubricant is magnesium stearate.

In some embodiments, the 1,1,1,3,3,3-hexafluoropropan-2-yl 4-(2-(pyrrolidin-1-yl)-4-(trifluoromethyl)benzyl)piperazine-1-carboxylate is in free base form. In some embodiments, the pharmaceutical formulation comprises about 1 mg to about 60 mg of 1,1,1,3,3,3-hexafluoropropan-2-yl 4-(2-(pyrrolidin-1-yl)-4-(trifluoromethyl)benzyl)piperazine-1-carboxylate free base. In some embodiments, the pharmaceutical formulation comprises about 1 mg to about 55 mg of 1,1,1,3,3,3-hexafluoropropan-2-yl 4-(2-(pyrrolidin-1-yl)-4-(trifluoromethyl)benzyl)piperazine-1-carboxylate free base. In some embodiments, the pharmaceutical formulation comprises about 1 mg to about 50 mg of 1,1,1,3,3,3-hexafluoropropan-2-yl 4-(2-(pyrrolidin-1-yl)-4-(trifluoromethyl)benzyl)piperazine-1-carboxylate free base. In some embodiments, the pharmaceutical formulation comprises about 1 mg to about 45 mg of 1,1,1,3,3,3-hexafluoropropan-2-yl 4-(2-(pyrrolidin-1-yl)-4-(trifluoromethyl)benzyl)piperazine-1-carboxylate free base. In some embodiments, the pharmaceutical formulation comprises about 1 mg to about 40 mg of 1,1,1,3,3,3-hexafluoropropan-2-yl 4-(2-(pyrrolidin-1-yl)-4-(trifluoromethyl)benzyl)piperazine-1-carboxylate free base. In some embodiments, the pharmaceutical formulation comprises about 1 mg to about 35 mg of 1,1,1,3,3,3-hexafluoropropan-2-yl 4-(2-(pyrrolidin-1-yl)-4-(trifluoromethyl)benzyl)piperazine-1-carboxylate free base. In some embodiments, the pharmaceutical formulation comprises about 1 mg to about 30 mg of 1,1,1,3,3,3-hexafluoropropan-2-yl 4-(2-(pyrrolidin-1-yl)-4-(trifluoromethyl)benzyl)piperazine-1-carboxylate free base. In some embodiments, the pharmaceutical formulation comprises about 1 mg to about 25 mg of 1,1,1,3,3,3-hexafluoropropan-2-yl 4-(2-(pyrrolidin-1-yl)-4-(trifluoromethyl)benzyl)piperazine-1-carboxylate free base. In some embodiments, the pharmaceutical formulation comprises about 1 mg to about 20 mg of 1,1,1,3,3,3-hexafluoropropan-2-yl 4-(2-(pyrrolidin-1-yl)-4-(trifluoromethyl)benzyl)piperazine-1-carboxylate free base. In some embodiments, the pharmaceutical formulation comprises about 1 mg to about 15 mg of 1,1,1,3,3,3-hexafluoropropan-2-yl 4-(2-(pyrrolidin-1-yl)-4-(trifluoromethyl)benzyl)piperazine-1-carboxylate free base. In some embodiments, the pharmaceutical formulation comprises about 1 mg to about 10 mg of 1,1,1,3,3,3-hexafluoropropan-2-yl 4-(2-(pyrrolidin-1-yl)-4-(trifluoromethyl)benzyl)piperazine-1-carboxylate free base. In some embodiments, the pharmaceutical formulation comprises about 2 mg to about 30 mg of 1,1,1,3,3,3-hexafluoropropan-2-yl 4-(2-(pyrrolidin-1-yl)-4-(trifluoromethyl)benzyl)piperazine-1-carboxylate free base. In some embodiments, the pharmaceutical formulation comprises about 2 mg to about 25 mg of 1,1,1,3,3,3-hexafluoropropan-2-yl 4-(2-(pyrrolidin-1-yl)-4-(trifluoromethyl)benzyl)piperazine-1-carboxylate free base. In some embodiments, the pharmaceutical formulation comprises about 2 mg to about 20 mg of 1,1,1,3,3,3-hexafluoropropan-2-yl 4-(2-(pyrrolidin-1-yl)-4-(trifluoromethyl)benzyl)piperazine-1-carboxylate free base. In some embodiments, the pharmaceutical formulation comprises about 2 mg to about 15 mg of 1,1,1,3,3,3-hexafluoropropan-2-yl 4-(2-(pyrrolidin-1-yl)-4-(trifluoromethyl)benzyl)piperazine-1-carboxylate free base. In some embodiments, the pharmaceutical formulation comprises about 2 mg to about 10 mg of 1,1,1,3,3,3-hexafluoropropan-2-yl 4-(2-(pyrrolidin-1-yl)-4-(trifluoromethyl)benzyl)piperazine-1-carboxylate free base. In some embodiments, the pharmaceutical formulation comprises about 1 mg of 1,1,1,3,3,3-hexafluoropropan-2-yl 4-(2-(pyrrolidin-1-yl)-4-(trifluoromethyl)benzyl)piperazine-1-carboxylate free base. In some embodiments, the pharmaceutical formulation comprises about 1.5 mg of 1,1,1,3,3,3-hexafluoropropan-2-yl 4-(2-(pyrrolidin-1-yl)-4-(trifluoromethyl)benzyl)piperazine-1-carboxylate free base. In some embodiments, the pharmaceutical formulation comprises about 2 mg of 1,1,1,3,3,3-hexafluoropropan-2-yl 4-(2-(pyrrolidin-1-yl)-4-(trifluoromethyl)benzyl)piperazine-1-carboxylate free base. In some embodiments, the pharmaceutical formulation comprises about 2.5 mg of 1,1,1,3,3,3-hexafluoropropan-2-yl 4-(2-(pyrrolidin-1-yl)-4-(trifluoromethyl)benzyl)piperazine-1-carboxylate free base. In some embodiments, the pharmaceutical formulation comprises about 3 mg of 1,1,1,3,3,3-hexafluoropropan-2-yl 4-(2-(pyrrolidin-1-yl)-4-(trifluoromethyl)benzyl)piperazine-1-carboxylate free base. In some embodiments, the pharmaceutical formulation comprises about 3.5 mg of 1,1,1,3,3,3-hexafluoropropan-2-yl 4-(2-(pyrrolidin-1-yl)-4-(trifluoromethyl)benzyl)piperazine-1-carboxylate free base. In some embodiments, the pharmaceutical formulation comprises about 4 mg of 1,1,1,3,3,3-hexafluoropropan-2-yl 4-(2-(pyrrolidin-1-yl)-4-(trifluoromethyl)benzyl)piperazine-1-carboxylate free base. In some embodiments, the pharmaceutical formulation comprises about 4.5 mg of 1,1,1,3,3,3-hexafluoropropan-2-yl 4-(2-(pyrrolidin-1-yl)-4-(trifluoromethyl)benzyl)piperazine-1-carboxylate free base. In some embodiments, the pharmaceutical formulation comprises about 5 mg of 1,1,1,3,3,3-hexafluoropropan-2-yl 4-(2-(pyrrolidin-1-yl)-4-(trifluoromethyl)benzyl)piperazine-1-carboxylate free base. In some embodiments, the pharmaceutical formulation comprises about 6 mg of 1,1,1,3,3,3-hexafluoropropan-2-yl 4-(2-(pyrrolidin-1-yl)-4-(trifluoromethyl)benzyl)piperazine-1-carboxylate free base. In some embodiments, the pharmaceutical formulation comprises about 7 mg of 1,1,1,3,3,3-hexafluoropropan-2-yl 4-(2-(pyrrolidin-1-yl)-4-(trifluoromethyl)benzyl)piperazine-1-carboxylate free base. In some embodiments, the pharmaceutical formulation comprises about 8 mg of 1,1,1,3,3,3-hexafluoropropan-2-yl 4-(2-(pyrrolidin-1-yl)-4-(trifluoromethyl)benzyl)piperazine-1-carboxylate free base. In some embodiments, the pharmaceutical formulation comprises about 9 mg of 1,1,1,3,3,3-hexafluoropropan-2-yl 4-(2-(pyrrolidin-1-yl)-4-(trifluoromethyl)benzyl)piperazine-1-carboxylate free base. In some embodiments, the pharmaceutical formulation comprises about 10 mg of 1,1,1,3,3,3-hexafluoropropan-2-yl 4-(2-(pyrrolidin-1-yl)-4-(trifluoromethyl)benzyl)piperazine-1-carboxylate free base. In some embodiments, the pharmaceutical formulation comprises about 11 mg of 1,1,1,3,3,3-hexafluoropropan-2-yl 4-(2-(pyrrolidin-1-yl)-4-(trifluoromethyl)benzyl)piperazine-1-carboxylate free base. In some embodiments, the pharmaceutical formulation comprises about 12 mg of 1,1,1,3,3,3-hexafluoropropan-2-yl 4-(2-(pyrrolidin-1-yl)-4-(trifluoromethyl)benzyl)piperazine-1-carboxylate free base. In some embodiments, the pharmaceutical formulation comprises about 13 mg of 1,1,1,3,3,3-hexafluoropropan-2-yl 4-(2-(pyrrolidin-1-yl)-4-(trifluoromethyl)benzyl)piperazine-1-carboxylate free base. In some embodiments, the pharmaceutical formulation comprises about 14 mg of 1,1,1,3,3,3-hexafluoropropan-2-yl 4-(2-(pyrrolidin-1-yl)-4-(trifluoromethyl)benzyl)piperazine-1-carboxylate free base. In some embodiments, the pharmaceutical formulation comprises about 15 mg of 1,1,1,3,3,3-hexafluoropropan-2-yl 4-(2-(pyrrolidin-1-yl)-4-(trifluoromethyl)benzyl)piperazine-1-carboxylate free base. In some embodiments, the pharmaceutical formulation comprises about 16 mg of 1,1,1,3,3,3-hexafluoropropan-2-yl 4-(2-(pyrrolidin-1-yl)-4-(trifluoromethyl)benzyl)piperazine-1-carboxylate free base. In some embodiments, the pharmaceutical formulation comprises about 17 mg of 1,1,1,3,3,3-hexafluoropropan-2-yl 4-(2-(pyrrolidin-1-yl)-4-(trifluoromethyl)benzyl)piperazine-1-carboxylate free base. In some embodiments, the pharmaceutical formulation comprises about 18 mg of 1,1,1,3,3,3-hexafluoropropan-2-yl 4-(2-(pyrrolidin-1-yl)-4-(trifluoromethyl)benzyl)piperazine-1-carboxylate free base. In some embodiments, the pharmaceutical formulation comprises about 19 mg of 1,1,1,3,3,3-hexafluoropropan-2-yl 4-(2-(pyrrolidin-1-yl)-4-(trifluoromethyl)benzyl)piperazine-1-carboxylate free base. In some embodiments, the pharmaceutical formulation comprises about 20 mg of 1,1,1,3,3,3-hexafluoropropan-2-yl 4-(2-(pyrrolidin-1-yl)-4-(trifluoromethyl)benzyl)piperazine-1-carboxylate free base. In some embodiments, the pharmaceutical formulation comprises about 25 mg of 1,1,1,3,3,3-hexafluoropropan-2-yl 4-(2-(pyrrolidin-1-yl)-4-(trifluoromethyl)benzyl)piperazine-1-carboxylate free base. In some embodiments, the pharmaceutical formulation comprises about 30 mg of 1,1,1,3,3,3-hexafluoropropan-2-yl 4-(2-(pyrrolidin-1-yl)-4-(trifluoromethyl)benzyl)piperazine-1-carboxylate free base. In some embodiments, the pharmaceutical formulation comprises about 35 mg of 1,1,1,3,3,3-hexafluoropropan-2-yl 4-(2-(pyrrolidin-1-yl)-4-(trifluoromethyl)benzyl)piperazine-1-carboxylate free base. In some embodiments, the pharmaceutical formulation comprises about 40 mg of 1,1,1,3,3,3-hexafluoropropan-2-yl 4-(2-(pyrrolidin-1-yl)-4-(trifluoromethyl)benzyl)piperazine-1-carboxylate free base. In some embodiments, the pharmaceutical formulation comprises about 45 mg of 1,1,1,3,3,3-hexafluoropropan-2-yl 4-(2-(pyrrolidin-1-yl)-4-(trifluoromethyl)benzyl)piperazine-1-carboxylate free base. In some embodiments, the pharmaceutical formulation comprises about 50 mg of 1,1,1,3,3,3-hexafluoropropan-2-yl 4-(2-(pyrrolidin-1-yl)-4-(trifluoromethyl)benzyl)piperazine-1-carboxylate free base. In some embodiments, the pharmaceutical formulation comprises about 55 mg of 1,1,1,3,3,3-hexafluoropropan-2-yl 4-(2-(pyrrolidin-1-yl)-4-(trifluoromethyl)benzyl)piperazine-1-carboxylate free base. In some embodiments, the pharmaceutical formulation comprises about 60 mg of 1,1,1,3,3,3-hexafluoropropan-2-yl 4-(2-(pyrrolidin-1-yl)-4-(trifluoromethyl)benzyl)piperazine-1-carboxylate free base.

In some embodiments, the 1,1,1,3,3,3-hexafluoropropan-2-yl 4-(2-(pyrrolidin-1-yl)-4-(trifluoromethyl)benzyl)piperazine-1-carboxylate is in a pharmaceutically acceptable salt form. In some embodiments, the 1,1,1,3,3,3-hexafluoropropan-2-yl 4-(2-(pyrrolidin-1-yl)-4-(trifluoromethyl)benzyl)piperazine-1-carboxylate is the 1,1,1,3,3,3-hexafluoropropan-2-yl 4-(2-(pyrrolidin-1-yl)-4-(trifluoromethyl)

benzyl)piperazine-1-carboxylate hydrochloride salt. In some embodiments, the pharmaceutical formulation comprises about 1 mg to about 60 mg of 1,1,1,3,3,3-hexafluoropropan-2-yl 4-(2-(pyrrolidin-1-yl)-4-(trifluoromethyl)benzyl)piperazine-1-carboxylate hydrochloride salt. In some embodiments, the pharmaceutical formulation comprises about 1 mg to about 55 mg of 1,1,1,3,3,3-hexafluoropropan-2-yl 4-(2-(pyrrolidin-1-yl)-4-(trifluoromethyl)benzyl)piperazine-1-carboxylate hydrochloride salt. In some embodiments, the pharmaceutical formulation comprises about 1 mg to about 50 mg of 1,1,1,3,3,3-hexafluoropropan-2-yl 4-(2-(pyrrolidin-1-yl)-4-(trifluoromethyl)benzyl)piperazine-1-carboxylate hydrochloride salt. In some embodiments, the pharmaceutical formulation comprises about 1 mg to about 45 mg of 1,1,1,3,3,3-hexafluoropropan-2-yl 4-(2-(pyrrolidin-1-yl)-4-(trifluoromethyl)benzyl)piperazine-1-carboxylate hydrochloride salt. In some embodiments, the pharmaceutical formulation comprises about 1 mg to about 40 mg of 1,1,1,3,3,3-hexafluoropropan-2-yl 4-(2-(pyrrolidin-1-yl)-4-(trifluoromethyl)benzyl)piperazine-1-carboxylate hydrochloride salt. In some embodiments, the pharmaceutical formulation comprises about 1 mg to about 35 mg of 1,1,1,3,3,3-hexafluoropropan-2-yl 4-(2-(pyrrolidin-1-yl)-4-(trifluoromethyl)benzyl)piperazine-1-carboxylate hydrochloride salt. In some embodiments, the pharmaceutical formulation comprises about 1 mg to about 30 mg of 1,1,1,3,3,3-hexafluoropropan-2-yl 4-(2-(pyrrolidin-1-yl)-4-(trifluoromethyl)benzyl)piperazine-1-carboxylate hydrochloride salt. In some embodiments, the pharmaceutical formulation comprises about 1 mg to about 25 mg of 1,1,1,3,3,3-hexafluoropropan-2-yl 4-(2-(pyrrolidin-1-yl)-4-(trifluoromethyl)benzyl)piperazine-1-carboxylate hydrochloride salt. In some embodiments, the pharmaceutical formulation comprises about 1 mg to about 20 mg of 1,1,1,3,3,3-hexafluoropropan-2-yl 4-(2-(pyrrolidin-1-yl)-4-(trifluoromethyl)benzyl)piperazine-1-carboxylate hydrochloride salt. In some embodiments, the pharmaceutical formulation comprises about 1 mg to about 15 mg of 1,1,1,3,3,3-hexafluoropropan-2-yl 4-(2-(pyrrolidin-1-yl)-4-(trifluoromethyl)benzyl)piperazine-1-carboxylate hydrochloride salt. In some embodiments, the pharmaceutical formulation comprises about 1 mg to about 10 mg of 1,1,1,3,3,3-hexafluoropropan-2-yl 4-(2-(pyrrolidin-1-yl)-4-(trifluoromethyl)benzyl)piperazine-1-carboxylate hydrochloride salt. In some embodiments, the pharmaceutical formulation comprises about 2 mg to about 30 mg of 1,1,1,3,3,3-hexafluoropropan-2-yl 4-(2-(pyrrolidin-1-yl)-4-(trifluoromethyl)benzyl)piperazine-1-carboxylate hydrochloride salt. In some embodiments, the pharmaceutical formulation comprises about 2 mg to about 25 mg of 1,1,1,3,3,3-hexafluoropropan-2-yl 4-(2-(pyrrolidin-1-yl)-4-(trifluoromethyl)benzyl)piperazine-1-carboxylate hydrochloride salt. In some embodiments, the pharmaceutical formulation comprises about 2 mg to about 20 mg of 1,1,1,3,3,3-hexafluoropropan-2-yl 4-(2-(pyrrolidin-1-yl)-4-(trifluoromethyl)benzyl)piperazine-1-carboxylate hydrochloride salt. In some embodiments, the pharmaceutical formulation comprises about 2 mg to about 15 mg of 1,1,1,3,3,3-hexafluoropropan-2-yl 4-(2-(pyrrolidin-1-yl)-4-(trifluoromethyl)benzyl)piperazine-1-carboxylate hydrochloride salt. In some embodiments, the pharmaceutical formulation comprises about 2 mg to about 10 mg of 1,1,1,3,3,3-hexafluoropropan-2-yl 4-(2-(pyrrolidin-1-yl)-4-(trifluoromethyl)benzyl)piperazine-1-carboxylate hydrochloride salt. In some embodiments, the pharmaceutical formulation comprises about 1 mg of 1,1,1,3,3,3-hexafluoropropan-2-yl 4-(2-(pyrrolidin-1-yl)-4-(trifluoromethyl)benzyl)piperazine-1-carboxylate hydrochloride salt. In some embodiments, the pharmaceutical formulation comprises about 1.5 mg of 1,1,1,3,3,3-hexafluoropropan-2-yl 4-(2-(pyrrolidin-1-yl)-4-(trifluoromethyl)benzyl)piperazine-1-carboxylate hydrochloride salt. In some embodiments, the pharmaceutical formulation comprises about 2 mg of 1,1,1,3,3,3-hexafluoropropan-2-yl 4-(2-(pyrrolidin-1-yl)-4-(trifluoromethyl)benzyl)piperazine-1-carboxylate hydrochloride salt. In some embodiments, the pharmaceutical formulation comprises about 2.5 mg of 1,1,1,3,3,3-hexafluoropropan-2-yl 4-(2-(pyrrolidin-1-yl)-4-(trifluoromethyl)benzyl)piperazine-1-carboxylate hydrochloride salt. In some embodiments, the pharmaceutical formulation comprises about 3 mg of 1,1,1,3,3,3-hexafluoropropan-2-yl 4-(2-(pyrrolidin-1-yl)-4-(trifluoromethyl)benzyl)piperazine-1-carboxylate hydrochloride salt. In some embodiments, the pharmaceutical formulation comprises about 3.5 mg of 1,1,1,3,3,3-hexafluoropropan-2-yl 4-(2-(pyrrolidin-1-yl)-4-(trifluoromethyl)benzyl)piperazine-1-carboxylate hydrochloride salt. In some embodiments, the pharmaceutical formulation comprises about 4 mg of 1,1,1,3,3,3-hexafluoropropan-2-yl 4-(2-(pyrrolidin-1-yl)-4-(trifluoromethyl)benzyl)piperazine-1-carboxylate hydrochloride salt. In some embodiments, the pharmaceutical formulation comprises about 4.5 mg of 1,1,1,3,3,3-hexafluoropropan-2-yl 4-(2-(pyrrolidin-1-yl)-4-(trifluoromethyl)benzyl)piperazine-1-carboxylate hydrochloride salt. In some embodiments, the pharmaceutical formulation comprises about 5 mg of 1,1,1,3,3,3-hexafluoropropan-2-yl 4-(2-(pyrrolidin-1-yl)-4-(trifluoromethyl)benzyl)piperazine-1-carboxylate hydrochloride salt. In some embodiments, the pharmaceutical formulation comprises about 6 mg of 1,1,1,3,3,3-hexafluoropropan-2-yl 4-(2-(pyrrolidin-1-yl)-4-(trifluoromethyl)benzyl)piperazine-1-carboxylate hydrochloride salt. In some embodiments, the pharmaceutical formulation comprises about 7 mg of 1,1,1,3,3,3-hexafluoropropan-2-yl 4-(2-(pyrrolidin-1-yl)-4-(trifluoromethyl)benzyl)piperazine-1-carboxylate hydrochloride salt. In some embodiments, the pharmaceutical formulation comprises about 8 mg of 1,1,1,3,3,3-hexafluoropropan-2-yl 4-(2-(pyrrolidin-1-yl)-4-(trifluoromethyl)benzyl)piperazine-1-carboxylate hydrochloride salt. In some embodiments, the pharmaceutical formulation comprises about 9 mg of 1,1,1,3,3,3-hexafluoropropan-2-yl 4-(2-(pyrrolidin-1-yl)-4-(trifluoromethyl)benzyl)piperazine-1-carboxylate hydrochloride salt. In some embodiments, the pharmaceutical formulation comprises about 10 mg of 1,1,1,3,3,3-hexafluoropropan-2-yl 4-(2-(pyrrolidin-1-yl)-4-(trifluoromethyl)benzyl)piperazine-1-carboxylate hydrochloride salt. In some embodiments, the pharmaceutical formulation comprises about 11 mg of 1,1,1,3,3,3-hexafluoropropan-2-yl 4-(2-(pyrrolidin-1-yl)-4-(trifluoromethyl)benzyl)piperazine-1-carboxylate hydrochloride salt. In some embodiments, the pharmaceutical formulation comprises about 12 mg of 1,1,1,3,3,3-hexafluoropropan-2-yl 4-(2-(pyrrolidin-1-yl)-4-(trifluoromethyl)benzyl)piperazine-1-carboxylate hydrochloride salt. In some embodiments, the pharmaceutical formulation comprises about 13 mg of 1,1,1,3,3,3-hexafluoropropan-2-yl 4-(2-(pyrrolidin-1-yl)-4-(trifluoromethyl)benzyl)piperazine-1-carboxylate hydrochloride salt. In some embodiments, the pharmaceutical formulation comprises about 14 mg of 1,1,1,3,3,3-hexafluoropropan-2-yl 4-(2-(pyrrolidin-1-yl)-4-(trifluoromethyl)benzyl)piperazine-1-carboxylate hydrochloride salt. In some embodiments, the pharmaceutical formulation comprises about 15 mg of 1,1,1,3,3,3-hexafluoropropan-2-yl 4-(2-(pyrrolidin-1-yl)-4-(trifluoromethyl)benzyl)piperazine-1-carboxylate hydrochloride salt. In some embodiments, the pharmaceutical formulation comprises about 16 mg of 1,1,1,3,3,3-hexafluoropropan-2-yl 4-(2-(pyrrolidin-1-yl)-4-(trifluoromethyl)benzyl)piperazine-1-carboxylate hydrochloride salt. In some embodiments, the pharmaceutical formulation comprises about 17 mg of 1,1,1,3,3,3-hexafluoropropan-2-yl 4-(2-(pyrrolidin-1-yl)-4-(trifluoromethyl)benzyl)piperazine-1-carboxylate hydrochloride salt. In some embodiments, the pharmaceutical formulation comprises about 18 mg of 1,1,1,3,3,3-hexafluoropropan-2-yl 4-(2-(pyrrolidin-1-yl)-4-(trifluoromethyl)benzyl)piperazine-1-carboxylate hydrochloride salt. In some embodiments, the pharmaceutical formulation comprises about 19 mg of 1,1,1,3,3,3-hexafluoropropan-2-yl 4-(2-(pyrrolidin-1-yl)-4-(trifluoromethyl)benzyl)piperazine-1-carboxylate hydrochloride salt. In some embodiments, the pharmaceutical formulation comprises about 20 mg of 1,1,1,3,3,3-hexafluoropropan-2-yl 4-(2-(pyrrolidin-1-yl)-4-(trifluoromethyl)benzyl)piperazine-1-carboxylate hydrochloride salt. In some embodiments, the pharmaceutical formulation comprises about 25 mg of 1,1,1,3,3,3-hexafluoropropan-2-yl 4-(2-(pyrrolidin-1-yl)-4-(trifluoromethyl)benzyl)piperazine-1-carboxylate hydrochloride salt. In some embodiments, the pharmaceutical formulation comprises about 30 mg of 1,1,1,3,3,3-hexafluoropropan-2-yl 4-(2-(pyrrolidin-1-yl)-4-(trifluoromethyl)benzyl)piperazine-1-carboxylate hydrochloride salt. In some embodiments, the pharmaceutical formulation comprises about 35 mg of 1,1,1,3,3,3-hexafluoropropan-2-yl 4-(2-(pyrrolidin-1-yl)-4-(trifluoromethyl)benzyl)piperazine-1-carboxylate hydrochloride salt. In some embodiments, the pharmaceutical formulation comprises about 40 mg of 1,1,1,3,3,3-hexafluoropropan-2-yl 4-(2-(pyrrolidin-1-yl)-4-(trifluoromethyl)benzyl)piperazine-1-carboxylate hydrochloride salt. In some embodiments, the pharmaceutical formulation comprises about 45 mg of 1,1,1,3,3,3-hexafluoropropan-2-yl 4-(2-(pyrrolidin-1-yl)-4-(trifluoromethyl)benzyl)piperazine-1-carboxylate hydrochloride salt. In some embodiments, the pharmaceutical formulation comprises about 50 mg of 1,1,1,3,3,3-hexafluoropropan-2-yl 4-(2-(pyrrolidin-1-yl)-4-(trifluoromethyl)benzyl)piperazine-1-carboxylate hydrochloride salt. In some embodiments, the pharmaceutical formulation comprises about 55 mg of 1,1,1,3,3,3-hexafluoropropan-2-yl 4-(2-(pyrrolidin-1-yl)-4-(trifluoromethyl)benzyl)piperazine-1-carboxylate hydrochloride salt. In some embodiments, the pharmaceutical formulation comprises about 60 mg of 1,1,1,3,3,3-hexafluoropropan-2-yl 4-(2-(pyrrolidin-1-yl)-4-(trifluoromethyl)benzyl)piperazine-1-carboxylate hydrochloride salt.

In some embodiments, the 1,1,1,3,3,3-hexafluoropropan-2-yl 4-(2-(pyrrolidin-1-yl)-4-(trifluoromethyl)benzyl)piperazine-1-carboxylate is the 1,1,1,3,3,3-hexafluoropropan-2-yl 4-(2-(pyrrolidin-1-yl)-4-(trifluoromethyl)benzyl)piperazine-1-carboxylate fumarate salt. In some embodiments, the pharmaceutical formulation comprises about 1 mg to about 60 mg of 1,1,1,3,3,3-hexafluoropropan-2-yl 4-(2-(pyrrolidin-1-yl)-4-(trifluoromethyl)benzyl)piperazine-1-carboxylate fumarate salt. In some embodiments, the pharmaceutical formulation comprises about 1 mg to about 55 mg of 1,1,1,3,3,3-hexafluoropropan-2-yl 4-(2-(pyrrolidin-1-yl)-4-(trifluoromethyl)benzyl)piperazine-1-carboxylate fumarate salt. In some embodiments, the pharmaceutical formulation comprises about 1 mg to about 50 mg of 1,1,1,3,3,3-hexafluoropropan-2-yl 4-(2-(pyrrolidin-1-yl)-4-(trifluoromethyl)benzyl)piperazine-1-carboxylate fumarate salt. In some embodiments, the pharmaceutical formulation comprises about 1 mg to about 45 mg of 1,1,1,3,3,3-hexafluoropropan-2-yl 4-(2-(pyrrolidin-1-yl)-4-(trifluoromethyl)benzyl)piperazine-1-carboxylate fumarate salt. In some embodiments, the pharmaceutical formulation comprises about 1 mg to about 40 mg of 1,1,1,3,3,3-hexafluoropropan-2-yl 4-(2-(pyrrolidin-1-yl)-4-(trifluoromethyl)benzyl)piperazine-1-carboxylate fumarate salt. In some embodiments, the pharmaceutical formulation comprises about 1 mg to about 35 mg of 1,1,1,3,3,3-hexafluoropropan-2-yl 4-(2-(pyrrolidin-1-yl)-4-(trifluoromethyl)benzyl)piperazine-1-carboxylate fumarate salt. In some embodiments, the pharmaceutical formulation comprises about 1 mg to about 30 mg of 1,1,1,3,3,3-hexafluoropropan-2-yl 4-(2-(pyrrolidin-1-yl)-4-(trifluoromethyl)benzyl)piperazine-1-carboxylate fumarate salt. In some embodiments, the pharmaceutical formulation comprises about 1 mg to about 25 mg of 1,1,1,3,3,3-hexafluoropropan-2-yl 4-(2-(pyrrolidin-1-yl)-4-(trifluoromethyl)benzyl)piperazine-1-carboxylate fumarate salt. In some embodiments, the pharmaceutical formulation comprises about 1 mg to about 20 mg of 1,1,1,3,3,3-hexafluoropropan-2-yl 4-(2-(pyrrolidin-1-yl)-4-(trifluoromethyl)benzyl)piperazine-1-carboxylate fumarate salt. In some embodiments, the pharmaceutical formulation comprises about 1 mg to about 15 mg of 1,1,1,3,3,3-hexafluoropropan-2-yl 4-(2-(pyrrolidin-1-yl)-4-(trifluoromethyl)benzyl)piperazine-1-carboxylate fumarate salt. In some embodiments, the pharmaceutical formulation comprises about 1 mg to about 10 mg of 1,1,1,3,3,3-hexafluoropropan-2-yl 4-(2-(pyrrolidin-1-yl)-4-(trifluoromethyl)benzyl)piperazine-1-carboxylate fumarate salt. In some embodiments, the pharmaceutical formulation comprises about 2 mg to about 30 mg of 1,1,1,3,3,3-hexafluoropropan-2-yl 4-(2-(pyrrolidin-1-yl)-4-(trifluoromethyl)benzyl)piperazine-1-carboxylate fumarate salt. In some embodiments, the pharmaceutical formulation comprises about 2 mg to about 25 mg of 1,1,1,3,3,3-hexafluoropropan-2-yl 4-(2-(pyrrolidin-1-yl)-4-(trifluoromethyl)benzyl)piperazine-1-carboxylate fumarate salt. In some embodiments, the pharmaceutical formulation comprises about 2 mg to about 20 mg of 1,1,1,3,3,3-hexafluoropropan-2-yl 4-(2-(pyrrolidin-1-yl)-4-(trifluoromethyl)benzyl)piperazine-1-carboxylate fumarate salt. In some embodiments, the pharmaceutical formulation comprises about 2 mg to about 15 mg of 1,1,1,3,3,3-hexafluoropropan-2-yl 4-(2-(pyrrolidin-1-yl)-4-(trifluoromethyl)benzyl)piperazine-1-carboxylate fumarate salt. In some embodiments, the pharmaceutical formulation comprises about 2 mg to about 10 mg of 1,1,1,3,3,3-hexafluoropropan-2-yl 4-(2-(pyrrolidin-1-yl)-4-(trifluoromethyl)benzyl)piperazine-1-carboxylate fumarate salt. In some embodiments, the pharmaceutical formulation comprises about 1 mg of 1,1,1,3,3,3-hexafluoropropan-2-yl 4-(2-(pyrrolidin-1-yl)-4-(trifluoromethyl)benzyl)piperazine-1-carboxylate fumarate salt. In some embodiments, the pharmaceutical formulation comprises about 1.5 mg of 1,1,1,3,3,3-hexafluoropropan-2-yl 4-(2-(pyrrolidin-1-yl)-4-(trifluoromethyl)benzyl)piperazine-1-carboxylate fumarate salt. In some embodiments, the pharmaceutical formulation comprises about 2 mg of 1,1,1,3,3,3-hexafluoropropan-2-yl 4-(2-(pyrrolidin-1-yl)-4-(trifluoromethyl)benzyl)piperazine-1-carboxylate fumarate salt. In some embodiments, the pharmaceutical formulation comprises about 2.5 mg of 1,1,1,3,3,3-hexafluoropropan-2-yl 4-(2-(pyrrolidin-1-yl)-4-(trifluoromethyl)benzyl)piperazine-1-carboxylate fumarate salt. In some embodiments, the pharmaceutical formulation comprises about 3 mg of 1,1,1,3,3,3-hexafluoropropan-2-yl 4-(2-(pyrrolidin-1-yl)-4-(trifluoromethyl)benzyl)piperazine-1-carboxylate fumarate salt. In some embodiments, the pharmaceutical formulation comprises about 3.5 mg of 1,1,1,3,3,3-hexafluoropropan-2-yl 4-(2-(pyrrolidin-1-yl)-4-

(trifluoromethyl)benzyl)piperazine-1-carboxylate fumarate salt. In some embodiments, the pharmaceutical formulation comprises about 4 mg of 1,1,1,3,3,3-hexafluoropropan-2-yl 4-(2-(pyrrolidin-1-yl)-4-(trifluoromethyl)benzyl)piperazine-1-carboxylate fumarate salt. In some embodiments, the pharmaceutical formulation comprises about 4.5 mg of 1,1,1,3,3,3-hexafluoropropan-2-yl 4-(2-(pyrrolidin-1-yl)-4-(trifluoromethyl)benzyl)piperazine-1-carboxylate fumarate salt. In some embodiments, the pharmaceutical formulation comprises about 5 mg of 1,1,1,3,3,3-hexafluoropropan-2-yl 4-(2-(pyrrolidin-1-yl)-4-(trifluoromethyl)benzyl)piperazine-1-carboxylate fumarate salt. In some embodiments, the pharmaceutical formulation comprises about 6 mg of 1,1,1,3,3,3-hexafluoropropan-2-yl 4-(2-(pyrrolidin-1-yl)-4-(trifluoromethyl)benzyl)piperazine-1-carboxylate fumarate salt. In some embodiments, the pharmaceutical formulation comprises about 7 mg of 1,1,1,3,3,3-hexafluoropropan-2-yl 4-(2-(pyrrolidin-1-yl)-4-(trifluoromethyl)benzyl)piperazine-1-carboxylate fumarate salt. In some embodiments, the pharmaceutical formulation comprises about 8 mg of 1,1,1,3,3,3-hexafluoropropan-2-yl 4-(2-(pyrrolidin-1-yl)-4-(trifluoromethyl)benzyl)piperazine-1-carboxylate fumarate salt. In some embodiments, the pharmaceutical formulation comprises about 9 mg of 1,1,1,3,3,3-hexafluoropropan-2-yl 4-(2-(pyrrolidin-1-yl)-4-(trifluoromethyl)benzyl)piperazine-1-carboxylate fumarate salt. In some embodiments, the pharmaceutical formulation comprises about 10 mg of 1,1,1,3,3,3-hexafluoropropan-2-yl 4-(2-(pyrrolidin-1-yl)-4-(trifluoromethyl)benzyl)piperazine-1-carboxylate fumarate salt. In some embodiments, the pharmaceutical formulation comprises about 11 mg of 1,1,1,3,3,3-hexafluoropropan-2-yl 4-(2-(pyrrolidin-1-yl)-4-(trifluoromethyl)benzyl)piperazine-1-carboxylate fumarate salt. In some embodiments, the pharmaceutical formulation comprises about 12 mg of 1,1,1,3,3,3-hexafluoropropan-2-yl 4-(2-(pyrrolidin-1-yl)-4-(trifluoromethyl)benzyl)piperazine-1-carboxylate fumarate salt. In some embodiments, the pharmaceutical formulation comprises about 13 mg of 1,1,1,3,3,3-hexafluoropropan-2-yl 4-(2-(pyrrolidin-1-yl)-4-(trifluoromethyl)benzyl)piperazine-1-carboxylate fumarate salt. In some embodiments, the pharmaceutical formulation comprises about 14 mg of 1,1,1,3,3,3-hexafluoropropan-2-yl 4-(2-(pyrrolidin-1-yl)-4-(trifluoromethyl)benzyl)piperazine-1-carboxylate fumarate salt. In some embodiments, the pharmaceutical formulation comprises about 15 mg of 1,1,1,3,3,3-hexafluoropropan-2-yl 4-(2-(pyrrolidin-1-yl)-4-(trifluoromethyl)benzyl)piperazine-1-carboxylate fumarate salt. In some embodiments, the pharmaceutical formulation comprises about 16 mg of 1,1,1,3,3,3-hexafluoropropan-2-yl 4-(2-(pyrrolidin-1-yl)-4-(trifluoromethyl)benzyl)piperazine-1-carboxylate fumarate salt. In some embodiments, the pharmaceutical formulation comprises about 17 mg of 1,1,1,3,3,3-hexafluoropropan-2-yl 4-(2-(pyrrolidin-1-yl)-4-(trifluoromethyl)benzyl)piperazine-1-carboxylate fumarate salt. In some embodiments, the pharmaceutical formulation comprises about 18 mg of 1,1,1,3,3,3-hexafluoropropan-2-yl 4-(2-(pyrrolidin-1-yl)-4-(trifluoromethyl)benzyl)piperazine-1-carboxylate fumarate salt. In some embodiments, the pharmaceutical formulation comprises about 19 mg of 1,1,1,3,3,3-hexafluoropropan-2-yl 4-(2-(pyrrolidin-1-yl)-4-(trifluoromethyl)benzyl)piperazine-1-carboxylate fumarate salt. In some embodiments, the pharmaceutical formulation comprises about 20 mg of 1,1,1,3,3,3-hexafluoropropan-2-yl 4-(2-(pyrrolidin-1-yl)-4-(trifluoromethyl)benzyl)piperazine-1-carboxylate fumarate salt. In some embodiments, the pharmaceutical formulation comprises about 25 mg of 1,1,1,3,3,3-hexafluoropropan-2-yl 4-(2-(pyrrolidin-1-yl)-4-(trifluoromethyl)benzyl)piperazine-1-carboxylate fumarate salt. In some embodiments, the pharmaceutical formulation comprises about 30 mg of 1,1,1,3,3,3-hexafluoropropan-2-yl 4-(2-(pyrrolidin-1-yl)-4-(trifluoromethyl)benzyl)piperazine-1-carboxylate fumarate salt. In some embodiments, the pharmaceutical formulation comprises about 35 mg of 1,1,1,3,3,3-hexafluoropropan-2-yl 4-(2-(pyrrolidin-1-yl)-4-(trifluoromethyl)benzyl)piperazine-1-carboxylate fumarate salt. In some embodiments, the pharmaceutical formulation comprises about 40 mg of 1,1,1,3,3,3-hexafluoropropan-2-yl 4-(2-(pyrrolidin-1-yl)-4-(trifluoromethyl)benzyl)piperazine-1-carboxylate fumarate salt. In some embodiments, the pharmaceutical formulation comprises about 45 mg of 1,1,1,3,3,3-hexafluoropropan-2-yl 4-(2-(pyrrolidin-1-yl)-4-(trifluoromethyl)benzyl)piperazine-1-carboxylate fumarate salt. In some embodiments, the pharmaceutical formulation comprises about 50 mg of 1,1,1,3,3,3-hexafluoropropan-2-yl 4-(2-(pyrrolidin-1-yl)-4-(trifluoromethyl)benzyl)piperazine-1-carboxylate fumarate salt. In some embodiments, the pharmaceutical formulation comprises about 55 mg of 1,1,1,3,3,3-hexafluoropropan-2-yl 4-(2-(pyrrolidin-1-yl)-4-(trifluoromethyl)benzyl)piperazine-1-carboxylate fumarate salt. In some embodiments, the pharmaceutical formulation comprises about 60 mg of 1,1,1,3,3,3-hexafluoropropan-2-yl 4-(2-(pyrrolidin-1-yl)-4-(trifluoromethyl)benzyl)piperazine-1-carboxylate fumarate salt.

In some embodiments described herein is a pharmaceutical formulation in a solid dosage form comprising:
(a) about 2 mg to about 12 mg of 1,1,1,3,3,3-hexafluoropropan-2-yl 4-(2-(pyrrolidin-1-yl)-4-(trifluoromethyl)benzyl)piperazine-1-carboxylate hydrochloride salt;
(b) about 14 mg to about 72.5 mg of polyvinyl pyrrolidone K30 (PVP K30);
(c) about 2 mg to about 13 mg of PEG 400;
(d) about 0.4 mg to about 2 mg of Polysorbate 80 (Tween 80);
(e) about 0.4 mg to about 2 mg of silicon dioxide;
(f) about 0.2 mg to about 1 mg of potassium dihydrogen phosphate;
(g) about 33 mg to about 170 mg of microcrystalline cellulose;
(h) about 6 mg to about 30 mg of crospovidone; and
(i) about 0.3 mg to about 1.5 mg of sodium stearyl fumarate.

In some embodiments described herein is a pharmaceutical formulation in a solid dosage form comprising:
(a) about 2 mg to about 12 mg of 1,1,1,3,3,3-hexafluoropropan-2-yl 4-(2-(pyrrolidin-1-yl)-4-(trifluoromethyl)benzyl)piperazine-1-carboxylate hydrochloride salt;
(b) about 17 mg to about 85 mg of polyvinyl pyrrolidone vinyl acetate (PVPVA 64);
(c) about 0.4 mg to about 2 mg of Polysorbate 80 (Tween 80);
(d) about 0.4 mg to about 2 mg of silicon dioxide;
(e) about 0.2 mg to about 1 mg of potassium dihydrogen phosphate;
(f) about 33 mg to about 170 mg of microcrystalline cellulose;
(g) about 6 mg to about 30 mg of crospovidone; and
(h) about 0.3 mg to about 1.5 mg of sodium stearyl fumarate.

In some embodiments, described herein is a pharmaceutical formulation in a solid dosage form comprising:
(a) about 1 mg to about 60 mg of 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt thereof;

(b) about 20 mg to about 400 mg of a filler;

(c) about 3 mg to about 150 mg of a disintegrant; and (d) about 0.1 mg to about 10 mg of a lubricant.

In some embodiments, the pharmaceutical formulation comprises a filler. In some embodiments, the filler is selected from lactose, mannitol, dicalcium phosphate, microcrystalline cellulose, silicified microcrystalline cellulose, starch, and pregelatinized starch (Starch 1500). In some embodiments, the filler is lactose. In some embodiments, the filler is mannitol. In some embodiments, the filler is dicalcium phosphate. In some embodiments, the filler is microcrystalline cellulose. In some embodiments, the filler is silicified microcrystalline cellulose. In some embodiments, the filler is starch. In some embodiments, the filler is pregelatinized starch (Starch 1500). In some embodiments, the pharmaceutical formulation comprises about 20 mg to about 750 mg of a filler. In some embodiments, the pharmaceutical formulation comprises about 20 mg to about 700 mg of a filler. In some embodiments, the pharmaceutical formulation comprises about 20 mg to about 650 mg of a filler. In some embodiments, the pharmaceutical formulation comprises about 20 mg to about 600 mg of a filler. In some embodiments, the pharmaceutical formulation comprises about 20 mg to about 550 mg of a filler. In some embodiments, the pharmaceutical formulation comprises about 20 mg to about 500 mg of a filler. In some embodiments, the pharmaceutical formulation comprises about 20 mg to about 450 mg of a filler. In some embodiments, the pharmaceutical formulation comprises about 20 mg to about 400 mg of a filler. In some embodiments, the pharmaceutical formulation comprises about 20 mg to about 350 mg of a filler. In some embodiments, the pharmaceutical formulation comprises about 20 mg to about 300 mg of a filler. In some embodiments, the pharmaceutical formulation comprises about 20 mg to about 275 mg of a filler. In some embodiments, the pharmaceutical formulation comprises about 20 mg to about 250 mg of a filler. In some embodiments, the pharmaceutical formulation comprises about 20 mg to about 225 mg of a filler. In some embodiments, the pharmaceutical formulation comprises about 20 mg to about 200 mg of a filler. In some embodiments, the pharmaceutical formulation comprises about 25 mg to about 300 mg of a filler. In some embodiments, the pharmaceutical formulation comprises about 25 mg to about 275 mg of a filler. In some embodiments, the pharmaceutical formulation comprises about 25 mg to about 250 mg of a filler. In some embodiments, the pharmaceutical formulation comprises about 25 mg to about 225 mg of a filler. In some embodiments, the pharmaceutical formulation comprises about 25 mg to about 200 mg of a filler. In some embodiments, the filler is selected from lactose, mannitol, dicalcium phosphate, microcrystalline cellulose, silicified microcrystalline cellulose, starch, and pregelatinized starch (Starch 1500). In some embodiments, the pharmaceutical formulation comprises about 30 mg to about 300 mg of a filler. In some embodiments, the pharmaceutical formulation comprises about 30 mg to about 275 mg of a filler. In some embodiments, the pharmaceutical formulation comprises about 30 mg to about 250 mg of a filler. In some embodiments, the pharmaceutical formulation comprises about 30 mg to about 225 mg of a filler. In some embodiments, the pharmaceutical formulation comprises about 30 mg to about 200 mg of a filler. In some embodiments, the pharmaceutical formulation comprises about 30 mg to about 175 mg of a filler. In some embodiments, the pharmaceutical formulation comprises about 30 mg to about 150 mg of a filler. In some embodiments, the pharmaceutical formulation comprises about 30 mg of a filler. In some embodiments, the pharmaceutical formulation comprises about 35 mg of a filler. In some embodiments, the pharmaceutical formulation comprises about 40 mg of a filler. In some embodiments, the pharmaceutical formulation comprises about 45 mg of a filler. In some embodiments, the pharmaceutical formulation comprises about 50 mg of a filler. In some embodiments, the pharmaceutical formulation comprises about 55 mg of a filler. In some embodiments, the pharmaceutical formulation comprises about 60 mg of a filler. In some embodiments, the pharmaceutical formulation comprises about 65 mg of a filler. In some embodiments, the pharmaceutical formulation comprises about 70 mg of a filler. In some embodiments, the pharmaceutical formulation comprises about 75 mg of a filler. In some embodiments, the pharmaceutical formulation comprises about 80 mg of a filler. In some embodiments, the pharmaceutical formulation comprises about 85 mg of a filler. In some embodiments, the pharmaceutical formulation comprises about 90 mg of a filler. In some embodiments, the pharmaceutical formulation comprises about 95 mg of a filler. In some embodiments, the pharmaceutical formulation comprises about 100 mg of a filler. In some embodiments, the pharmaceutical formulation comprises about 105 mg of a filler. In some embodiments, the pharmaceutical formulation comprises about 110 mg of a filler. In some embodiments, the pharmaceutical formulation comprises about 115 mg of a filler. In some embodiments, the pharmaceutical formulation comprises about 120 mg of a filler. In some embodiments, the pharmaceutical formulation comprises about 125 mg of a filler. In some embodiments, the pharmaceutical formulation comprises about 130 mg of a filler. In some embodiments, the pharmaceutical formulation comprises about 135 mg of a filler. In some embodiments, the pharmaceutical formulation comprises about 140 mg of a filler. In some embodiments, the pharmaceutical formulation comprises about 145 mg of a filler. In some embodiments, the pharmaceutical formulation comprises about 150 mg of a filler. In some embodiments, the pharmaceutical formulation comprises about 155 mg of a filler. In some embodiments, the pharmaceutical formulation comprises about 160 mg of a filler. In some embodiments, the pharmaceutical formulation comprises about 165 mg of a filler. In some embodiments, the pharmaceutical formulation comprises about 170 mg of a filler. In some embodiments, the pharmaceutical formulation comprises about 175 mg of a filler. In some embodiments, the pharmaceutical formulation comprises about 180 mg of a filler. In some embodiments, the pharmaceutical formulation comprises about 185 mg of a filler. In some embodiments, the pharmaceutical formulation comprises about 190 mg of a filler. In some embodiments, the pharmaceutical formulation comprises about 195 mg of a filler. In some embodiments, the pharmaceutical formulation comprises about 200 mg of a filler.

In some embodiments, the pharmaceutical formulation comprises a disintegrant. In some embodiments, the disintegrant is selected from corn starch, potato starch, microcrystalline cellulose, methylcellulose, croscarmellose sodium, sodium starch glycolate, povidone, crospovidone, hypromellose, hydroxypropyl cellulose, polyvinyl alcohol, alginic acid, sodium alginate, agar, guar, locust bean, Karaya, pectin, tragacanth, bentonite, citrus pulp, and sodium lauryl sulfate. In some embodiments, the disintegrant is selected from povidone, crospovidone, hypromellose, croscarmellose sodium, hydroxypropyl cellulose, and polyvinyl alcohol. In some embodiments, the disintegrant is polyvinyl alcohol. In some embodiments, the disintegrant is hydroxypropyl cellulose. In some embodiments, the disintegrant is hypromellose. In some embodiments, the disintegrant is povidone. In some embodiments, the disintegrant is crospovidone. In some embodiments, the disintegrant is croscarmellose sodium. In some embodiments, the pharmaceutical formulation comprises about 3 mg to about 125 mg of the disintegrant. In some embodiments, the pharmaceutical formulation comprises about 3 mg to about 100 mg of the disintegrant. In some embodiments, the pharmaceutical formulation comprises about 3 mg to about 75 mg of the disintegrant. In some embodiments, the pharmaceutical formulation comprises about 3 mg to about 60 mg of the disintegrant. In some embodiments, the pharmaceutical formulation comprises about 3 mg to about 50 mg of the disintegrant. In some embodiments, the pharmaceutical formulation comprises about 4 mg to about 60 mg of the disintegrant. In some embodiments, the pharmaceutical formulation comprises about 4 mg to about 55 mg of the disintegrant. In some embodiments, the pharmaceutical formulation comprises about 4 mg to about 50 mg of the disintegrant. In some embodiments, the pharmaceutical formulation comprises about 5 mg to about 50 mg of the disintegrant. In some embodiments, the pharmaceutical formulation comprises about 5 mg to about 45 mg of the disintegrant. In some embodiments, the pharmaceutical formulation comprises about 5 mg to about 40 mg of the disintegrant. In some embodiments, the pharmaceutical formulation comprises about 5 mg to about 35 mg of the disintegrant. In some embodiments, the pharmaceutical formulation comprises about 5 mg to about 30 mg of the disintegrant. In some embodiments, the pharmaceutical formulation comprises about 6 mg to about 30 mg of the disintegrant. In some embodiments, the pharmaceutical formulation comprises about 5 mg of the disintegrant. In some embodiments, the pharmaceutical formulation comprises about 6 mg of the disintegrant. In some embodiments, the pharmaceutical formulation comprises about 7 mg of the disintegrant. In some embodiments, the pharmaceutical formulation comprises about 8 mg of the disintegrant. In some embodiments, the pharmaceutical formulation comprises about 9 mg of the disintegrant. In some embodiments, the pharmaceutical formulation comprises about 10 mg of the disintegrant. In some embodiments, the pharmaceutical formulation comprises about 12 mg of the disintegrant. In some embodiments, the pharmaceutical formulation comprises about 15 mg of the disintegrant. In some embodiments, the pharmaceutical formulation comprises about 20 mg of the disintegrant. In some embodiments, the pharmaceutical formulation comprises about 25 mg of the disintegrant. In some embodiments, the pharmaceutical formulation comprises about 30 mg of the disintegrant. In some embodiments, the pharmaceutical formulation comprises about 35 mg of the disintegrant. In some embodiments, the pharmaceutical formulation comprises about 40 mg of the disintegrant. In some embodiments, the pharmaceutical formulation comprises about 3 mg to about 150 mg of the disintegrant, wherein the disintegrant is crospovidone. In some embodiments, the pharmaceutical formulation comprises about 3 mg to about 100 mg of the disintegrant, wherein the disintegrant is crospovidone. In some embodiments, the pharmaceutical formulation comprises about 3 mg to about 75 mg of the disintegrant, wherein the disintegrant is crospovidone. In some embodiments, the pharmaceutical formulation comprises about 3 mg to about 60 mg of the disintegrant, wherein the disintegrant is crospovidone. In some embodiments, the pharmaceutical formulation comprises about 5 mg to about 50 mg of the disintegrant, wherein the disintegrant is crospovidone. In some embodiments, the pharmaceutical formulation comprises about 5 mg to about 40 mg of the disintegrant, wherein the disintegrant is crospovidone. In some embodiments, the pharmaceutical formulation comprises about 5 mg to about 35 mg of the disintegrant, wherein the disintegrant is crospovidone. In some embodiments, the pharmaceutical formulation comprises about 5 mg to about 30 mg of the disintegrant, wherein the disintegrant is crospovidone. In some embodiments, the pharmaceutical formulation comprises about 5 mg to about 30 mg of the disintegrant, wherein the disintegrant is crospovidone. In some embodiments, the pharmaceutical formulation comprises about 3 mg to about 100 mg of the disintegrant, wherein the disintegrant is croscarmellose sodium. In some embodiments, the pharmaceutical formulation comprises about 3 mg to about 75 mg of the disintegrant, wherein the disintegrant is croscarmellose sodium. In some embodiments, the pharmaceutical formulation comprises about 3 mg to about 60 mg of the disintegrant, wherein the disintegrant is croscarmellose sodium. In some embodiments, the pharmaceutical formulation comprises about 5 mg to about 50 mg of the disintegrant, wherein the disintegrant is croscarmellose sodium. In some embodiments, the pharmaceutical formulation comprises about 5 mg to about 40 mg of the disintegrant, wherein the disintegrant is croscarmellose sodium. In some embodiments, the pharmaceutical formulation comprises about 5 mg to about 35 mg of the disintegrant, wherein the disintegrant is croscarmellose sodium. In some embodiments, the pharmaceutical formulation comprises about 5 mg to about 30 mg of the disintegrant, wherein the disintegrant is croscarmellose sodium. In some embodiments, the pharmaceutical formulation comprises about 5 mg to about 30 mg of the disintegrant, wherein the disintegrant is croscarmellose sodium.

In some embodiments, the pharmaceutical formulation further comprises a lubricant. In some embodiments, the lubricant is selected from magnesium stearate, stearic acid, and sodium stearyl fumarate. In some embodiments, the lubricant is stearic acid. In some embodiments, the lubricant is sodium stearyl fumarate. In some embodiments, the pharmaceutical formulation comprises about 0.1 mg to about 8 mg of the lubricant. In some embodiments, the pharmaceutical formulation comprises about 0.1 mg to about 6 mg of the lubricant. In some embodiments, the pharmaceutical formulation comprises about 0.1 mg to about 5 mg of the lubricant. In some embodiments, the pharmaceutical formulation comprises about 0.1 mg to about 4 mg of the lubricant. In some embodiments, the pharmaceutical formulation comprises about 0.2 mg to about 10 mg of the lubricant. In some embodiments, the pharmaceutical formulation comprises about 0.2 mg to about 8 mg of the lubricant. In some embodiments, the pharmaceutical formulation comprises about 0.2 mg to about 7 mg of the lubricant. In some embodiments, the pharmaceutical formulation comprises about 0.2 mg to about 6 mg of the lubricant. In some embodiments, the pharmaceutical formulation comprises about 0.2 mg to about 5 mg of the lubricant. In some embodiments, the pharmaceutical formulation comprises about 0.2 mg to about 4 mg of the lubricant. In some embodiments, the pharmaceutical formulation comprises about 0.2 mg to about 3.5 mg of the lubricant. In some embodiments, the pharmaceutical formulation comprises about 0.2 mg to about 3 mg of the lubricant. In some embodiments, the pharmaceutical formulation comprises about 0.2 mg to about 2.5 mg of the lubricant. In some embodiments, the pharmaceutical formulation comprises about 0.2 mg to about 2 mg of the lubricant. In some embodiments, the pharmaceutical formulation comprises about 0.2 mg to about 1.5 mg of the lubricant. In some embodiments, the pharmaceutical formulation comprises about 0.3 mg to about 3 mg of the lubricant. In some embodiments, the pharmaceutical formulation comprises about 0.3 mg to about 2.5 mg of the lubricant. In some embodiments, the pharmaceutical formulation comprises about 0.3 mg to about 2 mg of the lubricant. In some embodiments, the pharmaceutical formulation comprises about 0.3 mg to about 1.5 mg of the lubricant. In some embodiments, the pharmaceutical formulation comprises about 0.3 mg to about 1 mg of the lubricant. In some embodiments, the pharmaceutical formulation comprises about 0.1 mg of the lubricant. In some embodiments, the pharmaceutical formulation comprises about 0.15 mg of the lubricant. In some embodiments, the pharmaceutical formulation comprises about 0.2 mg of the lubricant. In some embodiments, the pharmaceutical formulation comprises about 0.25 mg of the lubricant. In some embodiments, the pharmaceutical formulation comprises about 0.3 mg of the lubricant. In some embodiments, the pharmaceutical formulation comprises about 0.35 mg of the lubricant. In some embodiments, the pharmaceutical formulation comprises about 0.4 mg of the lubricant. In some embodiments, the pharmaceutical formulation comprises about 0.45 mg of the lubricant. In some embodiments, the pharmaceutical formulation comprises about 0.5 mg of the lubricant. In some embodiments, the pharmaceutical formulation comprises about 0.6 mg of the lubricant. In some embodiments, the pharmaceutical formulation comprises about 0.7 mg of the lubricant. In some embodiments, the pharmaceutical formulation comprises about 0.8 mg of the lubricant. In some embodiments, the pharmaceutical formulation comprises about 0.9 mg of the lubricant. In some embodiments, the pharmaceutical formulation comprises about 1 mg of the lubricant. In some embodiments, the pharmaceutical formulation comprises about 1.1 mg of the lubricant. In some embodiments, the pharmaceutical formulation comprises about 1.2 mg of the lubricant. In some embodiments, the pharmaceutical formulation comprises about 1.3 mg of the lubricant. In some embodiments, the pharmaceutical formulation comprises about 1.4 mg of the lubricant. In some embodiments, the pharmaceutical formulation comprises about 1.5 mg of the lubricant. In some embodiments, the pharmaceutical formulation comprises about 1.6 mg of the lubricant. In some embodiments, the pharmaceutical formulation comprises about 1.7 mg of the lubricant. In some embodiments, the pharmaceutical formulation comprises about 1.8 mg of the lubricant. In some embodiments, the pharmaceutical formulation comprises about 1.9 mg of the lubricant. In some embodiments, the pharmaceutical formulation comprises about 2 mg of the lubricant. In some embodiments, the pharmaceutical formulation comprises about 2.5 mg of the lubricant. In some embodiments, the pharmaceutical formulation comprises about 3 mg of the lubricant. In some embodiments, the pharmaceutical formulation comprises about 4 mg of the lubricant. In some embodiments, the pharmaceutical formulation comprises about 5 mg of the lubricant. In some embodiments, the pharmaceutical formulation comprises about 6 mg of the lubricant. In some embodiments, the pharmaceutical formulation comprises about 7 mg of the lubricant. In some embodiments, the pharmaceutical formulation comprises about 8 mg of the lubricant. In some embodiments, the pharmaceutical formulation comprises about 9 mg of the lubricant. In some embodiments, the pharmaceutical formulation comprises about 10 mg of the lubricant. In some embodiments, the pharmaceutical formulation comprises about 0.2 mg to about 10 mg of the lubricant, wherein the lubricant is sodium stearyl fumarate. In some embodiments, the pharmaceutical formulation comprises about 0.2 mg to about 5 mg of the lubricant, wherein the lubricant is sodium stearyl fumarate. In some embodiments, the pharmaceutical formulation comprises about 0.2 mg to about 4 mg of the lubricant, wherein the lubricant is sodium stearyl fumarate. In some embodiments, the pharmaceutical formulation comprises about 0.2 mg to about 3 mg of the lubricant, wherein the lubricant is sodium stearyl fumarate. In some embodiments, the pharmaceutical formulation comprises about 0.2 mg to about 2.5 mg of the lubricant, wherein the lubricant is sodium stearyl fumarate. In some embodiments, the pharmaceutical formulation comprises about 0.2 mg to about 2 mg of the lubricant, wherein the lubricant is sodium stearyl fumarate. In some embodiments, the pharmaceutical formulation comprises about 0.2 mg to about 1.5 mg of the lubricant, wherein the lubricant is sodium stearyl fumarate. In some embodiments, the pharmaceutical formulation comprises about 0.2 mg to about 1 mg of the lubricant, wherein the lubricant is sodium stearyl fumarate. In some embodiments, the pharmaceutical formulation comprises about 0.3 mg to about 4 mg of the lubricant, wherein the lubricant is sodium stearyl fumarate. In some embodiments, the pharmaceutical formulation comprises about 0.3 mg to about 3 mg of the lubricant, wherein the lubricant is sodium stearyl fumarate. In some embodiments, the pharmaceutical formulation comprises about 0.3 mg to about 2.5 mg of the lubricant, wherein the lubricant is sodium stearyl fumarate. In some embodiments, the pharmaceutical formulation comprises about 0.3 mg to about 2 mg of the lubricant, wherein the lubricant is sodium stearyl fumarate. In some embodiments, the pharmaceutical formulation comprises about 0.3 mg to about 1.5 mg of the lubricant, wherein the lubricant is sodium stearyl fumarate. In some embodiments, the pharmaceutical formulation comprises about 0.3 mg to about 1 mg of the lubricant, wherein the lubricant is sodium stearyl fumarate. In some embodiments, the pharmaceutical formulation comprises about 0.2 mg to about 10 mg of the lubricant, wherein the lubricant is magnesium stearate. In some embodiments, the pharmaceutical formulation comprises about 0.2 mg to about 5 mg of the lubricant, wherein the lubricant is magnesium stearate. In some embodiments, the pharmaceutical formulation comprises about 0.2 mg to about 4 mg of the lubricant, wherein the lubricant is magnesium stearate. In some embodiments, the pharmaceutical formulation comprises about 0.2 mg to about 3 mg of the lubricant, wherein the lubricant is magnesium stearate. In some embodiments, the pharmaceutical formulation comprises about 0.2 mg to about 2.5 mg of the lubricant, wherein the lubricant is magnesium stearate. In some embodiments, the pharmaceutical formulation comprises about 0.2 mg to about 2 mg of the lubricant, wherein the lubricant is magnesium stearate. In some embodiments, the pharmaceutical formulation comprises about 0.2 mg to about 1.5 mg of the lubricant, wherein the lubricant is magnesium stearate. In some embodiments, the pharmaceutical formulation comprises about 0.2 mg to about 1 mg of the lubricant, wherein the lubricant is magnesium stearate. In some embodiments, the pharmaceutical formulation comprises about 0.3 mg to about 4 mg of the lubricant, wherein the lubricant is magnesium stearate. In some embodiments, the pharmaceutical formulation comprises about 0.3 mg to about 3 mg of the lubricant, wherein the lubricant is magnesium stearate. In some embodiments, the pharmaceutical formulation comprises about 0.3 mg to about 2.5 mg of the lubricant, wherein the lubricant is magnesium stearate. In some embodiments, the pharmaceutical formulation comprises about 0.3 mg to about 2 mg of the lubricant, wherein the lubricant is magnesium stearate. In some embodiments, the pharmaceutical formulation comprises about 0.3 mg to about 1.5 mg of the lubricant, wherein the lubricant is magnesium stearate. In some embodiments, the pharmaceutical formulation comprises about 0.3 mg to about 1 mg of the lubricant, wherein the lubricant is magnesium stearate.

In some embodiments, the 1,1,1,3,3,3-hexafluoropropan-2-yl 4-(2-(pyrrolidin-1-yl)-4-(trifluoromethyl)benzyl)piperazine-1-carboxylate is in free base form. In some embodiments, the pharmaceutical formulation comprises about 1 mg to about 60 mg of 1,1,1,3,3,3-hexafluoropropan-2-yl 4-(2-(pyrrolidin-1-yl)-4-(trifluoromethyl)benzyl)piperazine-1-carboxylate free base. In some embodiments, the pharmaceutical formulation comprises about 1 mg to about 55 mg of 1,1,1,3,3,3-hexafluoropropan-2-yl 4-(2-(pyrrolidin-1-yl)-4-(trifluoromethyl)benzyl)piperazine-1-carboxylate free base. In some embodiments, the pharmaceutical formulation comprises about 1 mg to about 50 mg of 1,1,1,3,3,3-hexafluoropropan-2-yl 4-(2-(pyrrolidin-1-yl)-4-(trifluoromethyl)benzyl)piperazine-1-carboxylate free base. In some embodiments, the pharmaceutical formulation comprises about 1 mg to about 45 mg of 1,1,1,3,3,3-hexafluoropropan-2-yl 4-(2-(pyrrolidin-1-yl)-4-(trifluoromethyl)benzyl)piperazine-1-carboxylate free base. In some embodiments, the pharmaceutical formulation comprises about 1 mg to about 40 mg of 1,1,1,3,3,3-hexafluoropropan-2-yl 4-(2-(pyrrolidin-1-yl)-4-(trifluoromethyl)benzyl)piperazine-1-carboxylate free base. In some embodiments, the pharmaceutical formulation comprises about 1 mg to about 35 mg of 1,1,1,3,3,3-hexafluoropropan-2-yl 4-(2-(pyrrolidin-1-yl)-4-(trifluoromethyl)benzyl)piperazine-1-carboxylate free base. In some embodiments, the pharmaceutical formulation comprises about 1 mg to about 30 mg of 1,1,1,3,3,3-hexafluoropropan-2-yl 4-(2-(pyrrolidin-1-yl)-4-(trifluoromethyl)benzyl)piperazine-1-carboxylate free base. In some embodiments, the pharmaceutical formulation comprises about 1 mg to about 25 mg of 1,1,1,3,3,3-hexafluoropropan-2-yl 4-(2-(pyrrolidin-1-yl)-4-(trifluoromethyl)benzyl)piperazine-1-carboxylate free base. In some embodiments, the pharmaceutical formulation comprises about 1 mg to about 20 mg of 1,1,1,3,3,3-hexafluoropropan-2-yl 4-(2-(pyrrolidin-1-yl)-4-(trifluoromethyl)benzyl)piperazine-1-carboxylate free base. In some embodiments, the pharmaceutical formulation comprises about 1 mg to about 15 mg of 1,1,1,3,3,3-hexafluoropropan-2-yl 4-(2-(pyrrolidin-1-yl)-4-(trifluoromethyl)benzyl)piperazine-1-carboxylate free base. In some embodiments, the pharmaceutical formulation comprises about 1 mg to about 10 mg of 1,1,1,3,3,3-hexafluoropropan-2-yl 4-(2-(pyrrolidin-1-yl)-4-(trifluoromethyl)benzyl)piperazine-1-carboxylate free base. In some embodiments, the pharmaceutical formulation comprises about 2 mg to about 30 mg of 1,1,1,3,3,3-hexafluoropropan-2-yl 4-(2-(pyrrolidin-1-yl)-4-(trifluoromethyl)benzyl)piperazine-1-carboxylate free base. In some embodiments, the pharmaceutical formulation comprises about 2 mg to about 25 mg of 1,1,1,3,3,3-hexafluoropropan-2-yl 4-(2-(pyrrolidin-1-yl)-4-(trifluoromethyl)benzyl)piperazine-1-carboxylate free base. In some embodiments, the pharmaceutical formulation comprises about 2 mg to about 20 mg of 1,1,1,3,3,3-hexafluoropropan-2-yl 4-(2-(pyrrolidin-1-yl)-4-(trifluoromethyl)benzyl)piperazine-1-carboxylate free base. In some embodiments, the pharmaceutical formulation comprises about 2 mg to about 15 mg of 1,1,1,3,3,3-hexafluoropropan-2-yl 4-(2-(pyrrolidin-1-yl)-4-(trifluoromethyl)benzyl)piperazine-1-carboxylate free base. In some embodiments, the pharmaceutical formulation comprises about 2 mg to about 10 mg of 1,1,1,3,3,3-hexafluoropropan-2-yl 4-(2-(pyrrolidin-1-yl)-4-(trifluoromethyl)benzyl)piperazine-1-carboxylate free base. In some embodiments, the pharmaceutical formulation comprises about 1 mg of 1,1,1,3,3,3-hexafluoropropan-2-yl 4-(2-(pyrrolidin-1-yl)-4-(trifluoromethyl)benzyl)piperazine-1-carboxylate free base. In some embodiments, the pharmaceutical formulation comprises about 1.5 mg of 1,1,1,3,3,3-hexafluoropropan-2-yl 4-(2-(pyrrolidin-1-yl)-4-(trifluoromethyl)benzyl)piperazine-1-carboxylate free base. In some embodiments, the pharmaceutical formulation comprises about 2 mg of 1,1,1,3,3,3-hexafluoropropan-2-yl 4-(2-(pyrrolidin-1-yl)-4-(trifluoromethyl)benzyl)piperazine-1-carboxylate free base. In some embodiments, the pharmaceutical formulation comprises about 2.5 mg of 1,1,1,3,3,3-hexafluoropropan-2-yl 4-(2-(pyrrolidin-1-yl)-4-(trifluoromethyl)benzyl)piperazine-1-carboxylate free base. In some embodiments, the pharmaceutical formulation comprises about 3 mg of 1,1,1,3,3,3-hexafluoropropan-2-yl 4-(2-(pyrrolidin-1-yl)-4-(trifluoromethyl)benzyl)piperazine-1-carboxylate free base. In some embodiments, the pharmaceutical formulation comprises about 3.5 mg of 1,1,1,3,3,3-hexafluoropropan-2-yl 4-(2-(pyrrolidin-1-yl)-4-(trifluoromethyl)benzyl)piperazine-1-carboxylate free base. In some embodiments, the pharmaceutical formulation comprises about 4 mg of 1,1,1,3,3,3-hexafluoropropan-2-yl 4-(2-(pyrrolidin-1-yl)-4-(trifluoromethyl)benzyl)piperazine-1-carboxylate free base. In some embodiments, the pharmaceutical formulation comprises about 4.5 mg of 1,1,1,3,3,3-hexafluoropropan-2-yl 4-(2-(pyrrolidin-1-yl)-4-(trifluoromethyl)benzyl)piperazine-1-carboxylate free base. In some embodiments, the pharmaceutical formulation comprises about 5 mg of 1,1,1,3,3,3-hexafluoropropan-2-yl 4-(2-(pyrrolidin-1-yl)-4-(trifluoromethyl)benzyl)piperazine-1-carboxylate free base. In some embodiments, the pharmaceutical formulation comprises about 6 mg of 1,1,1,3,3,3-hexafluoropropan-2-yl 4-(2-(pyrrolidin-1-yl)-4-(trifluoromethyl)benzyl)piperazine-1-carboxylate free base. In some embodiments, the pharmaceutical formulation comprises about 7 mg of 1,1,1,3,3,3-hexafluoropropan-2-yl 4-(2-(pyrrolidin-1-yl)-4-(trifluoromethyl)benzyl)piperazine-1-carboxylate free base. In some embodiments, the pharmaceutical formulation comprises about 8 mg of 1,1,1,3,3,3-hexafluoropropan-2-yl 4-(2-(pyrrolidin-1-yl)-4-(trifluoromethyl)benzyl)piperazine-1-carboxylate free base. In some embodiments, the pharmaceutical formulation comprises about 9 mg of 1,1,1,3,3,3-hexafluoropropan-2-yl 4-(2-(pyrrolidin-1-yl)-4-(trifluoromethyl)benzyl)piperazine-1-carboxylate free base. In some embodiments, the pharmaceutical formulation comprises about 10 mg of 1,1,1,3,3,3-hexafluoropropan-2-yl 4-(2-(pyrrolidin-1-yl)-4-(trifluoromethyl)benzyl)piperazine-1-carboxylate free base. In some embodiments, the pharmaceutical formulation comprises about 11 mg of 1,1,1,3,3,3-hexafluoropropan-2-yl 4-(2-(pyrrolidin-1-yl)-4-(trifluoromethyl)benzyl)piperazine-1-carboxylate free base. In some embodiments, the pharmaceutical formulation comprises about 12 mg of 1,1,1,3,3,3-hexafluoropropan-2-yl 4-(2-(pyrrolidin-1-yl)-4-(trifluoromethyl)benzyl)piperazine-1-carboxylate free base. In some embodiments, the pharmaceutical formulation comprises about 13 mg of 1,1,1,3,3,3-hexafluoropropan-2-yl 4-(2-(pyrrolidin-1-yl)-4-(trifluoromethyl)benzyl)piperazine-1-carboxylate free base. In some embodiments, the pharmaceutical formulation comprises about 14 mg of 1,1,1,3,3,3-hexafluoropropan-2-yl 4-(2-(pyrrolidin-1-yl)-4-(trifluoromethyl)benzyl)piperazine-1-carboxylate free base. In some embodiments, the pharmaceutical formulation comprises about 15 mg of 1,1,1,3,3,3-hexafluoropropan-2-yl 4-(2-(pyrrolidin-1-yl)-4-(trifluoromethyl)benzyl)piperazine-1-carboxylate free base. In some embodiments, the pharmaceutical formulation comprises about 16 mg of 1,1,1,3,3,3-hexafluoropropan-2-yl 4-(2-(pyrrolidin-1-yl)-4-(trifluoromethyl)benzyl)piperazine-1-carboxylate free base. In some embodiments, the pharmaceutical formulation comprises about 17 mg of 1,1,1,3,3,3-hexafluoropropan-2-yl 4-(2-(pyrrolidin-1-yl)-4-(trifluoromethyl)benzyl)piperazine-1-carboxylate free base. In some embodiments, the pharmaceutical formulation comprises about 18 mg of 1,1,1,3,3,3-hexafluoropropan-2-yl 4-(2-(pyrrolidin-1-yl)-4-(trifluoromethyl)benzyl)piperazine-1-carboxylate free base. In some embodiments, the pharmaceutical formulation comprises about 19 mg of 1,1,1,3,3,3-hexafluoropropan-2-yl 4-(2-(pyrrolidin-1-yl)-4-(trifluoromethyl)benzyl)piperazine-1-carboxylate free base. In some embodiments, the pharmaceutical formulation comprises about 20 mg of 1,1,1,3,3,3-hexafluoropropan-2-yl 4-(2-(pyrrolidin-1-yl)-4-(trifluoromethyl)benzyl)piperazine-1-carboxylate free base. In some embodiments, the pharmaceutical formulation comprises about 25 mg of 1,1,1,3,3,3-hexafluoropropan-2-yl 4-(2-(pyrrolidin-1-yl)-4-(trifluoromethyl)benzyl)piperazine-1-carboxylate free base. In some embodiments, the pharmaceutical formulation comprises about 30 mg of 1,1,1,3,3,3-hexafluoropropan-2-yl 4-(2-(pyrrolidin-1-yl)-4-(trifluoromethyl)benzyl)piperazine-1-carboxylate free base. In some embodiments, the pharmaceutical formulation comprises about 35 mg of 1,1,1,3,3,3-hexafluoropropan-2-yl 4-(2-(pyrrolidin-1-yl)-4-(trifluoromethyl)benzyl)piperazine-1-carboxylate free base. In some embodiments, the pharmaceutical formulation comprises about 40 mg of 1,1,1,3,3,3-hexafluoropropan-2-yl 4-(2-(pyrrolidin-1-yl)-4-(trifluoromethyl)benzyl)piperazine-1-carboxylate free base. In some embodiments, the pharmaceutical formulation comprises about 45 mg of 1,1,1,3,3,3-hexafluoropropan-2-yl 4-(2-(pyrrolidin-1-yl)-4-(trifluoromethyl)benzyl)piperazine-1-carboxylate free base. In some embodiments, the pharmaceutical formulation comprises about 50 mg of 1,1,1,3,3,3-hexafluoropropan-2-yl 4-(2-(pyrrolidin-1-yl)-4-(trifluoromethyl)benzyl)piperazine-1-carboxylate free base. In some embodiments, the pharmaceutical formulation comprises about 55 mg of 1,1,1,3,3,3-hexafluoropropan-2-yl 4-(2-(pyrrolidin-1-yl)-4-(trifluoromethyl)benzyl)piperazine-1-carboxylate free base. In some embodiments, the pharmaceutical formulation comprises about 60 mg of 1,1,1,3,3,3-hexafluoropropan-2-yl 4-(2-(pyrrolidin-1-yl)-4-(trifluoromethyl)benzyl)piperazine-1-carboxylate free base.

In some embodiments, the 1,1,1,3,3,3-hexafluoropropan-2-yl 4-(2-(pyrrolidin-1-yl)-4-(trifluoromethyl)benzyl)piperazine-1-carboxylate is in a pharmaceutically acceptable salt form. In some embodiments, the 1,1,1,3,3,3-hexafluoropropan-2-yl 4-(2-(pyrrolidin-1-yl)-4-(trifluoromethyl)benzyl)piperazine-1-carboxylate is the 1,1,1,3,3,3-hexafluoropropan-2-yl 4-(2-(pyrrolidin-1-yl)-4-(trifluoromethyl)benzyl)piperazine-1-carboxylate hydrochloride salt. In some embodiments, the pharmaceutical formulation comprises about 1 mg to about 60 mg of 1,1,1,3,3,3-hexafluoropropan-2-yl 4-(2-(pyrrolidin-1-yl)-4-(trifluoromethyl)benzyl)piperazine-1-carboxylate hydrochloride salt. In some embodiments, the pharmaceutical formulation comprises about 1 mg to about 55 mg of 1,1,1,3,3,3-hexafluoropropan-2-yl 4-(2-(pyrrolidin-1-yl)-4-(trifluoromethyl)benzyl)piperazine-1-carboxylate hydrochloride salt. In some embodiments, the pharmaceutical formulation comprises about 1 mg to about 50 mg of 1,1,1,3,3,3-hexafluoropropan-2-yl 4-(2-(pyrrolidin-1-yl)-4-(trifluoromethyl)benzyl)piperazine-1-carboxylate hydrochloride salt. In some embodiments, the pharmaceutical formulation comprises about 1 mg to about 45 mg of 1,1,1,3,3,3-hexafluoropropan-2-yl 4-(2-(pyrrolidin-1-yl)-4-(trifluoromethyl)benzyl)piperazine-1-carboxylate hydrochloride salt. In some embodiments, the pharmaceutical formulation comprises about 1 mg to about 40 mg of 1,1,1,3,3,3-hexafluoropropan-2-yl 4-(2-(pyrrolidin-1-yl)-4-(trifluoromethyl)benzyl)piperazine-1-carboxylate hydrochloride salt. In some embodiments, the pharmaceutical formulation comprises about 1 mg to about 35 mg of 1,1,1,3,3,3-hexafluoropropan-2-yl 4-(2-(pyrrolidin-1-yl)-4-(trifluoromethyl)benzyl)piperazine-1-carboxylate hydrochloride salt. In some embodiments, the pharmaceutical formulation comprises about 1 mg to about 30 mg of 1,1,1,3,3,3-hexafluoropropan-2-yl 4-(2-(pyrrolidin-1-yl)-4-(trifluoromethyl)benzyl)piperazine-1-carboxylate hydrochloride salt. In some embodiments, the pharmaceutical formulation comprises about 1 mg to about 25 mg of 1,1,1,3,3,3-hexafluoropropan-2-yl 4-(2-(pyrrolidin-1-yl)-4-(trifluoromethyl)benzyl)piperazine-1-carboxylate hydrochloride salt. In some embodiments, the pharmaceutical formulation comprises about 1 mg to about 20 mg of 1,1,1,3,3,3-hexafluoropropan-2-yl 4-(2-(pyrrolidin-1-yl)-4-(trifluoromethyl)benzyl)piperazine-1-carboxylate hydrochloride salt. In some embodiments, the pharmaceutical formulation comprises about 1 mg to about 15 mg of 1,1,1,3,3,3-hexafluoropropan-2-yl 4-(2-(pyrrolidin-1-yl)-4-(trifluoromethyl)benzyl)piperazine-1-carboxylate hydrochloride salt. In some embodiments, the pharmaceutical formulation comprises about 1 mg to about 10 mg of 1,1,1,3,3,3-hexafluoropropan-2-yl 4-(2-(pyrrolidin-1-yl)-4-(trifluoromethyl)benzyl)piperazine-1-carboxylate hydrochloride salt. In some embodiments, the pharmaceutical formulation comprises about 2 mg to about 30 mg of 1,1,1,3,3,3-hexafluoropropan-2-yl 4-(2-(pyrrolidin-1-yl)-4-(trifluoromethyl)benzyl)piperazine-1-carboxylate hydrochloride salt. In some embodiments, the pharmaceutical formulation comprises about 2 mg to about 25 mg of 1,1,1,3,3,3-hexafluoropropan-2-yl 4-(2-(pyrrolidin-1-yl)-4-(trifluoromethyl)benzyl)piperazine-1-carboxylate hydrochloride salt. In some embodiments, the pharmaceutical formulation comprises about 2 mg to about 20 mg of 1,1,1,3,3,3-hexafluoropropan-2-yl 4-(2-(pyrrolidin-1-yl)-4-(trifluoromethyl)benzyl)piperazine-1-carboxylate hydrochloride salt. In some embodiments, the pharmaceutical formulation comprises about 2 mg to about 15 mg of 1,1,1,3,3,3-hexafluoropropan-2-yl 4-(2-(pyrrolidin-1-yl)-4-(trifluoromethyl)benzyl)piperazine-1-carboxylate hydrochloride salt. In some embodiments, the pharmaceutical formulation comprises about 2 mg to about 10 mg of 1,1,1,3,3,3-hexafluoropropan-2-yl 4-(2-(pyrrolidin-1-yl)-4-(trifluoromethyl)benzyl)piperazine-1-carboxylate hydrochloride salt. In some embodiments, the pharmaceutical formulation comprises about 1 mg of 1,1,1,3,3,3-hexafluoropropan-2-yl 4-(2-(pyrrolidin-1-yl)-4-(trifluoromethyl)benzyl)piperazine-1-carboxylate hydrochloride salt. In some embodiments, the pharmaceutical formulation comprises about 1.5 mg of 1,1,1,3,3,3-hexafluoropropan-2-yl 4-(2-(pyrrolidin-1-yl)-4-(trifluoromethyl)benzyl)piperazine-1-carboxylate hydrochloride salt. In some embodiments, the pharmaceutical formulation comprises about 2 mg of 1,1,1,3,3,3-hexafluoropropan-2-yl 4-(2-(pyrrolidin-1-yl)-4-(trifluoromethyl)benzyl)piperazine-1-carboxylate hydrochloride salt. In some embodiments, the pharmaceutical formulation comprises about 2.5 mg of 1,1,1,3,3,3-hexafluoropropan-2-yl 4-(2-(pyrrolidin-1-yl)-4-(trifluoromethyl)benzyl)piperazine-1-carboxylate hydrochloride salt. In some embodiments, the pharmaceutical formulation comprises about 3 mg of 1,1,1,3,3,3-hexafluoropropan-2-yl 4-(2-(pyrrolidin-1-yl)-4-(trifluoromethyl)benzyl)piperazine-1-carboxylate hydrochloride salt. In some embodiments, the pharmaceutical formulation comprises about 3.5 mg of 1,1,1,3,3,3-hexafluoropropan-2-yl 4-(2-(pyrrolidin-1-yl)-4-(trifluoromethyl)benzyl)piperazine-1-carboxylate hydrochloride salt. In some embodiments, the pharmaceutical formulation comprises about 4 mg of 1,1,1,3,3,3-hexafluoropropan-2-yl 4-(2-(pyrrolidin-1-yl)-4-(trifluoromethyl)benzyl)piperazine-1-carboxylate hydrochloride salt. In some embodiments, the pharmaceutical formulation comprises about 4.5 mg of 1,1,1,3,3,3-hexafluoropropan-2-yl 4-(2-(pyrrolidin-1-yl)-4-(trifluoromethyl)benzyl)piperazine-1-carboxylate hydrochloride salt. In some embodiments, the pharmaceutical formulation comprises about 5 mg of 1,1,1,3,3,3-hexafluoropropan-2-yl 4-(2-(pyrrolidin-1-yl)-4-(trifluoromethyl)benzyl)piperazine-1-carboxylate hydrochloride salt. In some embodiments, the pharmaceutical formulation comprises about 6 mg of 1,1,1,3,3,3-hexafluoropropan-2-yl 4-(2-(pyrrolidin-1-yl)-4-(trifluoromethyl)benzyl)piperazine-1-carboxylate hydrochloride salt. In some embodiments, the pharmaceutical formulation comprises about 7 mg of 1,1,1,3,3,3-hexafluoropropan-2-yl 4-(2-(pyrrolidin-1-yl)-4-(trifluoromethyl)benzyl)piperazine-1-carboxylate hydrochloride salt. In some embodiments, the pharmaceutical formulation comprises about 8 mg of 1,1,1,3,3,3-hexafluoropropan-2-yl 4-(2-(pyrrolidin-1-yl)-4-(trifluoromethyl)benzyl)piperazine-1-carboxylate hydrochloride salt. In some embodiments, the pharmaceutical formulation comprises about 9 mg of 1,1,1,3,3,3-hexafluoropropan-2-yl 4-(2-(pyrrolidin-1-yl)-4-(trifluoromethyl)benzyl)piperazine-1-carboxylate hydrochloride salt. In some embodiments, the pharmaceutical formulation comprises about 10 mg of 1,1,1,3,3,3-hexafluoropropan-2-yl 4-(2-(pyrrolidin-1-yl)-4-(trifluoromethyl)benzyl)piperazine-1-carboxylate hydrochloride salt. In some embodiments, the pharmaceutical formulation comprises about 11 mg of 1,1,1,3,3,3-hexafluoropropan-2-yl 4-(2-(pyrrolidin-1-yl)-4-(trifluoromethyl)benzyl)piperazine-1-carboxylate hydrochloride salt. In some embodiments, the pharmaceutical formulation comprises about 12 mg of 1,1,1,3,3,3-hexafluoropropan-2-yl 4-(2-(pyrrolidin-1-yl)-4-(trifluoromethyl)benzyl)piperazine-1-carboxylate hydrochloride salt. In some embodiments, the pharmaceutical formulation comprises about 13 mg of 1,1,1,3,3,3-hexafluoropropan-2-yl 4-(2-(pyrrolidin-1-yl)-4-(trifluoromethyl)benzyl)piperazine-1-carboxylate hydrochloride salt. In some embodiments, the pharmaceutical formulation comprises about 14 mg of 1,1,1,3,3,3-hexafluoropropan-2-yl 4-(2-(pyrrolidin-1-yl)-4-(trifluoromethyl)benzyl)piperazine-1-carboxylate hydrochloride salt. In some embodiments, the pharmaceutical formulation comprises about 15 mg of 1,1,1,3,3,3-hexafluoropropan-2-yl 4-(2-(pyrrolidin-1-yl)-4-(trifluoromethyl)benzyl)piperazine-1-carboxylate hydrochloride salt. In some embodiments, the pharmaceutical formulation comprises about 16 mg of 1,1,1,3,3,3-hexafluoropropan-2-yl 4-(2-(pyrrolidin-1-yl)-4-(trifluoromethyl)benzyl)piperazine-1-carboxylate hydrochloride salt. In some embodiments, the pharmaceutical formulation comprises about 17 mg of 1,1,1,3,3,3-hexafluoropropan-2-yl 4-(2-(pyrrolidin-1-yl)-4-(trifluoromethyl)benzyl)piperazine-1-carboxylate hydrochloride salt. In some embodiments, the pharmaceutical formulation comprises about 18 mg of 1,1,1,3,3,3-hexafluoropropan-2-yl 4-(2-(pyrrolidin-1-yl)-4-(trifluoromethyl)benzyl)piperazine-1-carboxylate hydrochloride salt. In some embodiments, the pharmaceutical formulation comprises about 19 mg of 1,1,1,3,3,3-hexafluoropropan-2-yl 4-(2-(pyrrolidin-1-yl)-4-(trifluoromethyl)benzyl)piperazine-1-carboxylate hydrochloride salt. In some embodiments, the pharmaceutical formulation comprises about 20 mg of 1,1,1,3,3,3-hexafluoropropan-2-yl 4-(2-(pyrrolidin-1-yl)-4-(trifluoromethyl)benzyl)piperazine-1-carboxylate hydrochloride salt. In some embodiments, the pharmaceutical formulation comprises about 25 mg of 1,1,1,3,3,3-hexafluoropropan-2-yl 4-(2-(pyrrolidin-1-yl)-4-(trifluoromethyl)benzyl)piperazine-1-carboxylate hydrochloride salt. In some embodiments, the pharmaceutical formulation comprises about 30 mg of 1,1,1,3,3,3-hexafluoropropan-2-yl 4-(2-(pyrrolidin-1-yl)-4-(trifluoromethyl)benzyl)piperazine-1-carboxylate hydrochloride salt. In some embodiments, the pharmaceutical formulation comprises about 35 mg of 1,1,1,3,3,3-hexafluoropropan-2-yl 4-(2-(pyrrolidin-1-yl)-4-(trifluoromethyl)benzyl)piperazine-1-carboxylate hydrochloride salt. In some embodiments, the pharmaceutical formulation comprises about 40 mg of 1,1,1,3,3,3-hexafluoropropan-2-yl 4-(2-(pyrrolidin-1-yl)-4-(trifluoromethyl)benzyl)piperazine-1-carboxylate hydrochloride salt. In some embodiments, the pharmaceutical formulation comprises about 45 mg of 1,1,1,3,3,3-hexafluoropropan-2-yl 4-(2-(pyrrolidin-1-yl)-4-(trifluoromethyl)benzyl)piperazine-1-carboxylate hydrochloride salt. In some embodiments, the pharmaceutical formulation comprises about 50 mg of 1,1,1,3,3,3-hexafluoropropan-2-yl 4-(2-(pyrrolidin-1-yl)-4-(trifluoromethyl)benzyl)piperazine-1-carboxylate hydrochloride salt. In some embodiments, the pharmaceutical formulation comprises about 55 mg of 1,1,1,3,3,3-hexafluoropropan-2-yl 4-(2-(pyrrolidin-1-yl)-4-(trifluoromethyl)benzyl)piperazine-1-carboxylate hydrochloride salt. In some embodiments, the pharmaceutical formulation comprises about 60 mg of 1,1,1,3,3,3-hexafluoropropan-2-yl 4-(2-(pyrrolidin-1-yl)-4-(trifluoromethyl)benzyl)piperazine-1-carboxylate hydrochloride salt.

In some embodiments, the 1,1,1,3,3,3-hexafluoropropan-2-yl 4-(2-(pyrrolidin-1-yl)-4-(trifluoromethyl)benzyl)piperazine-1-carboxylate is the 1,1,1,3,3,3-hexafluoropropan-2-yl 4-(2-(pyrrolidin-1-yl)-4-(trifluoromethyl)benzyl)piperazine-1-carboxylate fumarate salt. In some embodiments, the pharmaceutical formulation comprises about 1 mg to about 60 mg of 1,1,1,3,3,3-hexafluoropropan-2-yl 4-(2-(pyrrolidin-1-yl)-4-(trifluoromethyl)benzyl)piperazine-1-carboxylate fumarate salt. In some embodiments, the pharmaceutical formulation comprises about 1 mg to about 55 mg of 1,1,1,3,3,3-hexafluoropropan-2-yl 4-(2-(pyrrolidin-1-yl)-4-(trifluoromethyl)benzyl)piperazine-1-carboxylate fumarate salt. In some embodiments, the pharmaceutical formulation comprises about 1 mg to about 50 mg of 1,1,1,3,3,3-hexafluoropropan-2-yl 4-(2-(pyrrolidin-1-yl)-4-(trifluoromethyl)benzyl)piperazine-1-carboxylate fumarate salt. In some embodiments, the pharmaceutical formulation comprises about 1 mg to about 45 mg of 1,1,1,3,3,3-hexafluoropropan-2-yl 4-(2-(pyrrolidin-1-yl)-4-(trifluoromethyl)benzyl)piperazine-1-carboxylate fumarate salt. In some embodiments, the pharmaceutical formulation comprises about 1 mg to about 40 mg of 1,1,1,3,3,3-hexafluoropropan-2-yl 4-(2-(pyrrolidin-1-yl)-4-(trifluoromethyl)benzyl)piperazine-1-carboxylate fumarate salt. In some embodiments, the pharmaceutical formulation comprises about 1 mg to about 35 mg of 1,1,1,3,3,3-hexafluoropropan-2-yl 4-(2-(pyrrolidin-1-yl)-4-(trifluoromethyl)benzyl)piperazine-1-carboxylate fumarate salt. In some embodiments, the pharmaceutical formulation comprises about 1 mg to about 30 mg of 1,1,1,3,3,3-hexafluoropropan-2-yl 4-(2-(pyrrolidin-1-yl)-4-(trifluoromethyl)benzyl)piperazine-1-carboxylate fumarate salt. In some embodiments, the pharmaceutical formulation comprises about 1 mg to about 25 mg of 1,1,1,3,3,3-hexafluoropropan-2-yl 4-(2-(pyrrolidin-1-yl)-4-(trifluoromethyl)benzyl)piperazine-1-carboxylate fumarate salt. In some embodiments, the pharmaceutical formulation comprises about 1 mg to about 20 mg of 1,1,1,3,3,3-hexafluoropropan-2-yl 4-(2-(pyrrolidin-1-yl)-4-(trifluoromethyl)benzyl)piperazine-1-carboxylate fumarate salt. In some embodiments, the pharmaceutical formulation comprises about 1 mg to about 15 mg of 1,1,1,3,3,3-hexafluoropropan-2-yl 4-(2-(pyrrolidin-1-yl)-4-(trifluoromethyl)benzyl)piperazine-1-carboxylate fumarate salt. In some embodiments, the pharmaceutical formulation comprises about 1 mg to about 10 mg of 1,1,1,3,3,3-hexafluoropropan-2-yl 4-(2-(pyrrolidin-1-yl)-4-(trifluoromethyl)benzyl)piperazine-1-carboxylate fumarate salt. In some embodiments, the pharmaceutical formulation comprises about 2 mg to about 30 mg of 1,1,1,3,3,3-hexafluoropropan-2-yl 4-(2-(pyrrolidin-1-yl)-4-(trifluoromethyl)benzyl)piperazine-1-carboxylate fumarate salt. In some embodiments, the pharmaceutical formulation comprises about 2 mg to about 25 mg of 1,1,1,3,3,3-hexafluoropropan-2-yl 4-(2-(pyrrolidin-1-yl)-4-(trifluoromethyl)benzyl)piperazine-1-carboxylate fumarate salt. In some embodiments, the pharmaceutical formulation comprises about 2 mg to about 20 mg of 1,1,1,3,3,3-hexafluoropropan-2-yl 4-(2-(pyrrolidin-1-yl)-4-(trifluoromethyl)benzyl)piperazine-1-carboxylate fumarate salt. In some embodiments, the pharmaceutical formulation comprises about 2 mg to about 15 mg of 1,1,1,3,3,3-hexafluoropropan-2-yl 4-(2-(pyrrolidin-1-yl)-4-(trifluoromethyl)benzyl)piperazine-1-carboxylate fumarate salt. In some embodiments, the pharmaceutical formulation comprises about 2 mg to about 10 mg of 1,1,1,3,3,3-hexafluoropropan-2-yl 4-(2-(pyrrolidin-1-yl)-4-(trifluoromethyl)benzyl)piperazine-1-carboxylate fumarate salt. In some embodiments, the pharmaceutical formulation comprises about 1 mg of 1,1,1,3,3,3-hexafluoropropan-2-yl 4-(2-(pyrrolidin-1-yl)-4-(trifluoromethyl)benzyl)piperazine-1-carboxylate fumarate salt. In some embodiments, the pharmaceutical formulation comprises about 1.5 mg of 1,1,1,3,3,3-hexafluoropropan-2-yl 4-(2-(pyrrolidin-1-yl)-4-(trifluoromethyl)benzyl)piperazine-1-carboxylate fumarate salt. In some embodiments, the pharmaceutical formulation comprises about 2 mg of 1,1,1,3,3,3-hexafluoropropan-2-yl 4-(2-(pyrrolidin-1-yl)-4-(trifluoromethyl)benzyl)piperazine-1-carboxylate fumarate salt. In some embodiments, the pharmaceutical formulation comprises about 2.5 mg of 1,1,1,3,3,3-hexafluoropropan-2-yl 4-(2-(pyrrolidin-1-yl)-4-(trifluoromethyl)benzyl)piperazine-1-carboxylate fumarate salt. In some embodiments, the pharmaceutical formulation comprises about 3 mg of 1,1,1,3,3,3-hexafluoropropan-2-yl 4-(2-(pyrrolidin-1-yl)-4-(trifluoromethyl)benzyl)piperazine-1-carboxylate fumarate salt. In some embodiments, the pharmaceutical formulation comprises about 3.5 mg of 1,1,1,3,3,3-hexafluoropropan-2-yl 4-(2-(pyrrolidin-1-yl)-4-(trifluoromethyl)benzyl)piperazine-1-carboxylate fumarate salt. In some embodiments, the pharmaceutical formulation comprises about 4 mg of 1,1,1,3,3,3-hexafluoropropan-2-yl 4-(2-(pyrrolidin-1-yl)-4-(trifluoromethyl)benzyl)piperazine-1-carboxylate fumarate salt. In some embodiments, the pharmaceutical formulation comprises about 4.5 mg of 1,1,1,3,3,3-hexafluoropropan-2-yl 4-(2-(pyrrolidin-1-yl)-4-(trifluoromethyl)benzyl)piperazine-1-carboxylate fumarate salt. In some embodiments, the pharmaceutical formulation comprises about 5 mg of 1,1,1,3,3,3-hexafluoropropan-2-yl 4-(2-(pyrrolidin-1-yl)-4-(trifluoromethyl)benzyl)piperazine-1-carboxylate fumarate salt. In some embodiments, the pharmaceutical formulation comprises about 6 mg of 1,1,1,3,3,3-hexafluoropropan-2-yl 4-(2-(pyrrolidin-1-yl)-4-(trifluoromethyl)benzyl)piperazine-1-carboxylate fumarate salt. In some embodiments, the pharmaceutical formulation comprises about 7 mg of 1,1,1,3,3,3-hexafluoropropan-2-yl 4-(2-(pyrrolidin-1-yl)-4-(trifluoromethyl)benzyl)piperazine-1-carboxylate fumarate salt. In some embodiments, the pharmaceutical formulation comprises about 8 mg of 1,1,1,3,3,3-hexafluoropropan-2-yl 4-(2-(pyrrolidin-1-yl)-4-(trifluoromethyl)benzyl)piperazine-1-carboxylate fumarate salt. In some embodiments, the pharmaceutical formulation comprises about 9 mg of 1,1,1,3,3,3-hexafluoropropan-2-yl 4-(2-(pyrrolidin-1-yl)-4-(trifluoromethyl)benzyl)piperazine-1-carboxylate fumarate salt. In some embodiments, the pharmaceutical formulation comprises about 10 mg of 1,1,1,3,3,3-hexafluoropropan-2-yl 4-(2-(pyrrolidin-1-yl)-4-(trifluoromethyl)benzyl)piperazine-1-carboxylate fumarate salt. In some embodiments, the pharmaceutical formulation comprises about 11 mg of 1,1,1,3,3,3-hexafluoropropan-2-yl 4-(2-(pyrrolidin-1-yl)-4-(trifluoromethyl)benzyl)piperazine-1-carboxylate fumarate salt. In some embodiments, the pharmaceutical formulation comprises about 12 mg of 1,1,1,3,3,3-hexafluoropropan-2-yl 4-(2-(pyrrolidin-1-yl)-4-(trifluoromethyl)benzyl)piperazine-1-carboxylate fumarate salt. In some embodiments, the pharmaceutical formulation comprises about 13 mg of 1,1,1,3,3,3-hexafluoropropan-2-yl 4-(2-(pyrrolidin-1-yl)-4-(trifluoromethyl)benzyl)piperazine-1-carboxylate fumarate salt. In some embodiments, the pharmaceutical formulation comprises about 14 mg of 1,1,1,3,3,3-hexafluoropropan-2-yl 4-(2-(pyrrolidin-1-yl)-4-(trifluoromethyl)benzyl)piperazine-1-carboxylate fumarate salt. In some embodiments, the pharmaceutical formulation comprises about 15 mg of 1,1,1,3,3,3-hexafluoropropan-2-yl 4-(2-(pyrrolidin-1-yl)-4-(trifluoromethyl)benzyl)piperazine-1-carboxylate fumarate salt. In some embodiments, the pharmaceutical formulation comprises about 16 mg of 1,1,1,3,3,3-hexafluoropropan-2-yl 4-(2-(pyrrolidin-1-yl)-4-(trifluoromethyl)benzyl)piperazine-1-carboxylate fumarate salt. In some embodiments, the pharmaceutical formulation comprises about 17 mg of 1,1,1,3,3,3-hexafluoropropan-2-yl 4-(2-(pyrrolidin-1-yl)-4-(trifluoromethyl)benzyl)piperazine-1-carboxylate fumarate salt. In some embodiments, the pharmaceutical formulation comprises about 18 mg of 1,1,1,3,3,3-hexafluoropropan-2-yl 4-(2-(pyrrolidin-1-yl)-4-(trifluoromethyl)benzyl)piperazine-1-carboxylate fumarate salt. In some embodiments, the pharmaceutical formulation comprises about 19 mg of 1,1,1,3,3,3-hexafluoropropan-2-yl 4-(2-(pyrrolidin-1-yl)-4-(trifluoromethyl)benzyl)piperazine-1-carboxylate fumarate salt. In some embodiments, the pharmaceutical formulation comprises about 20 mg of 1,1,1,3,3,3-hexafluoropropan-2-yl 4-(2-(pyrrolidin-1-yl)-4-(trifluoromethyl)benzyl)piperazine-1-carboxylate fumarate salt. In some embodiments, the pharmaceutical formulation comprises about 25 mg of 1,1,1,3,3,3-hexafluoropropan-2-yl 4-(2-(pyrrolidin-1-yl)-4-(trifluoromethyl)benzyl)piperazine-1-carboxylate fumarate salt. In some embodiments, the pharmaceutical formulation comprises about 30 mg of 1,1,1,3,3,3-hexafluoropropan-2-yl 4-(2-(pyrrolidin-1-yl)-4-(trifluoromethyl)benzyl)piperazine-1-carboxylate fumarate salt. In some embodiments, the pharmaceutical formulation comprises about 35 mg of 1,1,1,3,3,3-hexafluoropropan-2-yl 4-(2-(pyrrolidin-1-yl)-4-(trifluoromethyl)benzyl)piperazine-1-carboxylate fumarate salt. In some embodiments, the pharmaceutical formulation comprises about 40 mg of 1,1,1,3,3,3-hexafluoropropan-2-yl 4-(2-(pyrrolidin-1-yl)-4-(trifluoromethyl)benzyl)piperazine-1-carboxylate fumarate salt. In some embodiments, the pharmaceutical formulation comprises about 45 mg of 1,1,1,3,3,3-hexafluoropropan-2-yl 4-(2-(pyrrolidin-1-yl)-4-(trifluoromethyl)benzyl)piperazine-1-carboxylate fumarate salt. In some embodiments, the pharmaceutical formulation comprises about 50 mg of 1,1,1,3,3,3-hexafluoropropan-2-yl 4-(2-(pyrrolidin-1-yl)-4-(trifluoromethyl)benzyl)piperazine-1-carboxylate fumarate salt. In some embodiments, the pharmaceutical formulation comprises about 55 mg of 1,1,1,3,3,3-hexafluoropropan-2-yl 4-(2-(pyrrolidin-1-yl)-4-(trifluoromethyl)benzyl)piperazine-1-carboxylate fumarate salt. In some embodiments, the pharmaceutical formulation comprises about 60 mg of 1,1,1,3,3,3-hexafluoropropan-2-yl 4-(2-(pyrrolidin-1-yl)-4-(trifluoromethyl)benzyl)piperazine-1-carboxylate fumarate salt.

Synthesis of Pharmaceutical Formulations

The pharmaceutical formulations described herein, comprise 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt thereof, and pharmaceutically acceptable excipients. In some embodiments, the pharmaceutical formulations described herein are made by a hot melt extrusion process. In some embodiments, 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt thereof, a polymeric carrier, surfactant, and glidant were uniformly mixed and then extruded at elevated temperature to provide an amorphous solid dispersion of 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt thereof. In some embodiments, 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt thereof, a polymeric carrier, plasticizer, surfactant, and glidant were uniformly mixed and then extruded at elevated temperature to provide an amorphous solid dispersion of 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt thereof. In some embodiments, 1,1,1,3,3,3-hexafluoropropan-2-yl 4-(2-(pyrrolidin-1-yl)-4-(trifluoromethyl)benzyl)piperazine-1-carboxylate hydrochloride salt, a polymeric carrier, surfactant, glidant, and potassium dihydrogen phosphate were uniformly mixed and then extruded at elevated temperature to provide an amorphous solid dispersion of 1,1,1,3,3,3-hexafluoropropan-2-yl 4-(2-(pyrrolidin-1-yl)-4-(trifluoromethyl)benzyl)piperazine-1-carboxylate hydrochloride salt. In some embodiments, 1,1,1,3,3,3-hexafluoropropan-2-yl 4-(2-(pyrrolidin-1-yl)-4-(trifluoromethyl)benzyl)piperazine-1-carboxylate hydrochloride salt, a polymeric carrier, plasticizer, surfactant, glidant, and potassium dihydrogen phosphate were uniformly mixed and then extruded at elevated temperature to provide an amorphous solid dispersion of 1,1,1,3,3,3-hexafluoropropan-2-yl 4-(2-(pyrrolidin-1-yl)-4-(trifluoromethyl)benzyl)piperazine-1-carboxylate hydrochloride salt. In some embodiments, an amorphous solid dispersion of 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt thereof, is blended with a filler, a disintegrant, and a lubricant and compressed to form tablets of 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt thereof.

In some embodiments, the pharmaceutical formulation contains between about 1 mg to about 60 mg of 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt thereof, per tablet. In some embodiments, the pharmaceutical formulation contains between about 1 mg to about 55 mg of 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt thereof, per tablet. In some embodiments, the pharmaceutical formulation contains between about 1 mg to about 50 mg of 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt thereof, per tablet. In some embodiments, the pharmaceutical formulation contains between about 1 mg to about 45 mg of 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt thereof, per tablet. In some embodiments, the pharmaceutical formulation contains between about 1 mg to about 40 mg of 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt thereof, per tablet. In some embodiments, the pharmaceutical formulation contains between about 1 mg to about 35 mg of 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt thereof, per tablet. In some embodiments, the pharmaceutical formulation contains between about 1 mg to about 30 mg of 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt thereof, per tablet. In some embodiments, the pharmaceutical formulation contains between about 1 mg to about 25 mg of 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt thereof, per tablet. In some embodiments, the pharmaceutical formulation contains between about 1 mg to about 20 mg of 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt thereof, per tablet. In some embodiments, the pharmaceutical formulation contains between about 1 mg to about 15 mg of 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt thereof, per tablet. In some embodiments, the pharmaceutical formulation contains between about 1 mg to about 10 mg of 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt thereof, per tablet. In some embodiments, the pharmaceutical formulation contains between about 2 mg to about 30 mg of 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt thereof, per tablet. In some embodiments, the pharmaceutical formulation contains between about 2 mg to about 25 mg of 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt thereof, per tablet. In some embodiments, the pharmaceutical formulation contains between about 2 mg to about 20 mg of 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt thereof, per tablet. In some embodiments, the pharmaceutical formulation contains between about 2 mg to about 15 mg of 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt thereof, per tablet. In some embodiments, the pharmaceutical formulation contains between about 2 mg to about 10 mg of 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt thereof, per tablet. In some embodiments, the pharmaceutical formulation contains about 1 mg of 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt thereof, per tablet. In some embodiments, the pharmaceutical formulation contains about 1.5 mg of 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt thereof, per tablet. In some embodiments, the pharmaceutical formulation contains about 2 mg of 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt thereof, per tablet. In some embodiments, the pharmaceutical formulation contains about 2.5 mg of 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt thereof, per tablet. In some embodiments, the pharmaceutical formulation contains about 3 mg of 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt thereof, per tablet. In some embodiments, the pharmaceutical formulation contains about 3.5 mg of 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt thereof, per tablet. In some embodiments, the pharmaceutical formulation contains about 4 mg of 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt thereof, per tablet. In some embodiments, the pharmaceutical formulation contains about 4.5 mg of 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt thereof, per tablet. In some embodiments, the pharmaceutical formulation contains about 5 mg of 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt thereof, per tablet. In some embodiments, the pharmaceutical formulation contains about 6 mg of 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt thereof, per tablet. In some embodiments, the pharmaceutical formulation contains about 7 mg of 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt thereof, per tablet. In some embodiments, the pharmaceutical formulation contains about 8 mg of 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt thereof, per tablet. In some embodiments, the pharmaceutical formulation contains about 9 mg of 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt thereof, per tablet. In some embodiments, the pharmaceutical formulation contains about 10 mg of 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt thereof, per tablet. In some embodiments, the pharmaceutical formulation contains about 11 mg of 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt thereof, per tablet. In some embodiments, the pharmaceutical formulation contains about 12 mg of 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt thereof, per tablet. In some embodiments, the pharmaceutical formulation contains about 13 mg of 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt thereof, per tablet. In some embodiments, the pharmaceutical formulation contains about 14 mg of 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt thereof, per tablet. In some embodiments, the pharmaceutical formulation contains about 15 mg of 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt thereof, per tablet.

In some embodiments, the pharmaceutical formulation contains between about 1 mg to about 60 mg of 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt thereof, per caplet. In some embodiments, the pharmaceutical formulation contains between about 1 mg to about 55 mg of 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt thereof, per caplet. In some embodiments, the pharmaceutical formulation contains between about 1 mg to about 50 mg of 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt thereof, per caplet. In some embodiments, the pharmaceutical formulation contains between about 1 mg to about 45 mg of 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt thereof, per caplet. In some embodiments, the pharmaceutical formulation contains between about 1 mg to about 40 mg of 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt thereof, per caplet. In some embodiments, the pharmaceutical formulation contains between about 1 mg to about 35 mg of 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt thereof, per caplet. In some embodiments, the pharmaceutical formulation contains between about 1 mg to about 30 mg of 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt thereof, per caplet. In some embodiments, the pharmaceutical formulation contains between about 1 mg to about 25 mg of 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt thereof, per caplet. In some embodiments, the pharmaceutical formulation contains between about 1 mg to about 20 mg of 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt thereof, per caplet. In some embodiments, the pharmaceutical formulation contains between about 1 mg to about 15 mg of 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt thereof, per caplet. In some embodiments, the pharmaceutical formulation contains between about 1 mg to about 10 mg of 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt thereof, per caplet. In some embodiments, the pharmaceutical formulation contains between about 2 mg to about 30 mg of 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt thereof, per caplet. In some embodiments, the pharmaceutical formulation contains between about 2 mg to about 25 mg of 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt thereof, per caplet. In some embodiments, the pharmaceutical formulation contains between about 2 mg to about 20 mg of 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt thereof, per caplet. In some embodiments, the pharmaceutical formulation contains between about 2 mg to about 15 mg of 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt thereof, per caplet. In some embodiments, the pharmaceutical formulation contains between about 2 mg to about 10 mg of 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt thereof, per caplet. In some embodiments, the pharmaceutical formulation contains about 1 mg of 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt thereof, per caplet. In some embodiments, the pharmaceutical formulation contains about 1.5 mg of 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt thereof, per caplet. In some embodiments, the pharmaceutical formulation contains about 2 mg of 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt thereof, per caplet. In some embodiments, the pharmaceutical formulation contains about 2.5 mg of 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt thereof, per caplet. In some embodiments, the pharmaceutical formulation contains about 3 mg of 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt thereof, per caplet. In some embodiments, the pharmaceutical formulation contains about 3.5 mg of 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt thereof, per caplet. In some embodiments, the pharmaceutical formulation contains about 4 mg of 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt thereof, per caplet. In some embodiments, the pharmaceutical formulation contains about 4.5 mg of 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt thereof, per caplet. In some embodiments, the pharmaceutical formulation contains about 5 mg of 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt thereof, per caplet. In some embodiments, the pharmaceutical formulation contains about 6 mg of 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt thereof, per caplet. In some embodiments, the pharmaceutical formulation contains about 7 mg of 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt thereof, per caplet. In some embodiments, the pharmaceutical formulation contains about 8 mg of 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt thereof, per caplet. In some embodiments, the pharmaceutical formulation contains about 9 mg of 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt thereof, per caplet. In some embodiments, the pharmaceutical formulation contains about 10 mg of 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt thereof, per caplet. In some embodiments, the pharmaceutical formulation contains about 11 mg of 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt thereof, per caplet. In some embodiments, the pharmaceutical formulation contains about 12 mg of 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt thereof, per caplet. In some embodiments, the pharmaceutical formulation contains about 13 mg of 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt thereof, per caplet. In some embodiments, the pharmaceutical formulation contains about 14 mg of 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt thereof, per caplet. In some embodiments, the pharmaceutical formulation contains about 15 mg of 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt thereof, per caplet.

In some embodiments, the pharmaceutical formulation contains between about 1 mg to about 60 mg of 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt thereof, per capsule. In some embodiments, the pharmaceutical formulation contains between about 1 mg to about 55 mg of 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt thereof, per capsule. In some embodiments, the pharmaceutical formulation contains between about 1 mg to about 50 mg of 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt thereof, per capsule. In some embodiments, the pharmaceutical formulation contains between about 1 mg to about 45 mg of 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt thereof, per capsule. In some embodiments, the pharmaceutical formulation contains between about 1 mg to about 40 mg of 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt thereof, per capsule. In some embodiments, the pharmaceutical formulation contains between about 1 mg to about 35 mg of 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt thereof, per capsule. In some embodiments, the pharmaceutical formulation contains between about 1 mg to about 30 mg of 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt thereof, per capsule. In some embodiments, the pharmaceutical formulation contains between about 1 mg to about 25 mg of 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt thereof, per capsule. In some embodiments, the pharmaceutical formulation contains between about 1 mg to about 20 mg of 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt thereof, per capsule. In some embodiments, the pharmaceutical formulation contains between about 1 mg to about 15 mg of 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt thereof, per capsule. In some embodiments, the pharmaceutical formulation contains between about 1 mg to about 10 mg of 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt thereof, per capsule. In some embodiments, the pharmaceutical formulation contains between about 2 mg to about 30 mg of 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt thereof, per capsule. In some embodiments, the pharmaceutical formulation contains between about 2 mg to about 25 mg of 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt thereof, per capsule. In some embodiments, the pharmaceutical formulation contains between about 2 mg to about 20 mg of 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt thereof, per capsule. In some embodiments, the pharmaceutical formulation contains between about 2 mg to about 15 mg of 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt thereof, per capsule. In some embodiments, the pharmaceutical formulation contains between about 2 mg to about 10 mg of 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt thereof, per capsule. In some embodiments, the pharmaceutical formulation contains about 1 mg of 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt thereof, per capsule. In some embodiments, the pharmaceutical formulation contains about 1.5 mg of 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt thereof, per capsule. In some embodiments, the pharmaceutical formulation contains about 2 mg of 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt thereof, per capsule. In some embodiments, the pharmaceutical formulation contains about 2.5 mg of 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt thereof, per capsule. In some embodiments, the pharmaceutical formulation contains about 3 mg of 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt thereof, per capsule. In some embodiments, the pharmaceutical formulation contains about 3.5 mg of 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt thereof, per capsule. In some embodiments, the pharmaceutical formulation contains about 4 mg of 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt thereof, per capsule. In some embodiments, the pharmaceutical formulation contains about 4.5 mg of 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt thereof, per capsule. In some embodiments, the pharmaceutical formulation contains about 5 mg of 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt thereof, per capsule. In some embodiments, the pharmaceutical formulation contains about 6 mg of 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt thereof, per capsule. In some embodiments, the pharmaceutical formulation contains about 7 mg of 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt thereof, per capsule. In some embodiments, the pharmaceutical formulation contains about 8 mg of 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt thereof, per capsule. In some embodiments, the pharmaceutical formulation contains about 9 mg of 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt thereof, per capsule. In some embodiments, the pharmaceutical formulation contains about 10 mg of 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt thereof, per capsule. In some embodiments, the pharmaceutical formulation contains about 11 mg of 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt thereof, per capsule. In some embodiments, the pharmaceutical formulation contains about 12 mg of 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt thereof, per capsule. In some embodiments, the pharmaceutical formulation contains about 13 mg of 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt thereof, per capsule. In some embodiments, the pharmaceutical formulation contains about 14 mg of 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt thereof, per capsule. In some embodiments, the pharmaceutical formulation contains about 15 mg of 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt thereof, per capsule.

Excipients

Suitable optional excipients for use in the 1,1,1,3,3,3-hexafluoropropan-2-yl 4-(2-(pyrrolidin-1-yl)-4-(trifluoromethyl)benzyl)piperazine-1-carboxylate pharmaceutical formulations described herein include any commonly used excipients in pharmaceutics and are selected on the basis of compatibility with the active pharmaceutical agent and the release profile properties of the desired dosage form. Excipients include, but are not limited to, binders, fillers, flow aids, disintegrants, lubricants, glidants, polymeric carriers, plasticizers, stabilizers, surfactants, and the like. A summary of excipients described herein, may be found, for example in *Remington: The Science and Practice of Pharmacy*, Nineteenth Ed (Easton, Pa.: Mack Publishing Company, 1995); Hoover, John E., *Remington's Pharmaceutical Sciences*, Mack Publishing Co., Easton, Pa. 1975; Liberman, H. A. and Lachman, L., Eds., *Pharmaceutical Dosage Forms*, Marcel Decker, New York, N.Y., 1980; and *Pharmaceutical Dosage Forms and Drug Delivery Systems*, Seventh Ed. (Lippincott Williams & Wilkins, 1999), herein incorporated by reference in their entirety.

Binders impart cohesiveness to solid oral dosage form formulations: for powder filled capsule formulation, they aid in plug formation that can be filled into soft or hard shell capsules and for tablet formulation, they ensure the tablet remaining intact after compression and help assure blend uniformity prior to a compression or fill step. Materials suitable for use as binders in the solid dosage forms described herein include, but are not limited to, carboxymethylcellulose, methylcellulose (e.g., Methocel®), hydroxypropylmethylcellulose (e.g. Hypromellose USP Pharmacoat-603, hydroxypropylmethylcellulose acetate stearate (Aqoate HS-LF and HS), hydroxyethylcellulose, hydroxypropyl cellulose (e.g., Klucel®), ethylcellulose (e.g., Ethocel®), and microcrystalline cellulose (e.g., Avicel®), microcrystalline dextrose, amylose, magnesium aluminum silicate, polysaccharide acids, bentonites, gelatin, polyvinyl pyrrolidone/vinyl acetate copolymer, crospovidone, povidone, starch, pregelatinized starch, tragacanth, dextrin, a sugar, such as sucrose (e.g., Dipac®), glucose, dextrose, molasses, mannitol, sorbitol, xylitol (e.g., Xylitab®), lactose, a natural or synthetic gum such as acacia, tragacanth, ghatti gum, mucilage of isapol husks, starch, polyvinyl pyrrolidone (e.g., Povidone® CL, Kollidon® CL, Polyplasdone® XL-10, and Povidone® K-12), larch arabogalactan, Veegum®, polyethylene glycol, waxes, sodium alginate, and the like. In some embodiments, the binder is hypromellose, hydroxypropyl cellulose, or ethyl cellulose. In some embodiments, the binder is hypromellose. In some embodiments, the binder is hydroxypropyl cellulose. In some embodiments, the binder is ethyl cellulose.

Fillers or diluents increase bulk in the pharmaceutical formulation. Such compounds include e.g., lactose; starch; mannitol; sorbitol; dextrose; microcrystalline cellulose such as Avicel®; dibasic calcium phosphate; dicalcium phosphate dihydrate; tricalcium phosphate; calcium phosphate; anhydrous lactose; spray-dried lactose; pregelatinzed starch; compressible sugar, such as Di-Pac® (Amstar); hydroxypropylmethylcellulose; sucrose-based diluents; confectioner's sugar; monobasic calcium sulfate monohydrate; calcium sulfate dihydrate; calcium lactate trihydrate; dextrates; hydrolyzed cereal solids; amylose; powdered cellulose; calcium carbonate; glycine; kaolin; sodium chloride; inositol; bentonite; and the like. In some embodiments of the pharmaceutical formulations described herein, the filler is lactose, mannitol, or microcrystalline cellulose. In some embodiments, the filler is lactose. In some embodiments, the filler is mannitol. In some embodiments, the filler is dicalcium phosphate. In some embodiments, the filler is microcrystalline cellulose. In some embodiments, the filler is silicified microcrystalline cellulose. In some embodiments, the filler is starch. In some embodiments, the filler is pregelatinized starch (Starch 1500).

Glidants improve the flow characteristics of a powder mixtures. Such compounds include, e.g., colloidal silicon dioxide such as Cab-o-sil®; tribasic calcium phosphate, talc, corn starch, DL-leucine, sodium lauryl sulfate, magnesium stearate, calcium stearate, sodium stearate, kaolin, and micronized amorphous silicon dioxide (Syloid®) and the like. In some embodiments of the pharmaceutical formulations described herein, the glidant is colloidal silicon dioxide or talc. In some embodiments, the glidant is talc. In some embodiments, the glidant is colloidal silicon dioxide.

Lubricants are compounds which prevent, reduce, or inhibit adhesion or friction of materials. Exemplary lubricants include, e.g., stearic acid; calcium hydroxide, talc; a hydrocarbon such as mineral oil, or hydrogenated vegetable oil such as hydrogenated soybean oil (Sterotex®), Lubritab®, Cutina®; higher fatty acids and their alkali-metal and alkaline earth metal salts, such as aluminum, calcium, magnesium, zinc, stearic acid, sodium stearates, magnesium stearate, glycerol, talc, waxes, Stearowet®, boric acid, sodium acetate, leucine, a polyethylene glycol or a methoxypolyethylene glycol such as Carbowax™, sodium oleate, glyceryl behenate (Compitrol 888®), glyceryl palmitostearate (Precirol®), colloidal silica such as Syloid™, Carb-O-Sil®, a starch such as corn starch, silicone oil, a surfactant, and the like. Hydrophilic lubricants include, e.g., sodium stearyl fumarate (currently marketed under the trade name PRUV®), polyethylene glycol (PEG), magnesium lauryl sulfate, sodium lauryl sulfate (SLS), sodium benzoate, sodium chloride, and the like. In some embodiments of the pharmaceutical formulations described herein, the lubricant is magnesium stearate, stearic acid, or sodium stearyl fumarate. In some embodiments, the lubricant is stearic acid. In some embodiments, the lubricant is sodium stearyl fumarate. In some embodiments, the lubricant is magnesium stearate.

Disintegrants facilitate breakup or disintegration of the pharmaceutical formulation after administration. Examples of disintegrants include a starch, e.g., a natural starch such as corn starch or potato starch, a pregelatinized starch such as National 1551 or Amijel®, or sodium starch glycolate such as Promogel® or Explotab®; a cellulose such as a wood product, microcrystalline cellulose, e.g., Avicel®, Avicel® PH101, Avicel® PH102, Avicel® PH105, Elcema® P100, Emcocel®, Vivacel®, Ming Tia®, and Solka-Floc®, methylcellulose, croscarmellose, or a cross-linked cellulose, such as cross-linked sodium carboxymethylcellulose (Ac-Di-Sol®), cross-linked carboxymethylcellulose, or cross-linked croscarmellose; a cross-linked starch such as sodium starch glycolate; a cross-linked polymer such as crospovidone; a cross-linked polyvinyl pyrrolidone; alginate such as alginic acid or a salt of alginic acid such as sodium alginate; a clay such as Veegum® HV (magnesium aluminum silicate); a gum such as agar, guar, locust bean, Karaya, pectin, or tragacanth; sodium starch glycolate; bentonite; a natural sponge; a resin such as a cation-exchange resin; citrus pulp;

sodium lauryl sulfate; sodium lauryl sulfate in combination starch; and the like. In some embodiments of the pharmaceutical formulations described herein, the disintegrant is povidone, crospovidone, hypromellose, hydroxypropyl cellulose, or polyvinyl alcohol. In some embodiments, the disintegrant is polyvinyl alcohol. In some embodiments, the disintegrant is hydroxypropyl cellulose. In some embodiments, the disintegrant is hypromellose. In some embodiments, the disintegrant is povidone. In some embodiments, the disintegrant is crospovidone.

Polymeric carriers include compounds such as polyvinyl pyrrolidone, e.g., polyvinylpolyvinyl pyrrolidone K12, polyvinyl pyrrolidone K17, polyvinyl pyrrolidone K25, or polyvinyl pyrrolidone K30, polyvinyl pyrrolidone vinyl acetate (PVPVA 64), hydroxypropylmethyl cellulose (HPMC), hydroxypropylmethylcellulose acetylsuccinate (HPMC AS), and methylmethacrylate polymers (Eudragit polymers) and the like.

In some embodiments, the pharmaceutical formulations described herein include one or more pH-adjusting agents or buffering agents. In some embodiments, the pharmaceutical formulation comprises a buffer selected from acetates, carbonates, phosphates, citrates, and glutamates. In some embodiments, the buffer is selected from potassium dihydrogen phosphate, sodium bicarbonate, magnesium carbonate, sodium citrate, sodium dihydrogen phosphate, dipotassium monohydrogen phosphate, and disodium monohydrogen phosphate. In some embodiments, buffers are included in an amount required to maintain pH of the pharmaceutical formulation in an acceptable range.

In some embodiments, a film coating is provided around the pharmaceutical composition. In some embodiments, the coating of 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt thereof, is an immediate release coating. In some embodiments, the immediate release coating comprises hydroxypropyl methyl cellulose (HPMC), with or without plasticizer, and with or without surfactants and anti-foaming agents (clear or pigmented or dyed). In some embodiments, the coating of 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt thereof, is an immediate release coating with a moisture barrier. In some embodiments, the film coating is Opadry AMB II Beige. In some embodiments, the immediate release coating with a moisture barrier comprises polyvinyl alcohol (PVA), with or without plasticizer, with or without surfactants and anti-foaming agents (clear or pigmented or dyed). In some embodiments, the compositions are formulated into particles (for example for administration by capsule) and some or all of the particles are coated. In some embodiments, the compositions are formulated into particles (for example, for administration by capsule) and some or all of the particles are microencapsulated. In some embodiments, the compositions are formulated into particles (for example, for administration by capsule) and some or all of the particles are not microencapsulated and are uncoated.

In some embodiments, the formulations described herein are delivered using a pulsatile dosage form. A pulsatile dosage form is capable of providing one or more immediate release pulses at predetermined time points after a controlled lag time or at specific sites. Many other types of controlled release systems known to those of ordinary skill in the art and are suitable for use with the formulations described herein. Examples of such delivery systems include, e.g., polymer-based systems, such as polylactic and polyglycolic acid, polyanhydrides and polycaprolactone; porous matrices, nonpolymer-based systems that are lipids, including sterols, such as cholesterol, cholesterol esters and fatty acids, or neutral fats, such as mono-, di- and triglycerides; hydrogel release systems; silastic systems; peptide-based systems; wax coatings, bioerodible dosage forms, compressed tablets using conventional binders and the like. See, e.g., Liberman et al., *Pharmaceutical Dosage Forms*, $2^{nd}$ Ed., Vol. 1, pp. 209-214 (1990); Singh et al., *Encyclopedia of Pharmaceutical Technology*, $2^{nd}$ Ed., pp. 751-753 (2002); U.S. Pat. Nos. 4,327,725, 4,624,848, 4,968,509, 5,461,140, 5,456,923, 5,516,527, 5,622,721, 5,686,105, 5,700,410, 5,977,175, 6,465,014, and 6,932,983, each of which is specifically incorporated by reference.

Stabilizers include compounds such as any anti-oxidation agents, e.g., butylated hydroxytoluene (BHT), sodium ascorbate, and tocopherol; buffers, acids, and the like.

Surfactants include compounds such as sodium lauryl sulfate, sorbitan monooleate, polyoxyethylene sorbitan monooleate, polysorbates, polaxomers, bile salts, glyceryl monostearate, copolymers of ethylene oxide and propylene oxide, e.g., Pluronic® (BASF), d-α-tocopheryl polyethylene glycol succinate (Vitamin E TPGS); and the like.

The aforementioned excipients are given as examples only and are not meant to include all possible choices. Other suitable excipient classes include coloring agents, granulating agents, preservatives, anti-foaming agents, plasticizers, and the like. Additionally, many excipients can have more than one role or function, or can be classified in more than one group; the classifications are descriptive only, and are not intended to limit any use of a particular excipient.

Dosage Forms

In some embodiments, the 1,1,1,3,3,3-hexafluoropropan-2-yl 4-(2-(pyrrolidin-1-yl)-4-(trifluoromethyl)benzyl)piperazine-1-carboxylate pharmaceutical formulations described herein are incorporated into a solid unit dosage form. The term "solid unit dosage form" means a dosage form intended to be swallowed as a single unit that is selected from the group consisting of a powder, a tablet, a bite-disintegration tablet, a chewable tablet, a caplet, a capsule, a gelcap, an effervescent powder, a rapid-disintegration tablet, an abuse-deterrent tablet, a modified release tablet, a modified release caplet, a modified release capsule, and an aqueous suspension produced from a powder. In some embodiments, the solid unit dosage form is a tablet. In some embodiments, the solid unit dosage form is a caplet. In some embodiments, the solid unit dosage forms are selected from the group consisting of soft capsules or hard capsules of any size or shape. In some embodiments, the solid unit dosage forms are soft capsules of any size or shape. In some embodiments, the solid unit dosage forms are hard capsules of any size or shape. Suitable capsules include, but are not limited to, spherical or elliptical soft elastic gelatin capsules; starch, cellulose or gelatin hard capsules such as Capill®, and the like. Appropriate capsule sizes include capsule sizes 000, 00EL, 00, 0EL, 0, 1, 2, 3, 4, or 5.

Self-emulsifying drug delivery systems (SEDDS), as well as self-microemulsifying drug delivery systems (SMEDDS) and self-nanoemulsifying drug delivery systems (SNEDDS) form fine oil-in-water dispersions (emulsion, microemulsion, and nanoemulsion, respectively) upon dilution with aqueous media or in contact with gastrointestinal fluids. In some embodiments, the pharmaceutical formulations described herein comprise a self-emulsifying drug delivery system. In some embodiments, the pharmaceutical formulations described herein comprise a self-microemulsifying drug delivery system. In some embodiments, the pharmaceutical formulations described herein comprise a self-nanoemulsifying drug delivery system.

Methods

In some embodiments, the 1,1,1,3,3,3-hexafluoropropan-2-yl 4-(2-(pyrrolidin-1-yl)-4-(trifluoromethyl)benzyl)piperazine-1-carboxylate pharmaceutical formulations described herein modulate the activity of MAGL. Contemplated methods, for example, comprise exposing said enzyme to a pharmaceutical formulation described herein. The ability of pharmaceutical formulations described herein to modulate or inhibit MAGL is evaluated by procedures known in the art and/or described herein. Another aspect of this disclosure provides methods of treating a disease associated with expression or activity of MAGL in a patient.

Also disclosed herein are methods of treating and/or preventing in a patient in need thereof a disorder such as one or more of acute or chronic pain and neuropathy. Disclosed methods include administering a pharmaceutically effective amount of a pharmaceutical formulation described herein.

In another embodiment is a method of treating pain in a patient, comprising administering a therapeutically effective amount of a pharmaceutical formulation described herein, to a patient in need thereof to treat said pain. In another embodiment is a method of treating neuropathic pain in a patient, comprising administering a therapeutically effective amount of a pharmaceutical formulation described herein, to a patient in need thereof to treat said neuropathic pain. In another embodiment is a method of treating inflammatory pain in a patient, comprising administering a therapeutically effective amount of a pharmaceutical formulation described herein, to a patient in need thereof to treat said inflammatory pain. In another embodiment is a method of treating complex regional pain syndrome in a patient in need thereof comprising administering to the patient a therapeutically effective amount of a pharmaceutical formulation described herein.

In another embodiment is a method of treating a disease or disorder in a patient comprising administering to the patient in need thereof a therapeutically effective amount of a pharmaceutical formulation described herein, wherein the disease or disorder is selected from the group consisting of epilepsy/seizure disorder, multiple sclerosis, neuromyelitis optica (NMO), Tourette syndrome, Alzheimer's disease, and abdominal pain associated with irritable bowel syndrome. In another embodiment is a method of treating epilepsy/seizure disorder in a patient comprising administering to the patient in need thereof a therapeutically effective amount of a pharmaceutical formulation described herein. In another embodiment is a method of treating multiple sclerosis in a patient comprising administering to the patient in need thereof a therapeutically effective amount of a pharmaceutical formulation described herein. In another embodiment is a method of treating neuromyelitis optica (NMO) in a patient comprising administering to the patient in need thereof a therapeutically effective amount of a pharmaceutical formulation described herein. In another embodiment is a method of treating Tourette syndrome in a patient comprising administering to the patient in need thereof a therapeutically effective amount of a pharmaceutical formulation described herein. In another embodiment is a method of treating Alzheimer's disease in a patient comprising administering to the patient in need thereof a therapeutically effective amount of a pharmaceutical formulation described herein. In another embodiment is a method of treating abdominal pain associated with irritable bowel syndrome in a patient comprising administering to the patient in need thereof a therapeutically effective amount of a pharmaceutical formulation described herein.

In another embodiment is a method of treating acute pain, inflammatory pain, cancer pain, pain caused by peripheral neuropathy, central pain, fibromyalgia, migraine, vasoocclussive painful crises in sickle cell disease, spasticity or pain associated with multiple sclerosis, functional chest pain, rheumatoid arthritis, osteoarthritis, or functional dyspepsia in a patient in need thereof, comprising administering to the patient a therapeutically effective amount of a pharmaceutical formulation described herein. In another embodiment is a method of treating acute pain in a patient in need thereof, comprising administering to the patient a therapeutically effective amount of a pharmaceutical formulation described herein. In another embodiment is a method of treating inflammatory pain in a patient in need thereof, comprising administering to the patient a therapeutically effective amount of a pharmaceutical formulation described herein. In another embodiment is a method of treating cancer pain in a patient in need thereof, comprising administering to the patient a therapeutically effective amount of a pharmaceutical formulation described herein. In another embodiment is a method of treating pain caused by peripheral neuropathy in a patient in need thereof, comprising administering to the patient a therapeutically effective amount of a pharmaceutical formulation described herein. In another embodiment is a method of treating central pain in a patient in need thereof, comprising administering to the patient a therapeutically effective amount of a pharmaceutical formulation described herein. In another embodiment is a method of treating fibromyalgia in a patient in need thereof, comprising administering to the patient a therapeutically effective amount of a pharmaceutical formulation described herein. In another embodiment is a method of treating migraine in a patient in need thereof, comprising administering to the patient a therapeutically effective amount of a pharmaceutical formulation described herein. In another embodiment is a method of treating vasoocclussive painful crises in sickle cell disease in a patient in need thereof, comprising administering to the patient a therapeutically effective amount of a pharmaceutical formulation described herein. In another embodiment is a method of treating spasticity or pain associated with multiple sclerosis in a patient in need thereof, comprising administering to the patient a therapeutically effective amount of a pharmaceutical formulation described herein. In another embodiment is a method of treating functional chest pain in a patient in need thereof, comprising administering to the patient a therapeutically effective amount of a pharmaceutical formulation described herein. In another embodiment is a method of treating rheumatoid arthritis in a patient in need thereof, comprising administering to the patient a therapeutically effective amount of a pharmaceutical formulation described herein. In another embodiment is a method of treating osteoarthritis in a patient in need thereof, comprising administering to the patient a therapeutically effective amount of a pharmaceutical formulation described herein. In another embodiment is a method of treating functional dyspepsia in a patient in need thereof, comprising administering to the patient a therapeutically effective amount of a pharmaceutical formulation described herein.

In some embodiments, disclosed herein is a method of treating Persistent Motor Tic Disorder in a patient in need thereof, comprising administering to the patient a therapeutically effective amount of a pharmaceutical formulation described herein. In some embodiments, disclosed herein is a method of treating Persistent Vocal Tic Disorder in a patient in need thereof, comprising administering to the patient a therapeutically effective amount of a pharmaceutical formulation described herein.

In some embodiments, disclosed herein is a method of treating attention deficit and hyperactivity disorder (ADHD) in a patient in need thereof, comprising administering to the patient a therapeutically effective amount of a pharmaceutical formulation described herein. In some embodiments, disclosed herein is a method of treating obsessive-compulsive disorder (OCD) in a patient in need thereof, comprising administering to the patient a therapeutically effective amount of a pharmaceutical formulation described herein.

In another embodiment is a method of lowering intraocular eye pressure (IOP) in a patient in need thereof, comprising administering to the patient a therapeutically effective amount of a pharmaceutical formulation described herein. In another embodiment is a method of treating glaucoma in a patient in need thereof, comprising administering to the patient a therapeutically effective amount of a pharmaceutical formulation described herein.

In another embodiment is a method of treating atopic dermatitis in a patient in need thereof, comprising administering to the patient a therapeutically effective amount of a pharmaceutical formulation described herein.

In another embodiment is a method of treating pruritis in a patient in need thereof, comprising administering to the patient a therapeutically effective amount of a pharmaceutical formulation described herein.

In another embodiment is a method of treating Down's syndrome in a patient in need thereof, comprising administering to the patient a therapeutically effective amount of a pharmaceutical formulation described herein.

In some embodiments, disclosed herein is a method of synergistically potentiating the activity of an opioid analgesic in a patient being treated with an opioid analgesic, comprising administering to the patient a therapeutically effective amount of a pharmaceutical formulation described herein. In some embodiments, disclosed herein is a method of reducing the acute side-effects associated with an opioid analgesic in a patient being treated with an opioid analgesic, comprising administering to the patient a therapeutically effective amount of a pharmaceutical formulation described herein.

In another embodiment is a method of treating dystonia in a patient in need thereof, comprising administering to the patient a therapeutically effective amount of a pharmaceutical formulation described herein.

In some embodiments, disclosed herein is a method of treating Amyotrophic Lateral Sclerosis (ALS) or ALS-related symptoms in a patient in need thereof, comprising administering to the patient a therapeutically effective amount of a pharmaceutical formulation described herein.

In some embodiments, disclosed herein is a method of treating agitation in autism in a patient in need thereof, comprising administering to the patient a therapeutically effective amount of a pharmaceutical formulation described herein.

In another embodiment is a method of treating sleep disturbance or bladder dysfunction associated with multiple sclerosis in a patient in need thereof, comprising administering to the patient a therapeutically effective amount of a pharmaceutical formulation described herein.

In some embodiments, disclosed herein is a method of treating Huntington's Disease in a patient in need thereof, comprising administering to the patient a therapeutically effective amount of a pharmaceutical formulation described herein.

In some embodiments, disclosed herein is a method of Parkinson's Disease in a patient in need thereof, comprising administering to the patient a therapeutically effective amount of a pharmaceutical formulation described herein.

In some embodiments, disclosed herein is a method of improving functional outcome following stroke in a patient in need thereof, comprising administering to the patient a therapeutically effective amount of a pharmaceutical formulation described herein.

In some embodiments, disclosed herein is a method of treating traumatic brain injury in a patient in need thereof, comprising administering to the patient a therapeutically effective amount of a pharmaceutical formulation described herein.

In some embodiments, disclosed herein is a method of treating trigeminal neuralgia in a patient in need thereof, comprising administering to the patient a therapeutically effective amount of a pharmaceutical formulation described herein. In some embodiments, disclosed herein is a method of treating glossopharyngeal neuralgia in a patient in need thereof, comprising administering to the patient a therapeutically effective amount of a pharmaceutical formulation described herein.

Disclosed pharmaceutical formulations are administered to patients (animals and humans) in need of such treatment in dosages that will provide optimal pharmaceutical efficacy. It will be appreciated that the dose required for use in any particular application will vary from patient to patient, not only with the particular pharmaceutical formulation selected, but also with the nature of the condition being treated, the age and condition of the patient, concurrent medication or special diets then being followed by the patient, and other factors, with the appropriate dosage ultimately being at the discretion of the attendant physician.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

EXAMPLES

The following examples provide illustrative methods for making exemplary 1,1,1,3,3,3-hexafluoropropan-2-yl 4-(2-(pyrrolidin-1-yl)-4-(trifluoromethyl)benzyl)piperazine-1-carboxylate pharmaceutical formulations. These examples are provided for illustrative purposes only and not to limit the scope of the claims provided herein.

Example 1: Pharmaceutical Formulation 1,1,1,3,3,3-Hexafluoropropan-2-yl 4-(2-(pyrrolidin-1-yl)-4-(trifluoromethyl)benzyl)piperazine-1-carboxylate hydrochloride; Tablets, 10 mg of HCl salt per tablet:

| Component | mg/unit | % |
|---|---|---|
| 1,1,1,3,3,3-Hexafluoropropan-2-yl 4-(2-(pyrrolidin-1-yl)-4-(trifluoromethyl)benzyl)piperazine-1-carboxylate hydrochloride | 10 | 3.33 |
| Polyvinyl pyrrolidone K30 (PVP K30) | 72.1 | 24.03 |
| PEG 400 | 12.9 | 4.3 |
| Polysorbate 80 (Tween 80) | 2 | 0.67 |

-continued

| Component | mg/unit | % |
|---|---|---|
| Silicon dioxide | 2 | 0.67 |
| Potassium dihydrogen phosphate | 1 | 0.33 |
| Microcrystalline cellulose 102 | 168.5 | 56.17 |
| Crospovidone | 30 | 10 |
| Sodium stearyl fumarate | 1.5 | 0.5 |
| Total: | 300 | 100.00 |

1,1,1,3,3,3-Hexafluoropropan-2-yl 4-(2-(pyrrolidin-1-yl)-4-(trifluoromethyl)benzyl)piperazine-1-carboxylate hydrochloride; Tablets, 10 mg of free base per tablet:

| Component | mg/unit | % |
|---|---|---|
| 1,1,1,3,3,3-Hexafluoropropan-2-yl 4-(2-(pyrrolidin-1-yl)-4-(trifluoromethyl)benzyl)piperazine-1-carboxylate hydrochloride | 10.72[1] | 1.4 |
| Polyvinyl pyrrolidone K30 (PVP K30) | 76 | 10.1 |
| PEG 400 | 8 | 1.07 |
| Polysorbate 80 (Tween 80) | 2 | 0.27 |
| Silicon dioxide | 2 | 0.27 |
| Potassium dihydrogen phosphate | 2 | 0.27 |
| Microcrystalline cellulose 102 | 608.8 | 81.17 |
| Croscarmellose Sodium | 37.5 | 5.0 |
| Sodium stearyl fumarate | 3.75 | 0.5 |
| Total: | 750.00 | 100.00 |

[1]10.72 mg 1,1,1,3,3,3-hexafluoropropan-2-yl 4-(2-(pyrrolidin-1-yl)-4-(trifluoromethyl)benzyl)piperazine-1-carboxylate hydrochloride drug substance is stoichiometrically equivalent to 10.00 mg 1,1,1,3,3,3-hexafluoropropan-2-yl 4-(2-(pyrrolidin-1-yl)-4-(trifluoromethyl)benzyl)piperazine-1-carboxylate as free base 1,1,1,3,3,3-Hexafluoropropan-2-yl 4-(2-(pyrrolidin-1-yl)-4-(trifluoromethyl)benzyl)piperazine-1-carboxylate hydrochloride, polyvinyl pyrrolidone K30 (PVP K30), potassium dihydrogen phosphate, PEG 400 and polysorbate 80 (Tween 80) were mixed to get a uniform mixture. The mixture was blended with silicon dioxide to get a free flowing blend. The blend was extruded using a twin screw extruder. The extrudate was then milled. The milled extrudate was blended with microcrystalline cellulose 102, crospovidone or croscarmellose sodium, and sodium stearyl fumarate to obtain a uniform tablet blend. The tablet blend was compressed into tablets.

Example 2: Pharmaceutical Formulation 1,1,1,3,3,3-Hexafluoropropan-2-yl 4-(2-(pyrrolidin-1-yl)-4-(trifluoromethyl)benzyl)piperazine-1-carboxylate hydrochloride; Tablets, 10 mg of HCl salt per tablet:

| Component | mg/unit | % |
|---|---|---|
| 1,1,1,3,3,3-Hexafluoropropan-2-yl 4-(2-(pyrrolidin-1-yl)-4-(trifluoromethyl)benzyl)piperazine-1-carboxylate hydrochloride | 10 | 3.33 |
| Polyvinyl pyrrolidone vinyl acetate (PVPVA 64) | 85 | 28.33 |
| Polysorbate 80 (Tween 80) | 2 | 0.67 |
| Silicon dioxide | 2 | 0.67 |
| Potassium dihydrogen phosphate | 1 | 0.33 |
| Microcrystalline cellulose 102 | 168.5 | 56.17 |
| Crospovidone | 30 | 10 |
| Sodium stearyl fumarate | 1.5 | 0.5 |
| Total: | 300 | 100.00 |

1,1,1,3,3,3-Hexafluoropropan-2-yl 4-(2-(pyrrolidin-1-yl)-4-(trifluoromethyl)benzyl)piperazine-1-carboxylate hydrochloride, polyvinyl pyrrolidone vinyl acetate (PVPVA 64), potassium dihydrogen phosphate, and polysorbate 80 (Tween 80) were mixed to get a uniform mixture. The mixture was blended with silicon dioxide to get a free flowing blend. The blend was extruded using a twin screw extruder. The extrudate was then milled. The milled extrudate was blended with microcrystalline cellulose 102, crospovidone, and sodium stearyl fumarate to obtain a uniform tablet blend. The tablet blend was compressed into tablets.

Example 3: Pharmaceutical Formulation 1,1,1,3,3,3-Hexafluoropropan-2-yl 4-(2-(pyrrolidin-1-yl)-4-(trifluoromethyl)benzyl)piperazine-1-carboxylate hydrochloride; Capsules, 2, 10, and 50 mg (amount of free base per capsule):

| Ingredient | 2 mg Capsule % (w/w) | 2 mg Capsule mg | 10 mg Capsule % (w/w) | 10 mg Capsule mg | 50 mg Capsule % (w/w) | 50 mg Capsule mg |
|---|---|---|---|---|---|---|
| 1,1,1,3,3,3-Hexafluoropropan-2-yl 4-(2-(pyrrolidin-1-yl)-4-(trifluoromethyl)benzyl)piperazine-1-carboxylate hydrochloride | 1.26 | 2.14[1] | 6.31 | 10.72[2] | 31.53 | 53.60[3] |
| Microcrystalline Cellulose | 91.74 | 155.96 | 86.69 | 147.38 | 61.47 | 104.5 |
| Croscarmellose Sodium | 6.00 | 10.20 | 6.00 | 10.20 | 6.00 | 10.20 |
| Magnesium Stearate | 1.00 | 1.70 | 1.00 | 1.700 | 1.00 | 1.700 |
| Total Fill | 100.0 | 170.0 | 100.0 | 170.0 | 100.0 | 170.0 |

[1]2.14 mg 1,1,1,3,3,3-hexafluoropropan-2-yl 4-(2-(pyrrolidin-1-yl)-4-(trifluoromethyl)benzyl)piperazine-1-carboxylate hydrochloride drug substance is stoichiometrically equivalent to 2.00 mg 1,1,1,3,3,3-hexafluoropropan-2-yl 4-(2-(pyrrolidin-1-yl)-4-(trifluoromethyl)benzyl)piperazine-1-carboxylate as free base
[2]10.72 mg 1,1,1,3,3,3-hexafluoropropan-2-yl 4-(2-(pyrrolidin-1-yl)-4-(trifluoromethyl)benzyl)piperazine-1-carboxylate hydrochloride drug substance is stoichiometrically equivalent to 10.00 mg 1,1,1,3,3,3-hexafluoropropan-2-yl 4-(2-(pyrrolidin-1-yl)-4-(trifluoromethyl)benzyl)piperazine-1-carboxylate as free base
[3]53.60 mg 1,1,1,3,3,3-hexafluoropropan-2-yl 4-(2-(pyrrolidin-1-yl)-4-(trifluoromethyl)benzyl)piperazine-1-carboxylate hydrochloride drug substance is stoichiometrically equivalent to 50.00 mg 1,1,1,3,3,3-hexafluoropropan-2-yl 4-(2-(pyrrolidin-1-yl)-4-(trifluoromethyl)benzyl)piperazine-1-carboxylate as free base The following procedure was used to prepare the 1,1,1,3,3,3-hexafluoropropan-2-yl 4-(2-(pyrrolidin-1-yl)-4-(trifluoromethyl)benzyl)piperazine-1-carboxylate hydrochloride capsules:

1. Weigh a sufficient number of capsules to fill batch;

2. Weigh 1,1,1,3,3,3-hexafluoropropan-2-yl 4-(2-(pyrrolidin-1-yl)-4-(trifluoromethyl)benzyl)piperazine-1-carboxylate hydrochloride, microcrystalline cellulose, croscarmellose sodium, and magnesium stearate;
3. Sieve each of the following: 1,1,1,3,3,3-hexafluoropropan-2-yl 4-(2-(pyrrolidin-1-yl)-4-(trifluoromethyl)benzyl)piperazine-1-carboxylate hydrochloride, microcrystalline cellulose and croscarmellose sodium;
4. Transfer the sieved materials (1,1,1,3,3,3-hexafluoropropan-2-yl 4-(2-(pyrrolidin-1-yl)-4-(trifluoromethyl)benzyl)piperazine-1-carboxylate hydrochloride, microcrystalline cellulose and croscarmellose sodium) into a blender and blend material for 15 minutes;
5. Sieve the magnesium stearate and add it to the blender in Step 4. Blend the material for 2 minutes;
6. Fill the blend into each of the size no 2 Swedish orange capsules and ensure capsules are snapped closed.

Example 4: Pharmaceutical Formulation 1,1,1,3,3,3-Hexafluoropropan-2-yl 4-(2-(pyrrolidin-1-yl)-4-(trifluoromethyl)benzyl)piperazine-1-carboxylate hydrochloride; Tablets, 2 mg of free base per tablet:

| Component | mg/unit | % |
|---|---|---|
| 1,1,1,3,3,3-Hexafluoropropan-2-yl 4-(2-(pyrrolidin-1-yl)-4-(trifluoromethyl)benzyl)piperazine-1-carboxylate hydrochloride | 2.14[1] | 1.43 |
| Polyvinyl pyrrolidone K30 (PVP K30) | 15.06 | 10.04 |
| PEG 400 | 1.60 | 1.07 |
| Polysorbate 80 (Tween 80) | 0.40 | 0.27 |
| Silicon dioxide | 0.40 | 0.27 |
| Potassium dihydrogen phosphate | 0.40 | 0.27 |
| Microcrystalline cellulose | 121.70 | 81.13 |
| Croscarmellose sodium | 7.50 | 5.0 |
| Sodium stearyl fumarate | 0.75 | 0.50 |
| Total: | 150.00 | 100.00 |
| Opadry AMB II Beige | 6.00 | 4.00 |
| Total: | 156.00 | 104.00 |

[1] 2.14 mg 1,1,1,3,3,3-hexafluoropropan-2-yl 4-(2-(pyrrolidin-1-yl)-4-(trifluoromethyl)benzyl)piperazine-1-carboxylate hydrochloride drug substance is stoichiometrically equivalent to 2.00 mg 1,1,1,3,3,3-hexafluoropropan-2-yl 4-(2-(pyrrolidin-1-yl)-4-(trifluoromethyl)benzyl)piperazine-1-carboxylate as free base 1,1,1,3,3,3-Hexafluoropropan-2-yl 4-(2-(pyrrolidin-1-yl)-4-(trifluoromethyl)benzyl)piperazine-1-carboxylate hydrochloride, polyvinyl pyrrolidone (PVP K30), PEG 400, potassium dihydrogen phosphate, and polysorbate 80 (Tween 80) were mixed to get a uniform mixture. The mixture was blended with silicon dioxide to obtain a free flowing blend. The blend was extruded using a twin screw extruder. The extrudate was then milled. The milled extrudate was blended with microcrystalline cellulose 102, croscarmellose sodium, and sodium stearyl fumarate to obtain a uniform tablet blend. The tablet blend was compressed into tablets. The tablets were coated with an Opadry AMB II beige coating in a pan coater.

What is claimed is:

1. A pharmaceutical formulation in a solid dosage form comprising:
   (a) 1 mg to 60 mg of 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt thereof;
   (b) 50 mg to 175 mg of microcrystalline cellulose;
   (c) 6 mg to 15 mg of croscarmellose sodium; and
   (d) 0.5 mg to 2.5 mg of magnesium stearate.

2. The pharmaceutical formulation of claim 1, wherein the 1,1,1,3,3,3-hexafluoropropan-2-yl 4-(2-(pyrrolidin-1-yl)-4-(trifluoromethyl)benzyl)piperazine-1-carboxylate is a hydrochloride salt.

3. The pharmaceutical formulation in a solid dosage form according to claim 1 comprising:
   (a) 2.1 mg of 1,1,1,3,3,3-hexafluoropropan-2-yl 4-(2-(pyrrolidin-1-yl)-4-(trifluoromethyl)benzyl)piperazine-1-carboxylate hydrochloride salt;
   (b) 156 mg of microcrystalline cellulose;
   (c) 10 mg of croscarmellose sodium; and
   (d) 1.7 mg of magnesium stearate.

4. The pharmaceutical formulation in a solid dosage form according to claim 1 comprising:
   (a) 10.7 mg of 1,1,1,3,3,3-hexafluoropropan-2-yl 4-(2-(pyrrolidin-1-yl)-4-(trifluoromethyl)benzyl)piperazine-1-carboxylate hydrochloride salt;
   (b) 147 mg of microcrystalline cellulose;
   (c) 10.2 mg of croscarmellose sodium; and
   (d) 1.7 mg of magnesium stearate.

5. The pharmaceutical formulation in a solid dosage form according to claim 1 comprising:
   (a) 53.6 mg of 1,1,1,3,3,3-hexafluoropropan-2-yl 4-(2-(pyrrolidin-1-yl)-4-(trifluoromethyl)benzyl)piperazine-1-carboxylate hydrochloride salt;
   (b) 104 mg of microcrystalline cellulose;
   (c) 10 mg of croscarmellose sodium; and
   (d) 1.7 mg of magnesium stearate.

6. The pharmaceutical formulation of claim 1, wherein the solid dosage form is a tablet.

7. The pharmaceutical formulation of claim 2, wherein the solid dosage form is a tablet.

8. The pharmaceutical formulation of claim 3, wherein the solid dosage form is a tablet.

9. The pharmaceutical formulation of claim 4, wherein the solid dosage form is a tablet.

10. The pharmaceutical formulation of claim 5, wherein the solid dosage form is a tablet.

11. The pharmaceutical formulation of claim 1, wherein the solid dosage form is a capsule.

12. The pharmaceutical formulation of claim 2, wherein the solid dosage form is a capsule.

13. The pharmaceutical formulation of claim 3, wherein the solid dosage form is a capsule.

14. The pharmaceutical formulation of claim 4, wherein the solid dosage form is a capsule.

15. The pharmaceutical formulation of claim 5, wherein the solid dosage form is a capsule.

* * * * *

UNITED STATES PATENT AND TRADEMARK OFFICE
CERTIFICATE OF CORRECTION

| | | |
|---|---|---|
| PATENT NO. | : 11,273,159 B2 | Page 1 of 1 |
| APPLICATION NO. | : 16/349042 | |
| DATED | : March 15, 2022 | |
| INVENTOR(S) | : Grice et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 130 days.

Signed and Sealed this
Eighteenth Day of February, 2025

Coke Morgan Stewart
*Acting Director of the United States Patent and Trademark Office*